United States Patent [19]

Peterson et al.

[11] Patent Number: 5,783,431
[45] Date of Patent: Jul. 21, 1998

[54] METHODS FOR GENERATING AND SCREENING NOVEL METABOLIC PATHWAYS

[75] Inventors: Todd C. Peterson, Chula Vista; Lyndon M. Foster, Carlsbad; Paul Brian, San Diego, all of Calif.

[73] Assignee: Chromaxome Corporation, San Diego, Calif.

[21] Appl. No.: 738,944

[22] Filed: Oct. 24, 1996

Related U.S. Application Data

[63] Continuation-in-part of Ser. No. 639,255, Apr. 24, 1996.
[51] Int. Cl.$^6$ ............................ C12N 15/64; C07H 21/04
[52] U.S. Cl. ............................ 435/172.3; 435/320.1; 536/23.1
[58] Field of Search ............................ 536/23.1; 435/172.3, 435/320.1

[56] References Cited

U.S. PATENT DOCUMENTS

| 4,399,219 | 8/1983 | Weaver | 435/34 |
|---|---|---|---|
| 5,326,691 | 7/1994 | Hozier | 435/6 |
| 5,434,065 | 7/1995 | Mahan et al. | 435/172.3 |
| 5,441,885 | 8/1995 | Goldberg | 435/254.34 |
| 5,506,126 | 4/1996 | Seed et al. | 435/172.3 |
| 5,527,896 | 6/1996 | Wigler et al. | 536/23.5 |

FOREIGN PATENT DOCUMENTS

| EP 0 534 619 | 3/1993 | European Pat. Off. . |
|---|---|---|
| WO 93/06213 | 4/1993 | WIPO . |
| WO 94/23025 | 10/1994 | WIPO . |
| W o 94/29469 | 12/1994 | WIPO . |
| WO 94/29462 | 12/1994 | WIPO . |
| Wo 95/08548 | 3/1995 | WIPO . |
| WO 95/30012 | 11/1995 | WIPO . |

OTHER PUBLICATIONS

Frost et al. Analysis of the sequence and gene products of the transfer region of the F sex factor. Microbiological Reviews vol. 58 pp. 162–210.

Arisawa et al., "Cloning of the Macrolide Antibiotic Biosynthesis Gene AcyA, Which Encodes 3–0–Acyltransferase, From Streptomyces Thermotolerans and Its Use for Direct Fermentative Production of a Hybrid Macrolide Antibiotic", Appl. Env. Micro. 60(7):2657–2660 (1994).

Fu et al., "Engineered Biosynthesis of Novel Polyketides: Stereochemical Course of Two Reactions Catalyzed by a Polyketide Synthase" Biochemistry 33:9321–9326 (1994.

Kao et al., "Engineered Biosynthesis of a Complete Macrolactone in a Heterologous Host" Science 265:509–511 (1994).

Rani et al., "Cloning and Expression of the Mercury Resistance Genes of Marine Pseudomonas Sp. Strain MR1 Plasmid pMR1 in Escherichia Coli," Res. Microbiol. 145:121–127 (1994).

McDaniel et al., "Engineered Biosynthesis of Novel Polyketides", Science 262:1546–1550 (1993).

Murdock et al., "Construction of Metabolic Operon Catalyzing the De Novo Biosynthesis of Indigo in Escherichia Coli" Bio/Technology 11:381–385 (1993).

Steglitz–Morsdorf et al., "Cloning Heterologous Expression and Sequencing of the Proteus Vulgaris glnAntrBC Operon, and Implications of Nitrogen Control on Heterologous Urease Expression", FEMS Microbiol Lett, 106:157–164 (1993).

LaCalle et al., "Cloning of the Complete Biosynthetic Gene Cluster for an Aminonucleoside Antibiotic, Puromycin, and its Regulated Expression in Heterologous Hosts" EMBO J. 2:785–792 (1992).

Hundle et al., "Carotenoids of Erwinia Herbicola and an Escherichia Coli HB101 Strain Carrying the Erwinia Herbicola Gene Cluster", Photochem. and Photobiol. 54(1):89–93 (1991).

Thanabalu et al., "Cloning, Sequencing and Expression of a Gene Encoding a 100–Kilodalton Mosquitocidal Toxin from Bacillus sphaericus SSII–1" J. Bact. 173:2776–2785 (1991).

Sarwar et al., "Cloning of Aminoglycoside Phosphotransferase (APH) Gene from Antbiotic–Producing Strain of Bacillus Circulans into a High–Expression Vector, pKK233–3", Biochem. J. 268:671–677 (1990).

Rojo et al., "Assemblage of Ortho Cleavage Route for Simultaneous Degradation of Chloro—and Methylaromatics" Science 238:1395–1398 (1987).

Malpartida et al., "Molecular Cloning of the Whole Biosynthetic Pathway of a Streptomyces Antibiotic and its Expression in a Heterologous Host", Nature 309:462–464 (1984).

Ensley et al., "Expression of Napthalene Oxidation Genes in Escherichia Coli Results in the Biosynthesis of Indigo" Science 222:167–169 (1983).

Dunlap et al., "Characterization of a Periplasmic 3':5'—Cyclic Nucleotide Phosphodiesterase Gene, cpdP, from the Marine Symbiotic Bacterium Vibrio Fischeri", J. Bact. 175(15):4615–4624 (1993).

Fukagawa et al., "Cloning of Gene Responsible for Tributyltin Chloride (TBTCI) Resistance in TBTCI–Resistant Marine Bacterium, Alteromonas S. M—1", Biochem. Biophys. Res. Comm. 194(2):733–740 (1993).

(List continued on next page.)

Primary Examiner—James Ketter
Assistant Examiner—John S. Brusca
Attorney, Agent, or Firm—Pennie & Edmonds LLP

[57] ABSTRACT

The present invention relates to a novel drug discovery system for generating and screening molecular diversity. The system provides methods for mixing and cloning genetic materials from a plurality of species of organisms in combinatorial gene expression libraries to generate novel metabolic pathways and classes of compounds. The system also provides mobilizable combinatorial gene expression libraries that can be transferred from one species of host organism to another for expression. Also provided are specialized cloning vectors for making mobilizable gene expression libraries. The system also involves methods for pre-screening or identifying for host organisms containing a library that are capable of generating such novel pathways and compounds.

25 Claims, 23 Drawing Sheets

OTHER PUBLICATIONS

Tsujibo et al., "Cloning, Sequence, and Expression of a Chitinase Gene from a Marine Bacterium, Alteromonas Sp. Strain 0–7", J. Bact. 175(1):176–181 (1993).

Danaher et al., "Expression of Cloned Restriction and Modification Genes, hjaIRM from Hyphomonas Jannaschiana in Escherichia Coli", Gene 89:129–133 (1992).

David et al., "Cloning, Sequencing, and Expression of the Gene Encoding the Extracellular Neutral Protease, Vibriolysin, of Vibrio Proteolyticus", Gene 112:107–112 (1992).

MacLeod et al., "Identification and Sequence of Na+— Linked Gene from the Marine Bacterium Alteromonas Haloplanktis Which Functionally Complements the dagA Gene of Escherichia Coli", Mol. Micro. 6(18):2673–2681 (1992).

Sorum et al., "Identification and Cloning of a Tetrcycline Resistance Gene From the Fish Pathogen Vibrio Salmonicida", Antimicro. Agents Chemo. 36(3):611–615 (1992).

Fuqua et al., "Characterization of melA: A Gene Encoding Malanin Biosynthesis from the Marine Bacterium Shewanella colwelliana", Gene 109:131–136 (1991).

Nakamura et al., "Cloning and Sequencing of an Na+/H+ Antiporter Gene from the Marine Bacterium Vibrio Alginolyticus"., Biochim. Biophys. Acta 1190:465–468 (1990).

Barbeyron et al., "The Gene Encoding the Kappa–Carrageenase of Alteromonas Carrageenovora is Related to Beta— 1, 3—1, 4—Glucanases"., Gene 139:105–109 (1982).

Huse, "Construction of Combinatorial Antibody Expression Libraries in Escherichia Coli" CIBA Foundation Symposium 159, p. 91–102 (1991).

Simonsen et al., "Cloning by Function: Expression Cloning in Mammalian Cells" Trends in Pharm. SCi. 15:437–441 (1994).

Luyten et al., "Receptor Cloning and Heterologous Expression Towards a New Tool for Drug Discovery" Trends in Biotech. 11:247–54 (1993).

Nakayama et al., "Use of Mammalian Cell Expression Cloning Systems to Identify Genes for Cytokines, Receptors and Regulatory Proteins" Curr. Opin. Biotech. 3:497–505 (1992).

Shizuya et al., "Cloning and Stable Maintenance of 300–Kilobase–Pair Fragments of Human DNA in E. Coli Using an F–Factor–Based Vector", Proc. Natl. Acad. Sci. USA 89:8794–8797 (1992).

Aruffo, "Expression Cloning Systems" Curr. Opin. Biotech. 2:735–741 (1991).

Clarke et al., "A Colony Bank Containing Synthetic Col E–1 Hybrid Plasmids Representative of the Entire E. Coli Genome", Cell 9:91–99 (1976).

Hutchinson, "Drug Synthesis by Genetically Engineered Microorganisms" Bio/technology 12:375–379 (1994).

Ecker et al., "Combinatorial Drug Discovery: Which Methods Will Produce the Greatest Value?", Bio/Technology 13:351–360 (April 1995).

Katz et al., "Polyketide Synthesis Prospects for Hybrid Antibiotics", An. Rev. Microbiol. 47:875–912 (1993).

Fenical and Jenson, Marine Microorganisms: A New Biomedical Resource. Advances in Marine Biotechnology, vol. I: Pharmaceutical and Bioactive Natural Products , pp. 419–457, D. Attaway, O. Zaborsky, eds., Plenum Press, New York. (1992).

Hopwood et al., in Secondary Metabolites: Their Function and Evolution , Wiley, Clichester (CIBA Foundation Symposium 171) p. 88–122 (1992).

Floss et al., "Genetic Engineering of Hybrid Antibiotics—a Progress Report", Tetrahedron 47:6045–6058 (1991).

Tapiolas et al., "Octalactins A and B, Cytotoxic 8–Membered Ring Lactones from the Marine Bacterium Streptomyces Sp.", J. Amer. Chem. Soc. 113:4682–4683 (1991).

Orser et al., "Use of Prokaryotic Stress Promoters as Indicators of the Mechanism of Chemical Toxicity", In Vitro Toxicology 8(1):71–85 (1995).

Cohen et al., "Genetic and Functional Analysis of the Multiple Antibiotic Resistance (MAR) Locus in Escherichia Coli ", J. Bact. 175(5):1484–1492 (1993).

Cohen et al., "Salicylate Induction of Antibiotic Resistance in Escherichia Coli: Activation of the MAR Operon and a MAR–Independant Pathway", J. Bact. 175(24):7859–7862 (1993).

Corbisier et al., "LuxAB Gene Fusions with the Arsenic and Cadmiun Resistance Operons of Staphylococcus Aureus Plasmid pI258", FEMS Microbiology Letters 110(2):231–238 (1993).

de Lorenzo et al., "Engineering of Alkyl—and Haloaromatic–Responsive Gene Expression with Mini–Transposons Comntaining Regulated Promoters of Biodegradative Pathways of Pseudomonas ", Gene 130:41–46 (1993).

Metcalf et al., "Mutational Analysis of an Escherichia Coli Fourteen–Gene Operon for Phosphonate Degradation, Using TnophoA' Elements", J. Bact. 175(11):3430–3442 (1993).

Mekalanos, "Environmental Signals Controlling Expression of Virulence Determinants in Bacteria, " J. Bacteriol. 174:1–7 (1992).

Slauch et al., "Genetic Fusions as Experimental Tools, " Methods in Enzymology, 204:213–249 (1991).

Ramos et al., "Broad–Hos Range Expression Vectors Containing Manipulated Meta–Cleavage Pathway Regulatory Elements of the TOL Plasmid", FEBS Letters 226(2):241–246 (1988).

Mermod et al., "Vector for Regulated Expression of Cloned Genes in a Wide Range of Gram–Negative Bacteria", J. Bact. 167(2):447–454 (1986).

Ramos et al., "Altered Effector Specificities in Regulators of Gene Expression: TOL Plasmid xylS Mutants and Their Use to Engineer Expansion of the Range of Aromatics Degraded by Bacteria", Proc. Natl. Acad. Sci. USA 83:8467–8471 (1986).

Reznikoff et al., "The Regulation of Transcription Initiation in Bacteria", Annual Review of Genetics 19:355–387 (1985).

Heim et al., "Improved Green Fluorescence", Nature 373(6516):663–664 (1995).

Lu et al., "Expression of Yjioredoxin Random Peptide Libraries on the Escherichia Coli Cell Surface as Functional Fusions to Flagelin: A System Designed for Exploring Protein–Protein Interactions", Bio/Technology 13:366–372 (1995).

Chalfie et al., "Green Fluorescent Protein as a Marker for Gene Expression", Science 263:802–805 (1994).

Schechter et al., "Fluorescence Dye as Monitor of Internal pH in E. Coli Cells", FEBS Letters 139:121 (1982).

BEntley et al., "The Development and Application of Automated Gridding for Efficient Screening of Yeast and Bacterial Ordered Libraries", Genomics 12:534–541 (1992).

Bronstein et al., "Cheimiluminescent and Bioluminescent Gene Assays", Anal. Biochem. 219:169–181.

Geiselhart et al., "Construction and Evaluation of a Self-Luminescent Biosensor" Annals NY Acad. Sci. 646:53–60 (1991).

Franco et al., "Detection of Novel Secondary Metabolites", In *Critical Reviews in Biotechnology*, vol. 11(3):193–276 (1991).

Powell et al., "Gel Microdroplets and Flow Cytometry: Rapid Determination of Antibody Secretion by Individual Cells Within a Cell Population", Bio/Technology 8:333–337 (1990).

Nolan et al., "Fluorescence–Activated Cell Analysis and Sorting of Viable Mammalian Cells Based on β—D—Galactosidase Activity after Transduction of *Escherischia Coli* LacZ", Proc. Natl. Acad. Sci. USA 85:203 (1988).

Weaver et al., "Gel Microdroplets; Rapid Detection and Enumeration of Individual Microorganisms by Their Metabolic Activity", Bio/Technology 6:1084–1089 (1988).

Berdy et al., "Search and Discovery Methods for Novel Antimicrobials". In *Bioactive Metabolites From Micro-Organisms*, pp. 3–25, M. E. Bushnell, U. Grafe, eds., Elsevier, Amsterdam. (1982).

Johnson et al., "Plasmid RK2 Toxin Protein ParE: Purification and Interaction with the ParD Antitoxin Protein", J. Bacteriol. 178:1420–1429 (1996).

Brun et al., "pDblet, a Stable Autonomously Replicating Shuttle Vector for *Schizosaccharomyces pombe* ", Gene 164:173–177 (1995).

Kovach et al., "pBBR1MCS: A Broad–Host–Range Cloning Vector", BioTechniques 16:800–802 (1994).

Pansegrau et al., "CompleteNucleotide Sequence of Birmingham IncPα Plasmids. Compilation and Comparative Analysis", J. Biol. 239:623–663 (1994).

Hayman et al., "Movement of Shuttle Plasmids from *Escherichia coli* into Yeasts Other Than *Saccharomyces cerevisiae* Using Trans–Kingdom Conjugation", Plasmid 30:251–257 (1993).

Davis et al., "Spore Colour in *Streptomyces coelicolor* A3(2) Involves the Developmentally Regulated Synthesis of a Compound Biosynthetically Related to Polyketide Antibiotics", Mol. Microbiol. 4:1679–1691 (1990).

Muth et al., "A Vector System with Temperature–Sensitive Replication for Gene Disruption and Mutational Cloning in Streptomyces", Mol. Gen. Benet. 219:341–348 (1989).

Sambrook et al., "Molecular Cloning, A Laboratory Manual"2nd. ed., Cold Spring Harbor laboratory Press, pp. xi–xxxv (table of contents), (1989).

Feitelson et al., "Genetic and Biochemical Characterization of the *red* Gene Cluster of *Streptomyces coelicolor* A3(2)", J. Gen. Microbiol. 131:2431–2441 (1985).

Lydiate et al., "The Streptomyces Plasmid SCP2*: Its Functional Analysis and Development into Useful Cloning Vectors", Gene 35:223–235 (1985).

Brau et al., "Genes for Gentamicin–(3)–N–Acetyltransferases III and IV: I. Nucleotide Squence of the AAC(3)–IV Gene and Possible Involvement of an IS140 Element in Its Expression", Mol. Gen. Genet. 193:179–187 (1984).

Kaster et al., "Analysis of a Bacterial Hygromycin B Resistance Gene by Transcriptional and Translational Fusions and by DNA Sequencing", Nucl. Acids Res. 11:6895–6911 (1983).

Knauf and Nester, "Wide Host Range Cloning Vectors: A Cosmid Clone Bank of an Agrobacterium Ti Plasmid", 8:45–54 (1982).

Maniatis et al., "Molecular Cloning, A Laboratory Manual", Cold Spring harbor laboratory, pp. 229–246, 295–296, (1982).

Ditta et al., "Broad Host Range DNA Cloning System for Gram–Negative Bacteria: Construction of a Gene Bank of *Rhizobium Meliloti* ", Proc. Natl. Acad. Sci. USA 77:7347–7351 (1980).

Figurski and Helinski, "Replication of an Origin–Containing Derivative of Plasmid RK2 Dependent on a Plasmid Function Provided in *trans* ", Proc. Natl. Acad. Sci. USA 76:1648–1652 (1979).

Hopwood et al., "Genetic Manipulation of Streptomyces, A Laboratory Manual", The John Innes Foundation, Norwich, England, pp. v–vxii (table of contents), (1985).

TERMINATORS
FOR cDNA INSERTS

5'- GATCCCCGGG..PCR TERMINATOR...GGATCCCGGC-3'
3'- CTAGGGGCCC... FRAGMENT ...CCTAGGGCCG-5'
   BamHI

↓ CUT ONLY WITH Xma I

5'- CCGGG..PCR TERMINATOR...GGATCCCGGC-3'
3'-    C... FRAGMENT    ...CCTAGGGCCG-5' P
   Xma I                    BamHI

↓ FILL IN WITH dCTP

5'- CCGGG..PCR TERMINATOR...GGATCCCGGC-3'
3'- CCC... FRAGMENT    ...CCTAGGGCCG-5' P
   Xma I                    BamHI

↓ TREAT W/ PHOSPHATASE

5'- CCGGG..PCR TERMINATOR...GGATCCCGGC-3'
3'- CCC... FRAGMENT    ...CCTAGGGCCG-5'
   Xma I                    BamHI

→ TERMINATORS READY TO
  LIGATE TO cDNA INSERTS

PROMOTERS FOR
cDNA & gDNA INSERTS

DISSIMILAR ENZYMES ON PROMOTER &
TERMINATOR FRAGMENTS ASSURE
DIRECTIONAL CLONING OF cDNA INSERTS,
(FOR EXAMPLE Xho I & Xma I)

ENZYME CLEAVAGE GENERATES
DEFINED ENDS, LEAVING
PROTECTED 3' BamHI SITE

KLENOW FILL IN OF
PROMOTERS & TERMINATORS
FRAGMENTS MAKE THEM INCAPABLE
OF INTER/INTRA LIGATION

PHOSPHATASE TREATMENT
CRATES EQUAL STRENGTH
LIGATION PARTNERS

5'- GAGTAGATCT..PCR PROMOTER..CTCGAGCGGC-3'
3'- CTCATCTAGA.. FRAGMENT ...GAGCTCGCCG-5'
   Bgl II                    Xho I

↓ CUT W/Bgl II & Xho I

5'- GATCT..PCR PROMOTER..C-3'
3'-    A.. FRAGMENT ...GAGCT-5' P
   Bgl II              Xho I

↓ FILL IN WITH dTTP & dCTP

5'- GATCT..PCR PROMOTER..CTC-3'
3'-    A.. FRAGMENT ...GAGCT-5' P
   Bgl II              Xho I

↓ TREAT W/ PHOSPHATASE

5'- GATCT..PCR PROMOTER..CTC-3'
3'-    A.. FRAGMENT ...GAGCT-5'
   Bgl II              Xho I

→ PROMOTERS READY TO
  LIGATE TO INSERTS

MCS = SacI–NcoI–BstXI–NotI–Xba...

5'  CCTAGCCATGGCCACCTAACTGGGATCGC  3'

3'  TCGAGGATCGGTACCGGTGGATTGACCCTAGCGCCGG  5'

SacI    NcoI      BstXI        NotI END

```
POSITION
CXC-AMN20           (1)   - - - - - - - - - - - - - - - - - - - - - - N S H F I T T T Q G V L V F D S G S S E H I G N A    (23)
ACTINORHODIN DEHYDRASE  1 M T V E V R E V A E G V Y A Y E Q A P G G W C V S N A G I V V G G D G A L V V D T L S T I P R A R R   50

CXC-AMN20          (24)  T I A A V K R V T E Q P I R W V V N S H S H A D H W L G N A A L A K L G A E L I S T S L S A E T M K   (73)
ACTINORHODIN DEHYDRASE 51 L A E W V D K L A A G P G R T V V N T H F H G D H A F G N Q V F A P - G T R I I A H E D M R S A M V   99

CXC-AMN20          (74)  S D G P V D V K A F F N M T K G A T G E S T L V I P T S I L H Q Q T R T F G D T E V E F V F A N D    (123)
ACTINORHODIN DEHYDRASE 100 T G L A L T G - L W P - - R V D W G E I E L R P P N V T F R D R L T L H V G E R Q V E L T C V G P   146

CXC-AMN20         (124)  G H S P G D V M L P K Q R I L I G G D V V N S F M P I M T P R G N I T Q L I S V L K E V E Q L    (173)
ACTINORHODIN DEHYDRASE 147 A H T D H D V V W L P E E R V L F A G D V V M S G V T P - F A L F G S V A G T L A A L D R L A E L   195

CXC-AMN20         (174)  S P L L V L T G H G E N T S V K S V S R D I Q F L T Y A S N A V H E A L V K G T T P A K I Q A S L Q    (223)
ACTINORHODIN DEHYDRASE 196 E P E V V G G H G P V A G P E V I D A N R D Y L R W V Q R L A A D A V D R R L T P L Q A A R R A D   245

CXC-AMN20         (224)  A T T L R T K F G K A Y Q D F D T S I S Y L L E M M I D K Q R L Q F S P T - - - - - - - - - - -    (264)
ACTINORHODIN DEHYDRASE 246 L G A F A G L L D A E R L V A N L H R A H E E L L G G H V R D A M E I F A E L V A Y N G G Q L P T C   295

CXC-AMN20          -     - -
ACTINORHODIN DEHYDRASE 296 L A *                                                                                          297
```

FIG.10

METHODS FOR GENERATING AND SCREENING NOVEL METABOLIC PATHWAYS

The application is a continuation-in-part of application Ser. No. 08/639,255, filed Apr. 24, 1996, which is hereby incorporated by reference in their entirety.

TABLE OF CONTENTS

1. FIELD OF THE INVENTION
2. BACKGROUND OF THE INVENTION
   2.1. SOURCES OF DRUG LEADS
   2.2. EXPRESSION LIBRARIES
3. SUMMARY OF THE INVENTION
   3.1. DEFINITIONS
4. DESCRIPTION OF THE FIGURES
5. DETAILED DESCRIPTION OF THE INVENTION
   5.1. PREPARATION OF COMBINATORIAL GENE EXPRESSION LIBRARIES
      5.1.1. DONOR ORGANISMS
      5.1.2. PREPARATION OF HIGH QUALITY NUCLEIC ACIDS FROM DONOR ORGANISMS
      5.1.3. HOST ORGANISMS AND VECTORS
      5.1.4. COMBINATORIAL NATURAL PATHWAY EXPRESSION LIBRARIES
      5.1.5. COMBINATORIAL CHIMERIC PATHWAY EXPRESSION LIBRARIES
      5.1.6. BIASED COMBINATORIAL EXPRESSION LIBRARIES
   5.2. SCREENING COMBINATORIAL EXPRESSION LIBRARIES
      5.2.1. REPORTER CONSTRUCTS
      5.2.2. PHYSIOLOGICAL PROBES AND REPORTER PRECURSORS
      5.2.3. PRE-SCREENING AND SCREENING OF THE LIBRARY
   5.3. PROTOCOLS FOR THE PREPARATION OF HIGH QUALITY NUCLEIC ACIDS FROM DONOR ORGANISMS
      5.3.1. GUANIDINIUM ISOTHIOCYANATE NUCLEIC ACID ISOLATION
      5.3.2. ISOLATION OF POLY(A)-CONTAINING RNA
      5.3.3. ENRICHMENT OF NON-RIBOSOMAL SEQUENCES FROM TOTAL RNA
      5.3.4. FILL-IN REACTION USING THE KLENOW FRAGMENT
      5.3.5. PROTOCOLS FOR PREPARATION OF SUBTRACTED DNA PROBES FOR PRE-SCREENING
      5.3.6. PURIFICATION OF NUCLEIC ACIDS FROM SOIL OR OTHER MIXED ENVIRONMENTAL SAMPLES
      5.3.7. REPAIR OF DNA
   5.4. PROTOCOLS FOR PROKARYOTIC EXPRESSION LIBRARIES
      5.4.1. BACTERIAL SPECIES, STRAINS, AND CULTURE CONDITIONS
      5.4.2. PREPARATION OF DONOR GENOMIC DNA
      5.4.3. GENERATION OF PROKARYOTIC PROMOTER FRAGMENTS
      5.4.4. PREPARATION OF GENE CASSETTES FOR COMBINATORIAL CHIMERIC PATHWAY EXPRESSION LIBRARIES
      5.4.5. PREPARATION OF SOLID SUPPORT
      5.4.6. ASSEMBLY OF A COMBINATORIAL CHIMERIC PATHWAY EXPRESSION LIBRARY
      5.4.7. ASSEMBLY OF A COMBINATORIAL NATURAL PATHWAY EXPRESSION LIBRARY
      5.4.8. PRE-SCREENING OF EXPRESSION LIBRARIES
      5.4.9. METABOLIC TESTING OF MARINE GRAM (−)/*E. COLI* LIBRARY BY PLATE REPLICATION
      5.4.10. METABOLIC TESTING OF MARINE GRAM (−)/*E. COLI* LIBRARY BY MACRODROPLET ENCAPSULATION
      5.4.11. METABOLIC TESTING OF MARINE GRAM (−)/*E. COLI* LIBRARIES BY MICRODROPLET ENCAPSULATION
      5.4.12. METABOLIC TESTING OF ACTINOMYCETES/*STREPTOMYCES LIVIDANS* LIBRARY BY PLATE REPLICATION
      5.4.13. METABOLIC TESTING OF ACTINOMYCETES/*STREPTOMYCES LIVIDANS* LIBRARY BY MACRODROPLET ENCAPSULATION
      5.4.14. PRE-SCREENING OF CLONES BY CO-ENCAPSULATION WITH INDICATOR CELLS
   5.5. PROTOCOLS FOR EUKARYOTIC EXPRESSION LIBRARIES
      5.5.1. REMOVAL OF SATELLITE GENOMIC DNA BY DENSITY GRADIENT CENTRIFUGATION
      5.5.2. GENERATION OF EUKARYOTIC PROMOTERS AND TERMINATOR FRAGMENTS
      5.5.3. PREPARATION OF DNA INSERTS
      5.5.4. LIGATION OF INSERT DNA TO PROMOTERS AND TERMINATORS
      5.5.5. SERIAL LIGATIONS OF GENE CASSETTES TO FORM CONCATEMERS
      5.5.6. CIRCULARIZATION AND TRANSFORMATION OF VECTOR CONTAINING Concatemer CONSTRUCTS
      5.5.7. PREPARATION AND LIGATION OF PREPARED VECTOR FOR EXPRESSION IN YEAST
      5.5.8. PLANT EXPRESSION LIBRARIES
6. EXAMPLE: CONSTRUCTION AND SCREENING OF COMBINATORIAL GENE EXPRESSION LIBRARY
   6.1. MATERIALS AND METHODS
      6.1.1. MEDIA PREPARATION
   6.2. PRE-SCREENING OF *ACTINOMYCETES/STREPTOMYCES LIVIDANS* COMBINATORIAL NATURAL PATHWAY EXPRESSION LIBRARY BY PLATE REPLICATION AND MACRODROPLET ENCAPSULATION
   6.3. PRE-SCREENING OF *ACTINOMYCETES/E. COLI* COMBINATORIAL CHIMERIC PATHWAY EXPRESSION LIBRARY BY MACRODROPLET ENCAPSULATION
   6.4. PRE-SCREENING OF FUNGAL/*SCHIZOSACCHAROMYCES POMBE* COMBINATORIAL CHIMERIC PATHWAY EXPRESSION LIBRARIES BY MACRODROPLET ENCAPSULATION
   6.5. PRE-SCREENING OF MARINE GRAM(−)/*E. COLI* LIBRARY BY PLATE REPLICATION
   6.6. PRE-SCREENING OF MARINE GRAM(−)/*E. COLI* LIBRARY BY MACRODROPLET ENCAPSULATION
7. EXAMPLE: CONSTRUCTION AND SCREENING OF *ACTINOMYCETES/STREPTOMYCES LIVIDANS* COMBINATORIAL GENE EXPRESSION LIBRARY
   7.1. MATERIALS AND METHODS
   7.2. RESULTS

1. FIELD OF THE INVENTION

The present invention relates to a novel approach to drug discovery. More particularly, the invention relates to a system for preserving the genomes of organisms that are good or promising sources of drugs; for randomly combining genetic materials from one or more species of organisms to generate novel metabolic pathways; and for pre-screening or screening such genetically engineered cells for the generation of novel biochemical pathways and the production of novel classes of compounds. The novel or reconstituted metabolic pathways can have utility in commercial production of the compounds.

2. BACKGROUND OF THE INVENTION
2.1. SOURCES OF DRUG LEADS

The basic challenges in drug discovery are to identify a lead compound with the desirable activity, and to optimize the lead compound to meet the criteria required to proceed with further drug development. One common approach to drug discovery involves presenting macromolecules implicated in causing a disease (disease targets) in bioassays in which potential drug candidates are tested for therapeutic activity. Such molecules could be receptors, enzymes or transcription factors.

Another approach involves presenting whole cells or organisms that are representative of the causative agent of the disease. Such agents include bacteria and tumor cell lines.

Traditionally, there are two sources of potential drug candidates, collections of natural products and synthetic chemicals. Identification of lead compounds has been achieved by random screening of such collections which encompass as broad a range of structural types as possible. The recent development of synthetic combinatorial chemical libraries will further increase the number and variety of compounds available for screening. However, the diversity in any synthetic chemical library is limited to human imagination and skills of synthesis.

Random screening of natural products from sources such as terrestrial bacteria, fungi, invertebrates and plants has resulted in the discovery of many important drugs (Franco et al. 1991, Critical Rev Biotechnol 11:193–276; Goodfellow et al. 1989, in "Microbial Products: New Approaches", Cambridge University Press, pp. 343–383; Berdy 1974, Adv Appl Microbiol 18:309–406; Suffness et al. 1988, in Biomedical Importance of Marine Organisms, D. G. Fautin, California Academy of Sciences, pages 151–157). More than 10,000 of these natural products are biologically active and at least 100 of these are currently in use as antibiotics, agrochemicals and anti-cancer agents. The success of this approach of drug discovery depends heavily on how many compounds enter a screening program. Typically, pharmaceutical companies screen compound collections containing hundreds of thousands of natural and synthetic compounds. However, the ratio of novel to previously-discovered compounds has diminished with time. In screens for anti-cancer agents, for example, most of the microbial species which are biologically active may yield compounds that are already characterized. Partly, this is due to the difficulties of consistently and adequately finding, reproducing and supplying novel natural product samples. Since biological diversity is largely due to underlying molecular diversity, there is insufficient biological diversity in the organisms currently selected for random screening, which reduces the probability that novel compounds will be isolated.

Novel bioactivity has consistently been found in various natural sources. See for example, Cragg et al., 1994, (in "Enthnobotany and the search for new drugs" Wiley, Chichester. p178–196). Few of these sources have been explored systematically and thoroughly for novel drug leads. For example, it has been estimated that only 5000 plant species have been studied exhaustively for possible medical use. This is a minor fraction of the estimated total of 250,000–3,000,000 species, most of which grow in the tropics (Abelson 1990, Science 247:513). Moreover, out of the estimated millions of species of marine microorganisms, only a small number have been characterized. Indeed, there is tremendous biodiversity that remains untapped as sources of lead compounds.

Terrestrial microorganisms, fungi, invertebrates and plants have historically been used as sources of natural products. However, apart from several well-studied groups of organisms, such as the *actinomycetes*, which have been developed for drug screening and commercial production, reproducibility and production problems still exist. For example, the antitumor agent, taxol, is a constituent of the bark of mature Pacific yew trees, and its supply as a clinical agent has caused concern about damage to the local ecological system. Taxol contains 11 chiral centers with 2048 possible diastereoisomeric forms so that its de novo synthesis on a commercial scale seems unlikely (Phillipson, 1994, Trans Royal Soc Trop Med Hyg 88 Supp 1:17–19).

Marine invertebrates are a promising source of novel compounds but there exist major weaknesses in the technology for conducting drug screens and large-scale resupply. For instance, marine invertebrates can be difficult to recollect, and many have seasonal variability in natural product content.

Marine microorganisms are a promising source of novel compounds but there also exist major weaknesses in the technology for conducting drug screens and industrial fermentation with marine microorganisms. For instance, marine microorganisms are difficult to collect, establish and maintain in culture, and many have specialized nutrient requirements. A reliable source of unpolluted seawater is generally essential for fermentation. It is estimated that at least 99% of marine bacteria species do not survive on laboratory media. Furthermore, available commercial fermentation equipment is not optimal for use in saline conditions, or under high pressure.

Furthermore, certain compounds appear in nature only when specific organisms interact with each other and the environment. Pathogens may alter plant gene expression and trigger synthesis of compounds, such as phytoalexins, that enable the plant to resist attack. For example, the wild tobacco plant *Nicotiana sylvestris* increases its synthesis of alkaloids when under attack from larvae of *Manduca sexta*. Likewise fungi can respond to phytoalexins by detoxification or preventing their accumulation. Such metabolites will be missed by traditional high-throughput screens, which do not evaluate a fungus together with its plant host. A dramatic example of the influence of the natural environment on an organism is seen with the poison dart frog. While a lethal dose of the sodium channel agonist alkaloid, batrachotoxin, can be harvested by rubbing the tip of a blow dart across the glandular back of a field specimen, batrachotoxin could not be detected in second generation terrarium-reared frogs (Daly, 1995, Proc. Natl. Acad. Sci. 92:9–13). If only traditional drug screening technologies are applied, potentially valuable molecules such as these may never be discovered.

Moreover, a lead compound discovered through random screening rarely becomes a drug, since its potency, selectivity, bioavailability or stability may not be adequate. Typically, a certain quantity of the lead compound is required so that it can be modified structurally to improve its initial activity. However, current methods for synthesis and development of lead compounds from natural sources, especially plants, are relatively inefficient. There are significant obstacles associated with various stages of drug development, such as recollection, growth of the drug-producing organism, dereplication, strain improvement, media improvement, and scale-up production. These problems delay clinical testing of new compounds and affect the economics of using these new sources of drug leads.

At present, the above-mentioned marine, botanical and animal sources of natural products are underused The currently available methods for producing and screening lead compounds cannot be applied efficiently to these underexplored sources. Unlike some terrestrial bacteria and fungi, these drug-producing organisms are not readily amenable to industrial fermentation technologies. Simultaneously, the pressure for finding novel sources for drugs is intensified by new high-efficiency and high-throughput screening technologies. Therefore, there is a general need for methods of harnessing the genetic resources and chemical diversity of these as yet untapped sources of compounds for the purpose of drug discovery.

2.2. EXPRESSION LIBRARIES

Most recently drug discovery programs have shifted to mechanism-based discovery screens. Once a molecular target is identified (e.g., a hormone receptor involved in regulating the disease), assays are designed to identify and/or synthesize therapeutic agents that interact at a molecular level with the target.

Gene expression libraries are used to identify, investigate and produce the target molecules. Expression cloning has become a conventional method for obtaining the target gene encoding a single protein without knowing the protein's physical properties.

Many proteins identified by screening gene expression libraries prepared from human and mammalian tissues are potential disease targets, e.g., receptors (Simonsen et al. 1994, Trends Pharmacol Sci 15:437–441; Nakayama et al. 1992, Curr Opin Biotechnol 3:497–505; Aruffo, 1991, Curr Opin Biotechnol, 2:735–741), and signal-transducing proteins (Margolis et al., U.S. Pat. No. 5,434,064). See Seed et al., 1987, Proc Natl Acad Sci 84:3365–3369; Yamasaki et al., 1988, Science 241:825–828; and Lin et al., 1992, Cell 68:775–785, (type III TGF-β receptor) for examples of proteins identified by functional expression cloning in mammalian cells.

Once a disease target is identified, the protein target or engineered host cells that express the protein target have been used in biological assays to screen for lead compounds (Luyten et al. 1993, Trends Biotechnol 11:247–54). Thus, within the scheme of drug discovery, the use of gene expression libraries has been largely limited to the identification and production of potential protein disease targets. Only in those instances where the drug is a protein or small peptide, e.g., antibodies, have expression libraries been prepared in order to generate and screen for molecules having the desirable biological activity (Huse et al. 1991, Ciba Foundation Symp 159:91–102).

However, there are other applications of gene expression libraries that are relevant to drug discovery. Gene libraries of microorganisms have been prepared for the purpose of identifying genes involved in biosynthetic pathways that produce medicinally-active metabolites and specialty chemicals. These pathways require multiple proteins (specifically, enzymes), entailing greater complexity than the single proteins used as drug targets. For example, genes encoding pathways of bacterial polyketide synthases (PKSs) were identified by screening gene libraries of the organism (Malpartida et al. 1984, Nature 309:462; Donadio et al. 1991, Science 252:675–679). PKSs catalyze multiple steps of the biosynthesis of polyketides, an important class of therapeutic compounds, and control the structural diversity of the polyketides produced. A host-vector system in Streptomyces has been developed that allows directed mutation and expression of cloned PKS genes (McDaniel et al. 1993, Science 262:1546–1550; Kao et al. 1994, Science 265:509–512). This specific host-vector system has been used to develop more efficient ways of producing polyketides, and to rationally develop novel polyketides (Khosla et al., WO 95/08548).

Another example is the production of the textile dye, indigo, by fermentation in an *E. coli* host. Two operons containing the genes that encode the multienzyme biosynthetic pathway have been genetically manipulated to improve production of indigo by the foreign *E. coli* host. (Ensley et al. 1983, Science 222:167–169; Murdock et al. 1993, Bio/Technology 11:381–386). Overall, conventional studies of heterologous expression of genes encoding a metabolic pathway involve directed cloning, sequence analysis, designed mutations, and rearrangement of specific genes that encode proteins known to be involved in previously characterized metabolic pathways.

In view of numerous advances in the understanding of disease mechanisms and identification of drug targets, there is an increasing need for innovative strategies and methods for rapidly identifying lead compounds and channeling them toward clinical testing.

3. SUMMARY OF THE INVENTION

The present invention provides a drug discovery system for generating and screening molecular diversity for the purpose of drug discovery. The method of the invention captures and preserves in combinatorial gene expression libraries the genetic material of organisms that are known/or prospective sources of drug leads.

In one embodiment, the invention involves the construction of combinatorial natural pathway gene expression libraries from one or more species of donor organisms including microbes, plants and animals, especially those that cannot be recovered in substantial amounts in nature, or be cultured in the laboratory. The donor organisms in the pool may be selected on the basis of their known biological properties, or they may be a mixture of known and/or unidentified species of organisms collected from nature. Random fragments of the genomes of donor organisms, some of which contain entire biochemical pathways or portions thereof, are cloned and expressed in the host organisms.

According to the invention, a subset of the gene products of the cloned DNA are capable of functioning in the host organism. The naturally-occurring pathways of the donor organisms may thus be reconstituted in the host organism. The expression of donor genes in the dissimilar physiological and regulatory environment of a heterologous host can unmask otherwise silent metabolic pathways. The metabolic pathways of the donor organism may also interact with metabolic pathways resident in the host organism to generate novel compounds or compounds not normally produced by the host organism.

Moreover, because only a defined subset of donor organism genes is expressed in the host organism at any one time, the system can render metabolic pathways and compounds easier to detect against an already characterized biochemical/cellular background of the host organism. Essentially, the genetic resources of these donor organisms are captured and preserved in the gene expression libraries which can be replicated and used repeatedly in different drug discovery programs.

In another embodiment, the invention involves the construction of combinatorial chimeric pathway expression libraries in which genetic material derived from one or more species of donor organism is randomly combined, cloned, and expressed in the host organism. Such libraries generate random combinations of genes from multiple pathways and organisms, which gives rise to metabolic pathways and discrete gene sets previously non-existent in nature. The term "discrete gene set" refers to any assemblage of two or more genes obtained from the ligation of genes from one or more pathway or organism in a combinatorial gene expression library. The plurality of gene products are capable of functioning in the host organism, where they interact to form novel chimeric metabolic pathways that produce novel classes of compounds. Thus, the diversity of molecular structures available for drug screening is increased by mixing the genetic material of the extant pathways and organisms in the combinatorial chimeric gene expression library.

In yet another embodiment, the invention involves biased combinatorial expression libraries wherein the donor genetic material in the libraries are preselected, and may not contain the entire genome of the donor organisms. The invention also provides mobilizable combinatorial expression libraries in which the cloned donor genetic material can be transferred from one or more species of host organism to at least one other species of host organism.

While standard methods of screening gene expression libraries can be used, the libraries can be further modified to incorporate a reporter regimen tailored to identify clones that are expressing the desirable pathways and metabolic products. In a specific embodiment, the host organisms are engineered to include a gene encoding a reporter protein operatively associated with a chemoresponsive promoter that responds to the desirable class of metabolites to be detected in the expression library.

In an alternative embodiment, the host organism may be exposed to a physiological probe which is a precursor of a reporter molecule that is converted directly or indirectly to the reporter molecule by a compound produced in the pathway sought. Activation of expression of the reporter or conversion of a reporter precursor produces a signal that allows for identification and isolation of the desirable clones.

In yet another embodiment of the invention, the host organisms in the library may be embedded in a semi-solid matrix with a reporter regimen or another indicator cell type that contains an assay or is itself a target for the desirable compound, e.g., pathogens for anti-infectives, or cancer cells for antitumor agents. High-throughput screening processes can be used, e.g., macrodroplet sorting, fluorescence activated cell sorting or magnetic activated cell sorting, to identify and isolate the desired organisms in a combinatorial gene expression library.

The positive clones may be further analyzed for the production of novel compounds. The genetics and biochemistry of the metabolic pathway that lead to production of the novel compounds may be delineated by characterizing the genetic material that was introduced into the isolated clones.

The present invention also relates to recombinant DNA vectors useful for constructing combinatorial gene expression libraries, specific combinatorial gene expression libraries, host organisms containing a particular type of reporter system, host organisms modified for facilitating production of otherwise toxic compounds, and compositions comprising host organisms, indicator cells and/or a reporter regimen.

3.1. DEFINITIONS

As used herein, the following terms will have the meanings indicated.

A "combinatorial natural pathway expression library" is a library of expression constructs prepared from genetic material derived from a plurality of species of donor organisms, in which genes present in the genetic material are operably associated with regulatory regions that drive expression of the genes in an appropriate host organism. The combinatorial expression library utilizes host organisms that are capable of producing functional gene products of the donor organisms. The genetic material in each of the host organism encodes naturally-occurring biochemical pathways or portions thereof from one of the donor organisms.

A "combinatorial chimeric pathway expression library" is a library of expression constructs prepared from randomly concatenated genetic material derived from one or more species of donor organisms, in which genes present in the genetic material are operably associated with regulatory regions that drive expression of the genes in an appropriate host organism. The host organisms used are capable of producing functional gene products of the donor organisms.

A "biased combinatorial gene expression library" is a library of expression constructs prepared from genetic material derived from one or more species of donor organisms, which has been preselected for a specific property. The preselected genetic material can be used to prepare combinatorial natural pathway or chimeric libraries.

A "mobilizable combinatorial gene expression library" is a library of expression constructs prepared from genetic material derived from one or more species of donor organisms, and cloned in a shuttle vector that enables the transfer of the donor genetic materials from one or more species or strain of donor organism to at least one other species or strain of host organism. A shuttle vector can be used to prepare combinatorial natural pathway or chimeric libraries.

As used herein, the term "library" refers to expression constructs or host organisms containing the expression constructs.

The terms "biochemical pathway", "natural pathway" and "metabolic pathway" encompass any series of related biochemical reactions that are carried out by an organism. Such pathways may include but are not limited to biosynthetic or biodegradative pathways, or pathways of energy generation or conversion.

A "compound" is any molecule that is the result or by-product of a biochemical pathway, and is usually the product of interactions of a plurality of gene products.

An "activity" is the capability of a host organism to carry out a biochemical reaction or a series of biochemical reactions leading to the production of a compound of interest.

As used in the present invention, the following abbreviations will apply: eq (equivalents); M (Molar); mM (millimolar); µM (micromolar); N (Normal); mol (moles); mmol (millimoles); µmol (micromoles); nmol (nanomoles); kg (kilograms); gm (grams); mg (milligrams); µg (micrograms); ng (nanograms); L (liters); mL (milliliters); µl (microliters); vol (volumes); s (seconds); and ° C. (degrees Centigrade).

In addition, the following abbreviations are used: Cfu: colony forming units; LB: Luria Broth; ddH$_2$O: doubledistilled, reversed osmosis purified water; sea H$_2$O: Filtered Pacific seawater; SSW: synthetic seawater; FACS: fluorescence-activated cell sorting; GFP: *Aequorea victoria* green fluorescent protein; kbp: Kilobase pairs; g: Gravity; rpm: Rotations per minute; CIAP: Calf intestinal alkaline phosphatase; EDTA: Ethylenediamine tetraacetic acid; TE: 10 mM Tris/1.5 mM EDTA pH 7.4; PEG: Polyethylene glycol; *E. coli: Escherichia coli*; CHO: Chinese hamster ovary; *S. cerevisiae: Saccharomyces cerevisiae; A. nidulans: Aspergillus nidulans; S. pombe: Schizosaccharomyces pombe; S. lividans: Streptomyces lividans; S. aureus: Staphylococcus aureus; S. coelicolor: Streptomyces coelicolor; B. subtilis: Bacillus subtilis*; BAC: Bacterial artificial chromosome; YAC: yeast artificial chromosome; PCR: polymerase chain reaction; CaMV: cauliflower mosaic virus; AcNPV: autographa californica nuclear polyhydrosis virus; EBV: Epstein-Barr virus; SDS: sodium dodecyl sulfate; CsCl: cesium chloride.

4. DESCRIPTION OF THE FIGURES

FIG. 1 Expression construct for combinatorial natural pathway expression library. The expression construct contains vector DNA and a donor DNA fragment that comprises genes encoding a metabolic pathway and natively associated regulatory regions.

FIG. 2 Expression construct for combinatorial chimeric pathway expression library. The expression construct contains vector DNA and five concatenated gene cassettes each comprising donor DNA and regulatory region.

FIG. 3 A cloning strategy for combinatorial natural pathway expression library. Clonable DNA (B) is extracted from donor organisms (A) is partially digested with a restriction enzyme to generate fragments of genomic DNA (C) encoding naturally-occurring biochemical pathways or portions thereof. A DNA vector (D) digested with a restriction enzyme to generate a vector having compatible ends (E) is ligated to the fragments of genomoic DNA to form expression constructs (F).

FIGS. 4A-4C Assembly of a gene cassette. FIG. 4A depicts an annealed, phosphorylated lac promoter fragment containing a cohesive BamHI site and a blunt end corresponding to a portion of a SmaI site. FIG. 4B depicts a promoter dimer containing a BamHI site flanked on each side by a lac promoter. FIG. 4C depicts concatenated promoter fragments.

Figure 5F:
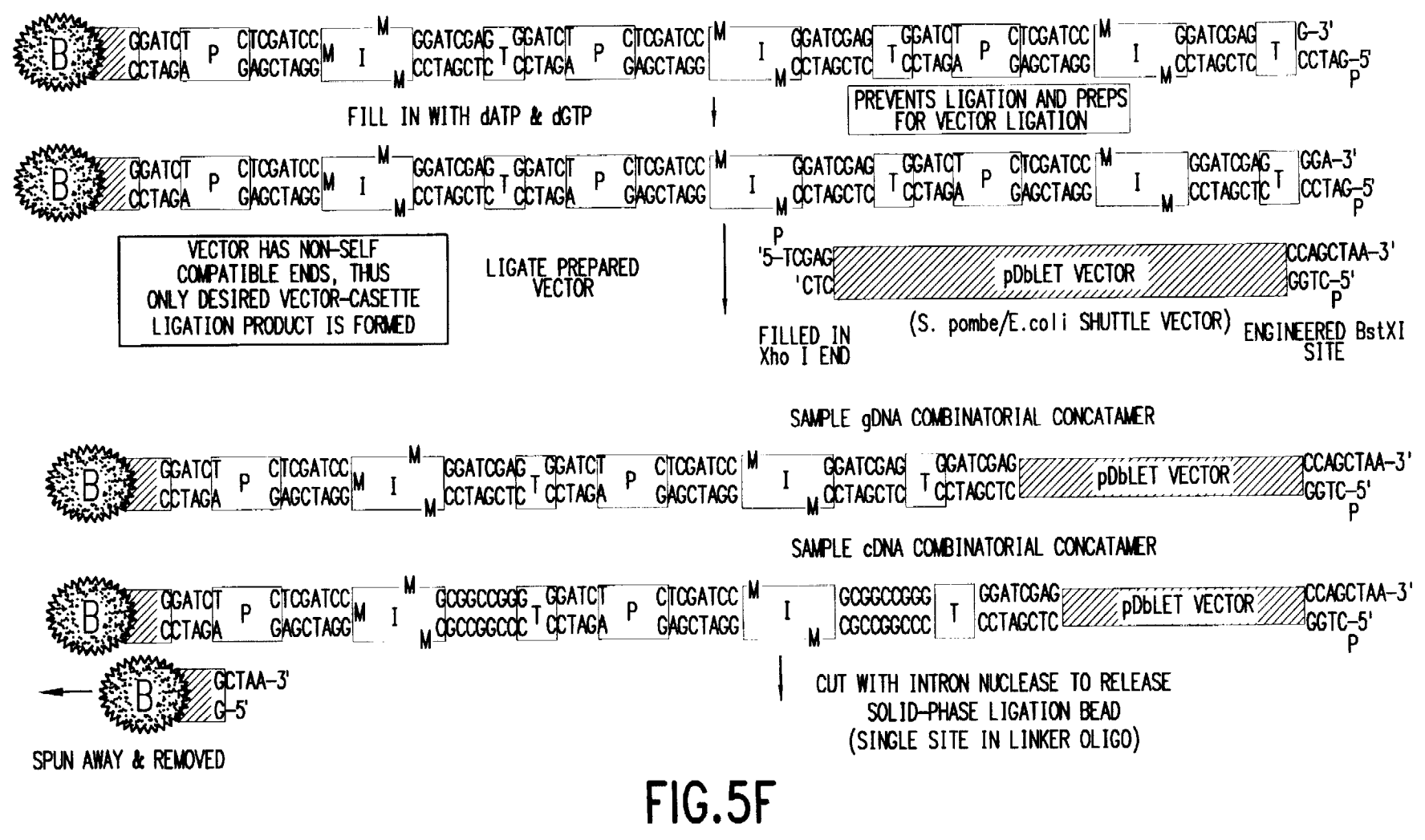

FIGS. 5A-5G Cloning strategy for combinatorial chimeric pathway expression library. FIG. 5A (SEQ ID NOS: 5-14) shows the steps in preparing promoter and terminator fragments for directional cloning of cDNA and genomic DNA inserts. FIG. 5B (SEQ ID NOS: 15-19) shows the steps in preparing promoter and terminator fragments for ligation to genomic DNA inserts. FIG. 5C (SEQ ID NOS: 20-24) shows the steps in preparing cDNA inserts for directional cloning, assembly of gene cassettes, and attachment to solid support. FIG. 5D (SEQ ID NOS: 25-29)shows the steps in preparing genomic DNA inserts for cloning, assembly of gene cassettes and attachment to solid support. FIGS. 5E, 5F and 5G (SEQ ID NOS: 30-40), (SEQ ID NOS: 41-47) show the serial ligation and deprotection of gene cassettes to form a concatemer, the ligation of the concatemer to an *S. pombe/E. coli* shuttle vector (pDblet), release of the expression construct from the solid support and circularization of the expression construct.

FIGS. 6A-6B Vectors useful for preparing combinatorial gene expression libraries. FIG. 6A shows a map of Streptocos. The cosmid vector Streptocos contains a unique BamHI site flanked by T3 and T7 promoters in the multiple cloning site, the origin of replication and thiostrepton resistance gene from pIJ 699, a ColE1 origin (ori), an ampicillin gene (Amp) and two cos sites. FIG. 6B shows a map of modified pDblet. The plasmid pDblet is modified in the multiple cloning site (MCS), and contains a ColE1 origin of replication, an ampicillin gene (Ap$^R$), two copies of autonomous replicating sequence (ARS), an ura4 marker, and the β-galactosidease gene (LacZ). A: AatII; B: BamHI N: NdeI.

Figure 9A:
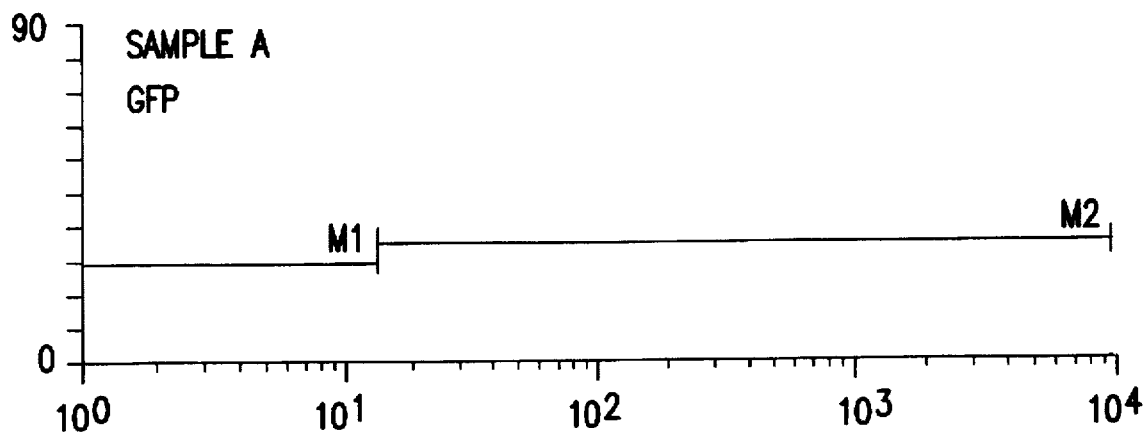
Figure 9B:
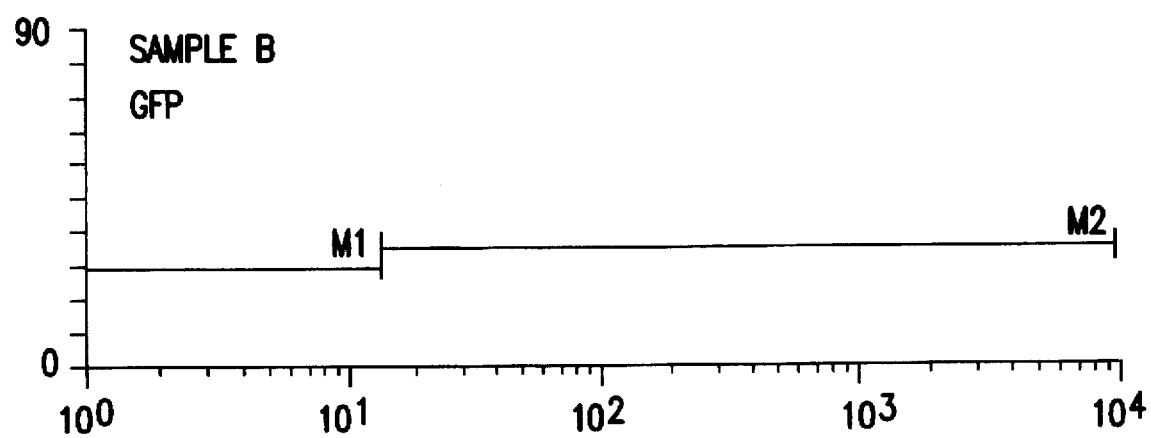

FIGS. 9A and 9B provides an example of FACS sorting of a pool of *E. coli* cells, with and without the presence of expression constructs comprising marine bacterial genes. *E. coli*, strain XL1-MR containing the chemoresponsive construct pERD-20-GFP, referred to as XL1-GFP was infected with a cosmid library of marine bacterial genes. The XL1-GFP cells with or without the marine bacteria genes were cultured for 12 hours at 30° C., and subjected to two cycles of FACS sorting. FIG. 9A: XL1-GFP with marine bacterial genes; FIG. 9B: control XL1-GFP cells.

FIG. 10 (SEQ ID NOS: 50-51) shows an alignment of the amino acid sequence of actinorhodin dehydrase of *Streptomyces coelicolor*, and the predicted partial amino acid sequence derived from CXC-AMN20. Plain boxes indicate sequence identity, and shaded boxes indicate conservative sequence homology.

Figure 11:
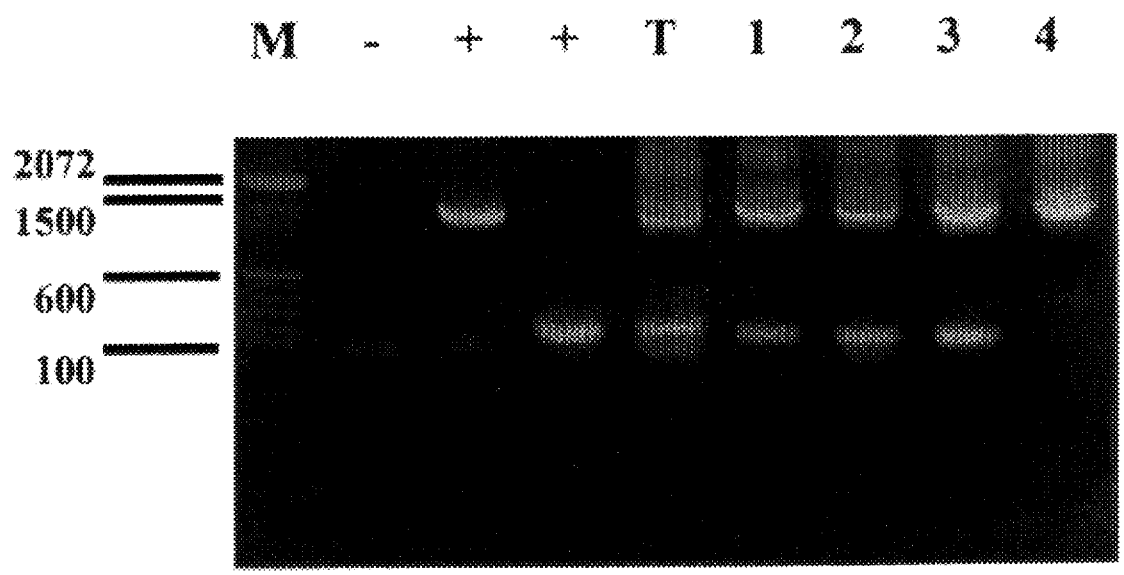

FIG. 11 PCR detection of clone CXC-AMN20 sequences in pools of genomic DNA of marine bacteria. The figure shows a stained agarose gel containing PCR amplicons derived from marine bacteria genomic DNA. M: molecular weight markers, sizes in bp. –: negative control. +: positive controls for the amplicon and for ribosomal RNA. The lanes contain amplicons derived from T: genomic DNA from all 37 species of marine bacteria; 1, 2, 3, 4: pools of genomic DNA of marine bacteria.

Figure 12A:
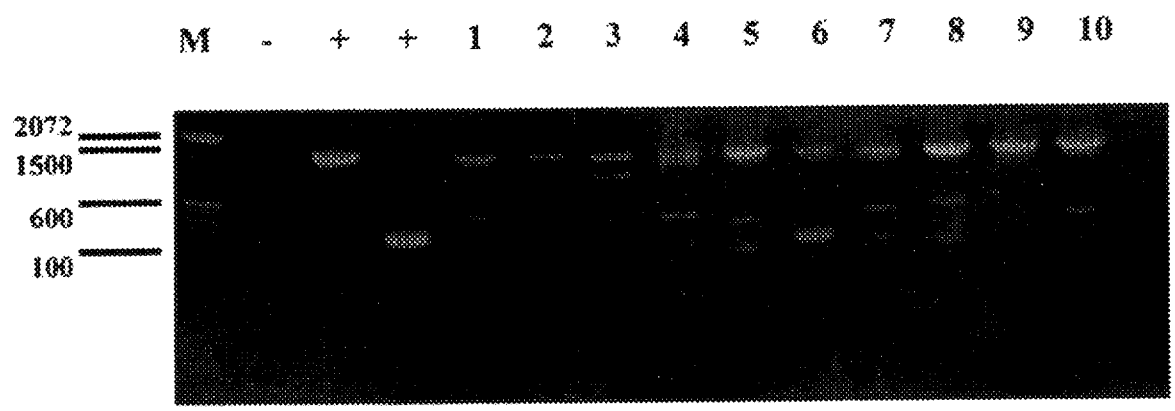
Figure 12B:
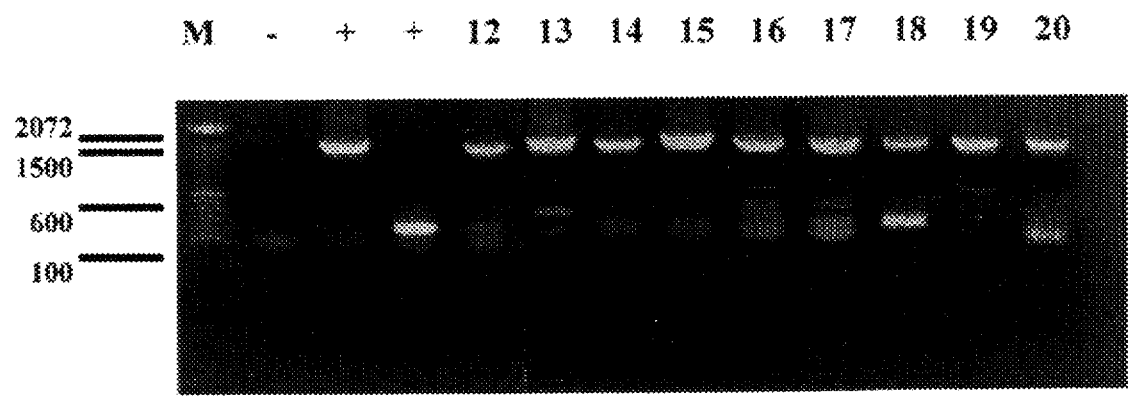
Figure 12C:
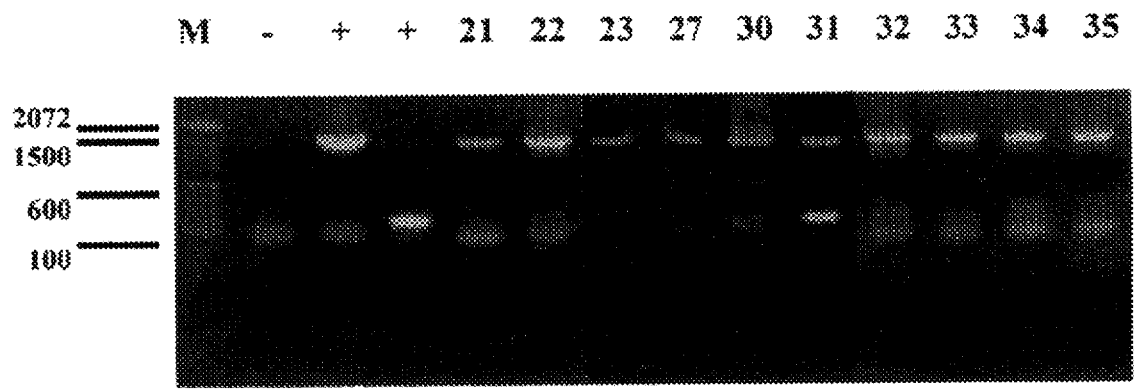

FIGS. 12A-C PCR detection of clone CXC-AMN20 sequences in genomic DNA of marine bacteria species. The figures show stained agarose gels containing PCR amplicons derived from genomic DNA of individual species of marine bacteria. M: molecular weight markers, sizes in bp. –: negative control. +: positive controls for the amplicon and for ribosomal RNA. The lanes contain amplicons derived from genomic DNA of marine bacteria: species #1–10, #12–20 and #21–35 in pool 1, 2 and 3 respectively.

Figure 13:
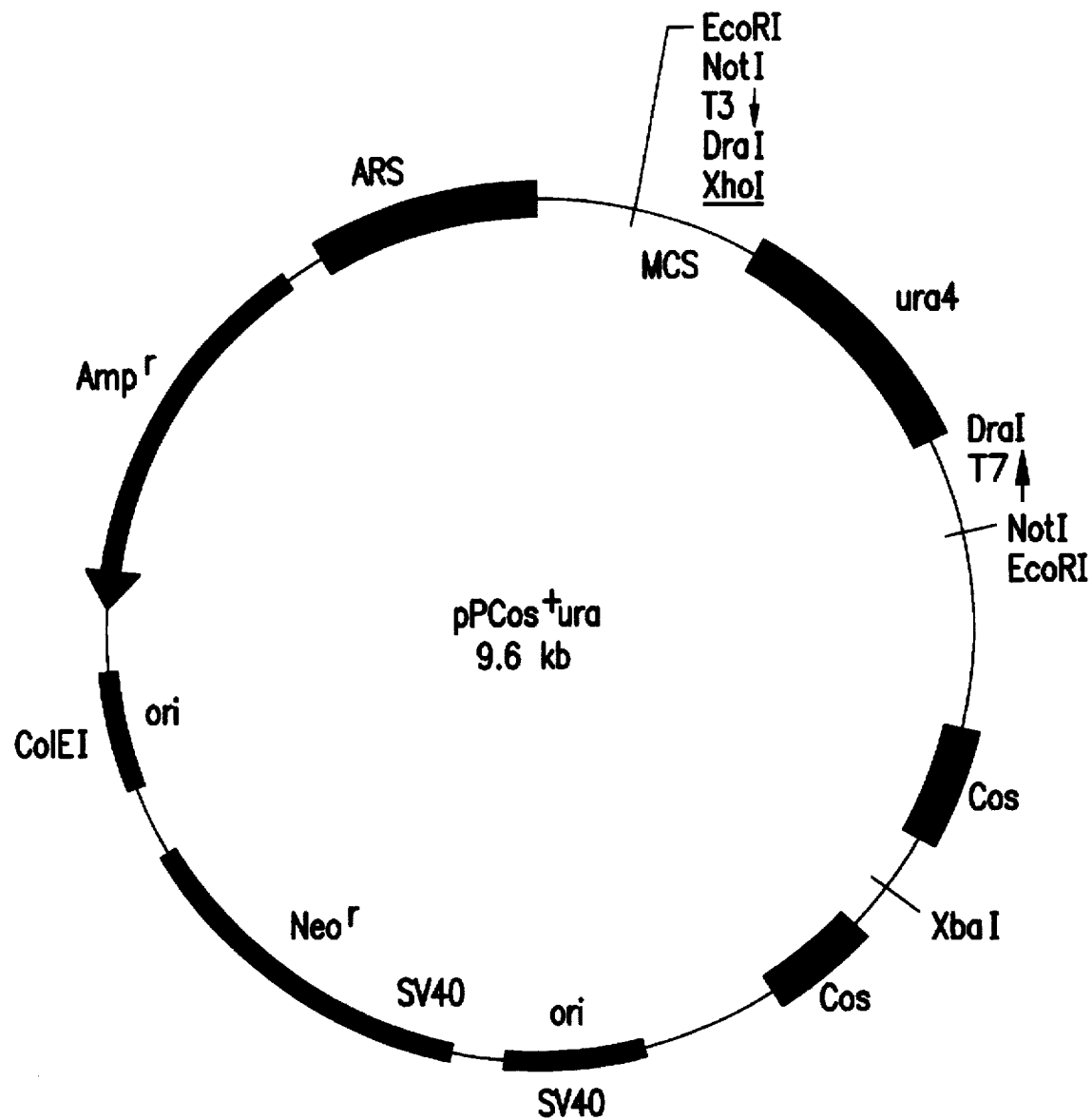

FIG. 13 pPCos+ura. The figure shows the key elements of the 9.6 kb *S. pombe/E. coli* cosmid vector pPCos+ura: multiple cloning site (MCS), yeast selection marker (ura4), cos sites for packaging in λ phage (cos), SV40 origin of replication (SV40 ori), neomycin resistance gene (Neo$^R$), ColE1 origin of replication (ColE1 ori), ampicillin resistance gene (Amp$^R$) and *S. pombe* autonomously replicating sequence (ARS).

Figure 14:
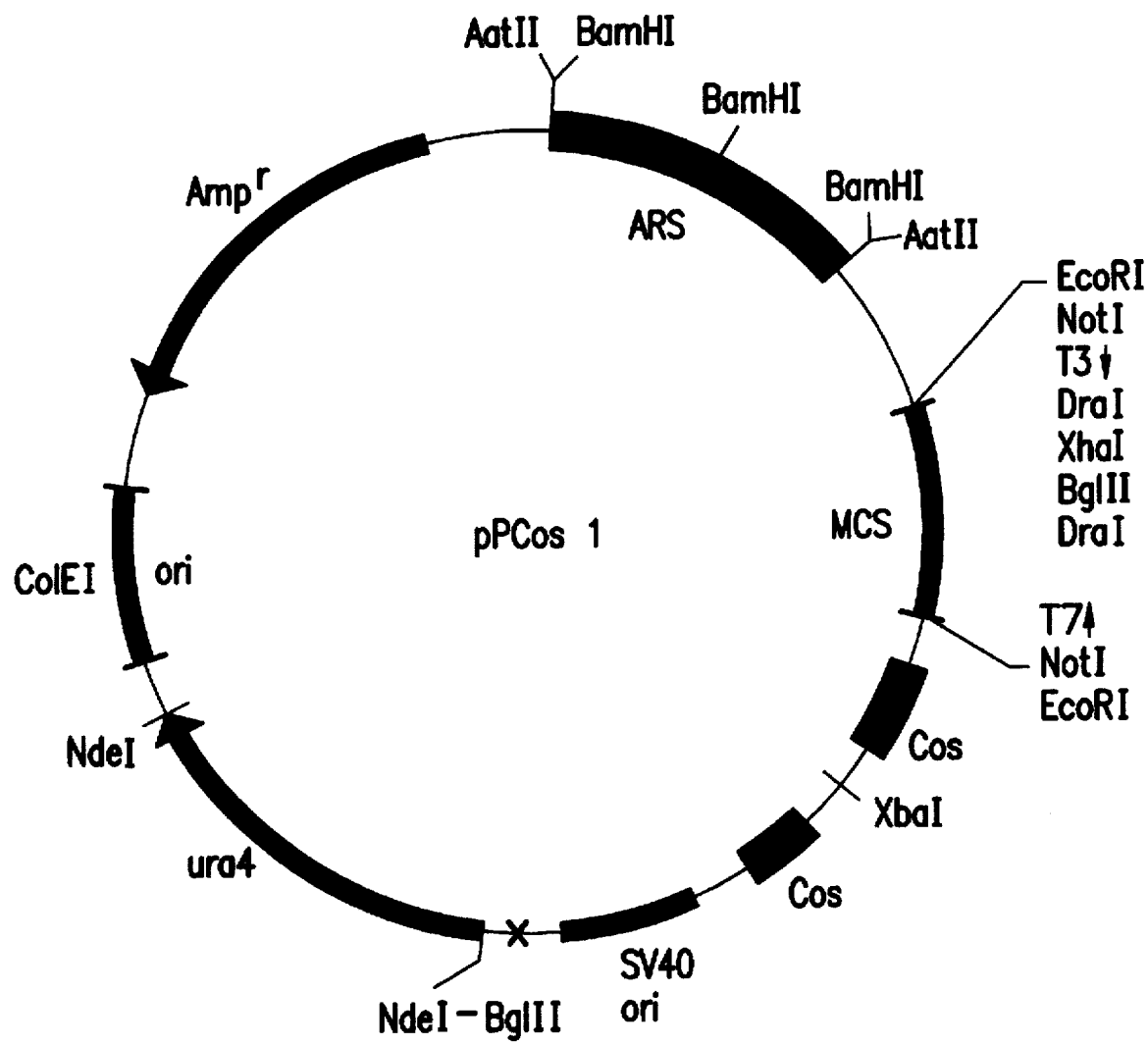

FIG. 14 pPCos1. The figure shows the key elements of the 9.8 kb *S. pombe/E. coli* cosmid vector pPCos1 : multiple cloning site (MCS), yeast selection marker (ura4), cos sites for packaging in λ phage (cos), SV40 origin of replication (SV40 ori), ColE1 origin of replication (ColE1 ori), ampicillin resistance gene (Amp$^R$) and *S. pombe* autonomously replicating sequence (ARS).

5. DETAILED DESCRIPTION OF THE INVENTION

The present invention relates to a drug discovery system that provides methods and compositions for capturing and preserving the diversity of genetic resources in nature, and for translating and expanding the captured genetic resources into diversity of chemical structures. The invention also facilitates screening for desirable activities and compounds.

More particularly, the invention provides methods for constructing and screening combinatorial gene expression libraries. These libraries comprise random assortments of gene products of multiple species which are in some cases allowed to interact with each other in the expression host, and result in some cases in the formation of novel biochemical pathways and/or the production of novel classes of compounds. Moreover, the libraries of the invention provide efficient access to otherwise inaccessible sources of molecular diversity. Some of the libraries of the invention can be transferred from one species of host organism to another species or strain of host organism.

The novel biochemical pathways may carry out processes including but not limited to structural modification of a substance, addition of chemical groups to the substance, or decomposition of the substance.

The novel classes of compound may include but are not limited to metabolites, secondary metabolites, enzymes, or structural components of an organism. A compound of interest may have one or more potential therapeutic properties, including but not limited to antibiotic, antiviral, antitumor, pharmacological or immunomodulating properties or be other commercially-valuable chemicals such as pigments. A compound may serve as an agonist or an antagonist to a class of receptor or a particular receptor.

As used in the present invention, the term "combinatorial gene expression library" encompasses combinatorial natural pathway expression library, combinatorial chimeric pathway expression library as well as host organisms containing the libraries of expression constructs.

A "combinatorial natural pathway expression library" is a library of expression constructs prepared from genetic material derived from one or more species of donor organisms, in which genes present in the genetic material are operably associated with regulatory regions that drives expression of the genes in an appropriate host organism. The combinatorial expression library utilizes host organisms that are capable of producing functional gene products of the donor organisms. The genetic material in each of the host organism encodes naturally-occurring biochemical pathways or portions thereof from one of the donor organisms.

A "combinatorial chimeric pathway expression library" is a library of expression constructs prepared from randomly concatenated genetic material derived from a plurality of species of donor organisms, in which genes present in the genetic material are operably associated with regulatory regions that drives expression of the genes in an appropriate host organism. The host organisms used are capable of producing functional gene products of the donor organisms. Upon expression in the host organism, gene products of the donor organism(s) may interact to form novel chimeric biochemical pathways.

Generally, the methods of the invention comprise providing genetic material derived from one or more donor organism(s), manipulating said genetic material, and introducing said genetic material into a host organism via a cloning or expression vector so that one or more genes of the donor organism(s) are cloned and expressed in the host organism. Such host organisms containing donor genetic material are pooled to form a library. For some libraries, the genetic material can be transferred from one species of host organism to another species or strain of host organism, in which the genetic material can be stably maintained and expressed. Depending on the starting material, choice of host organisms and vectors, any recombinant DNA techniques known in the art can be used in combination and in any order with the techniques and protocols described in section 5.3, 5.4, 5.5, and those used in Examples 6 and 7.

The cloned genetic material, typically comprises a random assortment of genes, the expression of which is driven and controlled by one or more functional regulatory regions. The expression construct or vector may provide some of these regulatory regions. The genes of the donor organism(s) are transcribed, translated and processed in the host organism to produce functional proteins that in turn generate the metabolites of interest.

Figure 1:
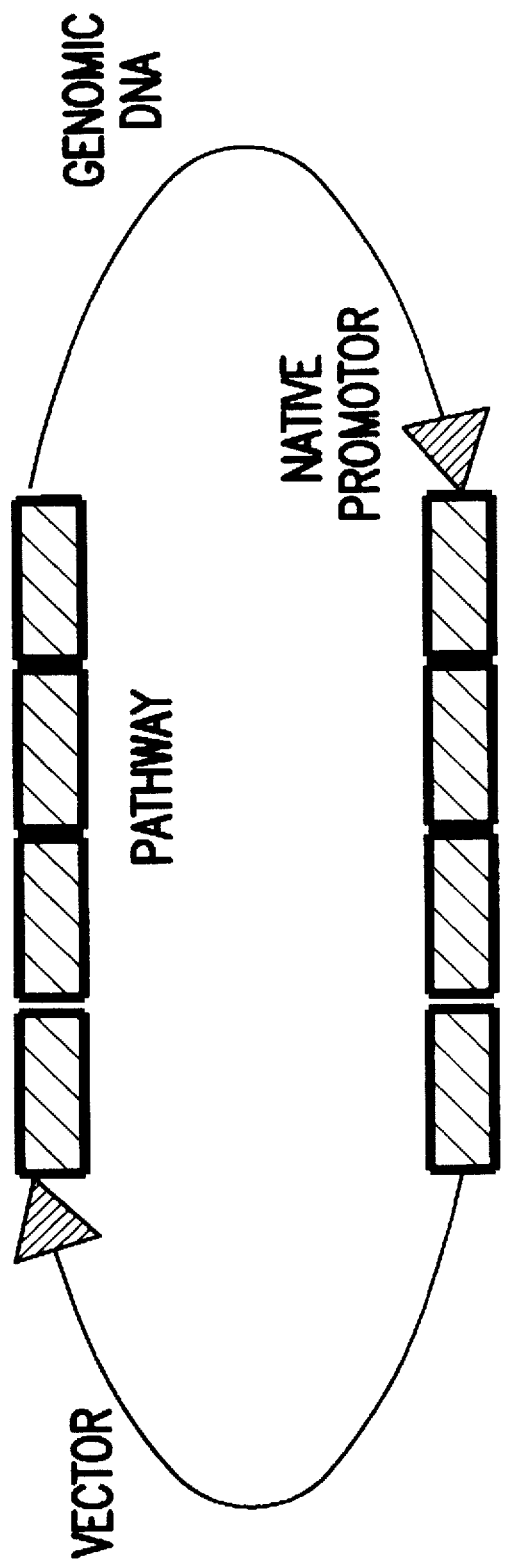

According to the present invention, gene expression libraries comprising complete naturally occurring biochemical pathways or substantial portions thereof can greatly facilitate searches for donor multi-enzyme systems responsible for making compounds or providing activities of interest. Genes that are involved in a particular biochemical pathway can be conveniently isolated and characterized in a single expression construct or clone. A typical arrangement of such an expression construct is shown in FIG. 1.

Once a desirable activity or compound is identified, this convenient feature can greatly facilitate downstream drug development efforts, such as strain improvement and process development. The positive clone can be cultured under standard conditions to produce the desired compound in substantial amounts for further studies or uses. The genes of the biochemical pathway are immediately available for sequencing, mutation, expression, and further rounds of screening. The cloned biochemical pathway is readily amenable to traditional and/or genetic manipulations for overproduction of the desired compound.

Furthermore, biochemical pathways that are otherwise silent or undetectable in the donor organism may be discovered more easily by virtue of their functional reconstitution in the host organism. Since the biochemical characteristics of the host organism are well known, many deviations as a result of expression of donor genetic material can readily be recognized. Novel compounds may be detected by comparing extracts of a host organism containing donor genetic material against a profile of compounds known to be produced by the control host organism under a given set of environmental conditions. Even very low levels of a desirable activity or compound may be detected when the host biochemical and cellular background of the host organism is well characterized. As described in later sections, the present invention provides methods for detecting and isolating clones that produce the desirable activity or class of compounds.

In a preferred embodiment, the methods may be applied to donor organism(s) that cannot be recovered in substantial amounts in nature, or cultured in the laboratory. By cloning genetic material from such organisms into a host organism, the organisms' metabolic pathways can be reproduced, and their products tested efficiently for any desirable properties. Thus, the genetic diversity of these organisms is captured and preserved.

Figure 2:
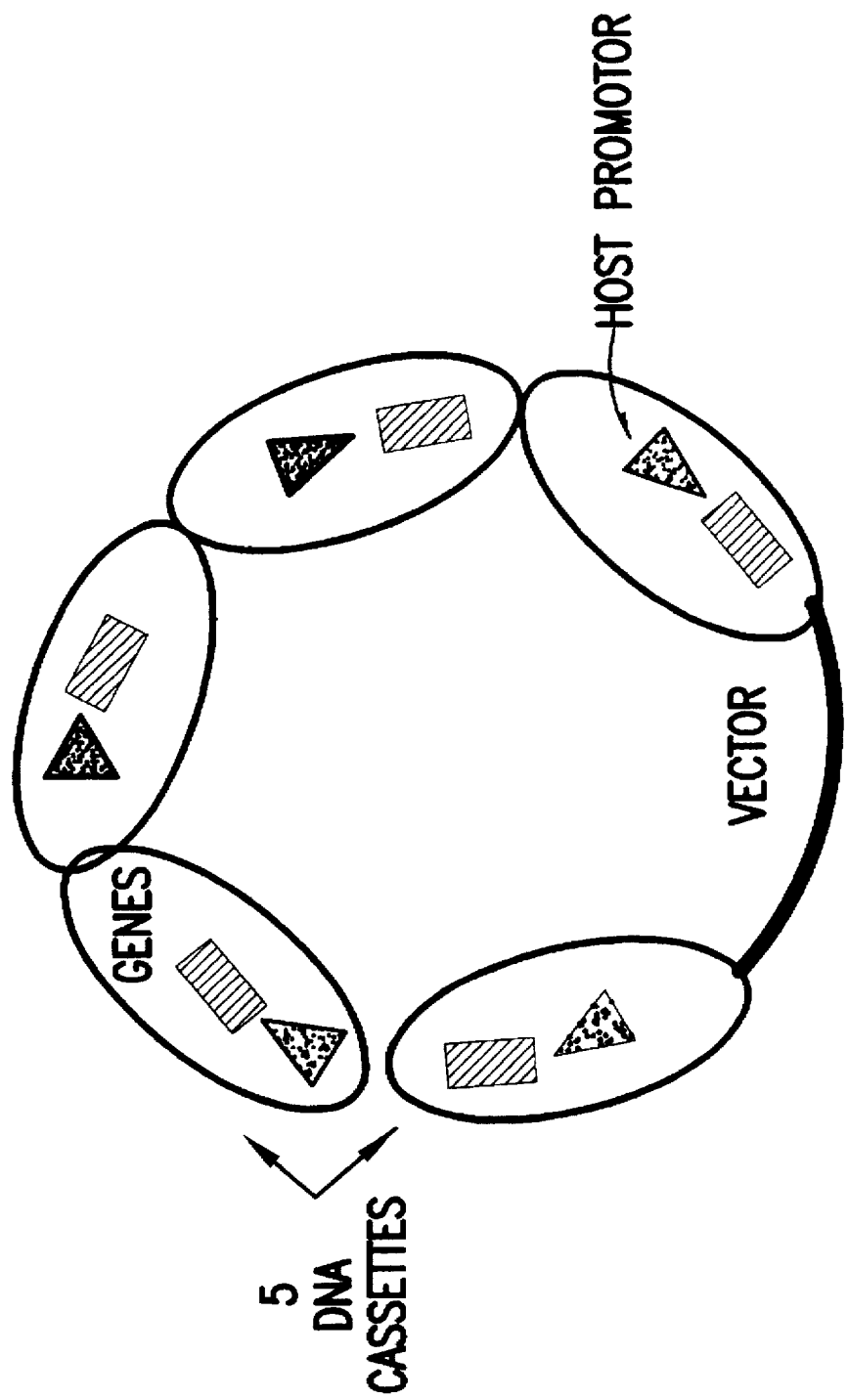

In another embodiment of the invention, a combinatorial chimeric pathway gene expression library can be constructed in which the genetic materials from one or multiple donor organisms are randomly concatenated prior to introduction into the host organism. Thus, each host organism in the library may individually contain a unique, random combination of genes derived from the various donor pathways or organisms. FIG. 2 shows the arrangement of genes and regulatory regions in an expression construct of a combinatorial chimeric pathway gene expression library. For the most part, such combinations of genes in the library do not occur in nature. Upon expression, the functional gene products of the various donor pathways or organisms interact with each other in individual host organisms to generate combinations of biochemical reactions which result in novel chimeric metabolic pathways and/or production of novel compounds. Collectively, the genetic resources of the donor organisms in the library are translated into a diversity of chemical compounds that may not be found in individual donor organisms.

In another aspect of the invention, the species of donor organisms may be selected on the basis of their biological characteristics, or ability to carry out desirable but uncharacterized biochemical reactions that are complementary to the host organism. Such desirable characteristics may include, but are not limited to the capability to utilize certain nutrients, to survive under extreme conditions, to derivatize a chemical structure, and the ability to break down or catalyze formation of certain types of chemical linkages. When genes of the donor organism are expressed in the host organism, the donor gene products can modify and/or substitute the functions of host gene products that constitute host metabolic pathways, thereby generating novel hybrid pathways. Novel activities and/or compounds may be produced by hybrid pathways comprising donor and host-derived components. The target metabolic pathway modified by donor gene products may be native to the host organism. Alternatively, the target metabolic pathway may be provided by products of heterologous genes which are endogenous or have been genetically engineered into every host organism prior to or contemporaneous to construction of the gene expression library. Thus, the present invention also embodies constructing and screening gene expression libraries, wherein DNA fragments encoding metabolic pathway of donor organisms are cloned and coexpressed in host organisms containing a target metabolic pathway.

In another embodiment of the invention, the host organism may have an enhanced complement of active drug efflux systems which secretes the compounds of interest into the culture medium, thus reducing the toxicity of the compounds to the host organism. Absorptive material, e.g., neutral resins, may be used during culturing of the host organisms, whereby metabolites produced and secreted by the host organism may be sequestered, thus facilitating recovery of the metabolites.

In order to make the process of screening combinatorial gene expression libraries more efficient, the present invention further provides methods for detecting those host organisms in the library that possess the activity or compound of interest. In one embodiment of the invention, the host organism contains a reporter system that will respond to the presence of an introduced change, such as the presence of the desirable compound or activity, by activating the de novo synthesis of a reporter molecule. In another embodiment, the host organism contains the precursor of a reporter molecule, or a physiological probe, which is converted to the reporter by the presence of the desirable compound or activity. The reporter molecule in the positive clone generates a signal which allows detection of the positive clone in the expression library, as well as its isolation from the other nonproductive clones.

In many respects, the drug discovery system provides significant convenience and time advantage to the various steps of drug development up to clinical trials. The libraries of the invention are compatible with the established multi-well footprint format and robotics for high-throughput screening. The host organisms of the invention are organisms commonly used for genetic manipulation and/or process development. The present invention takes advantage of the fact that such host organisms or production hosts are well-characterized in terms of their biological properties and maintenance requirements. By cloning genetic materials from a donor organism in other more familiar expression systems, the need for difficult culturing conditions for the donor organism is reduced. Thus, the biological activities, the pharmacokinetic and toxic properties of any lead compound discovered in the system of the invention may be studied and optimized more efficiently.

The novel metabolic pathway generated in a positive clone can be delineated by standard techniques in molecular biology. The lead compound may be synthesized by culturing a clone of the drug-producing host organism under standard or empirically determined culture conditions, so that sufficient quantities of the lead compound may be isolated for further analysis and development. There are already high purity manufacturing protocols, such as Good Manufacturing Practice (GMP) established for some of these standard industrial host organisms. Unlike conventional methods of screening natural product sources, less effort is required to adapt the screening and production technologies to the particular requirements of each potential drug-producing organism.

Moreover, once a positive clone has been identified in a screening assay, the sequences in the clone encoding the metabolic pathway or portions thereof can be isolated and used as hybridization probes. Other gene libraries or combinatorial gene expression libraries of the same donor organism, or related organisms may be screened with such probes to isolate related genes in the natural pathaway or other genes in the same operon or combinatorial gene expression consturct. Such sequences may also be reintroduced into and coexpressed in a host organism for making gene expression libraries. The process of screening and expression can be repeated to further increase the genetic and chemical diversity in the combinatorial gene expression libraries.

The present invention also provides specific combinatorial gene expression libraries made according to the methods of the invention from genetic materials of a particular set of donor organisms and/or cell types. Not all organisms or cell types in a set, especially mixed samples, need to be individually identified or characterized to enable preparation of the combinatorial gene expression libraries.

The invention further provides archival or mobilizable combinatorial gene expression libraries in which the genetic material of the donor organisms can be transferred from one species of host organism to another species or strain of host organism. These libraries are particularly useful when genetic material of the donor organism is unique, rare or difficult to prepare, or when it is desirable to obtain expression of the donor genetic material in many different species or strains of host organism. Where the cloning vector contains the appropriate origin(s) of replication and selection mechanism(s), and/or origin(s) of transfer, the genetic material in the library can be transferred, and be stably maintained and expressed in other species or strains of host organism. The transfer can be effected by, for example, isolation of the expression constructs and introducing the constructs into another host organism, by any means, such as but not limited to transformation, transfection, infection or electroporation. Alternatively, the transfer can be effected by bacterial conjugation between appropriate host organisms.

Any combinatorial gene expression library of the invention may be amplified, replicated, and stored. Amplification refers to culturing the initial host organisms containing donor DNA so that multiple clones of the host organisms are produced. Replication refers to picking and growing of individual clones in the library. A combinatorial gene expression library of the invention may be stored and retrieved by any techniques known in the art that is appropriate for the host organism. Thus, the libraries of the invention are an effective means of capturing and preserving the genetic resources of donor organisms, which may be accessed repeatedly in a drug discovery program.

5.1. PREPARATION OF COMBINATORIAL GENE EXPRESSION LIBRARIES 5.1.1. DONOR ORGANISMS

Any organism can be a donor organism for the purpose of preparing a combinatorial gene expression library of the invention. The donor organisms may be obtained from private or public laboratory cultures, or culture deposits, such as the American Type Culture Collection, the International Mycological Institute, or from environmental samples either cultivable or uncultivable.

The donor organism(s) may have been a traditional source of drug leads, such as terrestrial bacteria, fungi and plants. The donor organisms may be transgenic, genetically manipulated or genetically selected strains that have been useful in generating and/or producing drugs.

The donor organism(s) may or may not be cultivable with current state-of-the-art microbiological techniques e.g., the genetic material used to prepare the libraries can be obtained directly from an environmental sample. Since only a minority ($\leq 1\%$) of the microbes found in nature can be cultured in the laboratory, the major advantage of the present invention is that the donor organism does not have to be cultivable to be utilized herein (Torsvik et al. 1990, Appl Env Micro, 56:782-787).

The invention is not limited to the use of microorganisms as donors. Plants produce an enormous range of compounds, some with dramatic activities on both animals and microorganisms, for example, phytoalexins (Abelson 1990, Science 247:513). Some of these compounds are inducible by wounding or elicitors derived from the cell walls of plant pathogens (Cramer et al. 1985, EMBO J. 4:285-289; Cramer et al. 1985, Science 227:1240-1243; Dron et al. 1988, Proc. Natl. Acad. Sci. USA 85:6738-6742). Biologically-active compounds, like taxol, camptothecin, and artemisinin are examples of plant-derived natural products which are undergoing clinical development respectively as anti-tumor and anti-malarial agents. Any plants, especially those with potential medicinal properties, may be desirable donor organisms (Phillipson, 1994, Trans R Soc Trop Med Hyg, 88 Suppl 1:S17-9; Chadwick et al. eds, 1994, in "Ethnobotany and the search for new drugs", Wiley, Chichester, Ciba Foundation Symp 185).

Another source of natural products with potentially useful antimicrobial or pharmacological properties are invertebrates and vertebrates. Some of these compounds serve as chemical defenses against competitors, pathogens and predators. Such compounds may also be used to kill prey or used as a form of communication (Caporale 1995, Proc Natl Acad Sci 92:75-82). In numerous cases, the secondary metabolites are thought to be produced by associated microbes that may be symbiotic (Faulkner et al. 1993, Gazzetta Chimica Italiana, 123:301-307; Bewley et al. 1995, in "An Overview of Symbiosis in Marine Natural Products Chemistry Symposium" in honor of Professor Antonio Gonzalez, La Laguna University, Canary Islands, Sep. 16, 1995, p26 (abstract)).

Organisms known to manipulate biochemical pathways of other organisms in nature are sources of particular interest, e.g. certain plants, such as Cycas, can produce an ecdysonemimic which disrupts the development of certain insects. Such organisms may live in the same ecological niche where they exist as competitors, symbionts, predator and prey, or host and parasite. Thus, it may be advantageous to use genetic materials derived from organisms that interact chemically with others in nature.

Yet another rich source of natural products is marine organisms. For instance, marine microbes produce novel molecular structures, many of which are bioactive, e.g. octalactin A which is a potential anti-cancer agent with a molecular structure not previously seen in terrestrial bacteria (Tapiolas et al. 1991, J Amer Chem Soc, 113:4682-83); and salinamides (Trischman et al. 1994, J Amer Chem Soc 116:757-758) which have potent anti-inflammatory properties. Certain compounds derived from marine microorganisms contain bromine from seawater which renders the compounds highly active because of the chemical reactivity of the incorporated halogen, e.g., marinone (Pathirana et al. 1992, Tetrahedron Lett 33:7663-7666), a product of mixed polyketide and mevalonic acid biosynthetic pathways, which has selective antibiotic activity against gram positive bacteria. There is a vast diversity of marine species which live in a range of habitats, from polar to tropical regions, with different salinities, temperatures and pressures. The unique nature of these habitats is reflected in the distinct genetics and biochemistry of these organisms, and may provide many useful drug leads. See, for example, Fenical et al. 1992, in "Marine Microorganisms; a new biological resource", Adv in Marine Biotechol, Vol. I, Plenum Press, New York.

Environmental samples may be obtained from natural or man-made environments, and may contain a mixture of prokaryotic and eukaryotic organisms, and viruses, some of which may be unidentified. Samples can either be randomly collected or collected from areas that are ecologically stressed, for example, near an industrial effluent. Soil, freshwater or seawater filtrates, deposits around hot springs or thermal vents, and marine or estuarine sediments may be used as sources of donor organisms. Samples may be collected from benthic, pelagic, and intertidal marine sources. Samples may be collected from tropical, subtropical, temperate and other regions. The donor organisms may be thermophilic, halophilic, acidophilic, barophilic, or methanogenic.

It is also preferable to use organisms that are facing the possibility of extinction, such as those plants and microorganisms found in the tropical rain forest. Insofar as such habitats are being destroyed, species are being lost that might yield useful medicines.

Organisms with potential medicinal properties, including algae, lichens, fungi, plants, and animals, may also be collected on the basis of their uses in traditional or ethnic medical practices.

In many aspects, it is desirable that the library is constructed with genetic material derived from donor organisms that are not generally amenable to traditional drug discovery or development technologies. Such donor organisms may have one or more of the following characteristics: (i) the organism cannot be propagated or cultured in the laboratory; (ii) the organism cannot be recovered from nature in amounts sufficient for further experiments; and/or (iii) the organism requires special conditions for production of the desirable compound that are unknown or are not commercially reasonable. The latter characteristics also describe organisms in extant culture collections, where no drug leads may have been detected in conventional screening processes due to inappropriate culture conditions.

For the purpose of constructing an expression library, the donor organisms need not be taxonomically defined or biochemically characterized. Identification or genetic footprinting of a cultivable species or a representative group of species from an environmental sample may be performed depending on the complexity of the sample and the needs of the drug discovery program, such as, for example, a requirement for donor species dereplication.

The donor organisms may be concentrated or cultured in the laboratory or field prior to extraction of their nucleic acids. For preparing cDNAs, specific growth conditions or the presence of certain chemicals in the culture may be required to induce or enhance the transcription of gene products encoding the activities of interest in the donor organisms. Standard growth conditions may be used to culture the organisms if only genomic DNA is required.

Since it is unlikely that all donor organisms in an environmental sample may be propagated at the same rate, if at all under laboratory conditions, some of the donor organisms may overgrow and lead to the loss or dilution of slow-growing organisms. Thus, it may be preferable to prepare nucleic acids directly from donor organisms in an environmental sample without prior culturing in the laboratory. This may be especially useful when attempting to access the secondary metabolites of invertebrates such as marine sponges, where the metabolites are often believed to be produced by the associated symbiotic and uncultivable microbes. Methods for preparing high quality nucleic acids from donor organisms in environmental samples are provided below in Sections 5.1.2.

Donor organisms contemplated by the invention may include, but are not limited to viruses; bacteria; unicellular eukaryotes, such as yeasts and protozoans; algae; fungi; plants; tunicates; bryozoans; worms; echinoderms; insects; mollusks; fishes; amphibians; reptiles; birds; and mammals. Non-limiting examples of donor organisms are listed in Tables I and II.

TABLE I

List of exemplary bacterial and fungal donor organisms (Berdy 1974, Adv Appl Microbiol, 18:309–406; Goodfellow et al. 1989, in "Microbial Products: New Approaches", Cambridge University Press 343–383)

| Group | Genera |
| --- | --- |
| Bacteria | |
| Actinomycetales | Streptomyces, Micromonospora, Norcadia, Actinomadura, Actinoplanes, Streptosporangium, Microbispora, Kitasatosporia |
| Eubacteriales | Azobacterium, Rhizobium, Achromobacterium, Enterobacterium, Brucella, |

TABLE I-continued

List of exemplary bacterial and fungal donor organisms (Berdy 1974, Adv Appl Microbiol, 18:309–406; Goodfellow et al. 1989, in "Microbial Products: New Approaches", Cambridge University Press 343–383)

| Group | Genera |
| --- | --- |
| | Micrococcus, Lactobacillus, Bacillus, Clostridium, Brevibacterium |
| Pseudomonadales | Pseudomonas, Aerobacter, Vibrio, Halobacterium |
| Mycoplasmatales | Mycoplasma |
| Myxobacteriales | Cytophaga, Myxococcus |
| Fungi | |
| Myxothallophytes | Physarum, Fuligo |
| Phycomycetes | Mucor, Phytophtora, Rhizopus |
| Ascomycetes | Aspergillus, Penicillium |
| Basidiomycetes | Coprinus, Phanerochaete |
| Fungi Imperfecti | Acremonium (Cephalosporium), Trochoderma, Helminthosporium, Fusarium, Alternaria, Myrothecium |
| Yeasts | Saccharomyces |

TABLE II

Higher forms of exemplary donor organisms

| Group | Exemplary Genera, Compounds & Properties |
| --- | --- |
| Plants | |
| Algae | *Digenea simplex* (kainic acid, antihelminthic) |
| | *Laminaria anqustata* (laminine, hypotensive) |
| Lichens | *Usnea fasciata* (vulpinicacid, antimicrobial; usnic acid, antitumor) |
| Higher Plants | Catharanthus (*Vinca alkaloids*), Digitalis (cardiac glycosides), Podophyllum (podophyllotoxin) Taxus (taxol), Cephalotaxus (homoharringtonine), Camptotheca (Camptothecin), Artemisia (artemisinin), Coleus (forskolin), Desmodium (K channel agonist) |
| Protozoa | *Ptychodiscus brevis* |
| Dinoflagellates | (brevitoxin, cardiovascular) |
| Insects | Dolomedes ("fishing spider" venoms), Epilachna (mexican bean beetle alkaloids) |
| Bryozoans | *Bugula neritina* (bryostatins, anti cancer) |
| Molluscs | Conus toxins |
| Sponges | *Microciona prolifera* (ectyonin, antimicrobial) *Cryptotethya cryta* (D-arabino furanosides) |
| Corals | Pseudoterogonia species (Pseudoteracins, anti-inflammatory) Erythropodium (erythrolides, anti-inflammatory) |
| Worms | |
| Annelida | *Lumbriconereis heteropa* (nereistoxin, insecticidal) |
| Spinunculida | *Bonellia viridis* (bonellin, neuroactive) |
| Tunicates | *Trididemnum solidum* (didemnin, anti-tumor and anti-viral) *Ecteinascidia turbinata* (ecteinascidins, anti-tumor) |

TABLE II-continued

Higher forms of exemplary donor organisms

| Group | Exemplary Genera, Compounds & Properties |
|---|---|
| Fish | *Eptatretus stoutii* (eptatretin, cardioactive), *Trachinus draco* (proteinaceous toxins, reduce blood pressure, respiration and reduce heart rate) |
| Amphibians | Dendrobatid frogs (batrachotoxins, pumiliotoxins, histrionicotoxins, and other polyamines) |
| Reptiles | Snake venom toxins |
| Birds | histrionicotoxins, modified carotenoids, retinoids and steroids (Goodwin 1984 in "The Biochemistry of the Carotenoids" Vol. II, Chapman and Hall, New York, pp. 160–168) |
| Mammals | *Orinthorhynohus anatinus* (duck-billed platypus venom), modified cantenoids, retinoids and steroids (Goodwin 1984, supra, pp. 173–185; Devlin 1982 in "Textbook of Biochemistry", Wiley, New York, p. 750) |

5.1.2. PREPARATION OF HIGH QUALITY NUCLEIC ACIDS FROM DONOR ORGANISMS

Nucleic acids may be isolated from donor organisms by a variety of methods depending on the type of organisms and the source of the sample. It is important to obtain high quality nucleic acids that are free of nicks, single stranded gaps, and partial denaturation, and are of high molecular weight (especially for genomic DNA cloning), in order to construct gene expression libraries that are fully representative of the genetic information of donor organisms. To prepare high quality nucleic acid, the methods of the invention provide gentle, rapid and complete lysis of donor organisms in the sample, and rapid and complete inactivation of nucleases and other degradative proteins from the organisms. Initial extraction may be carried out in the field to stabilize the nucleic acids in the sample until further isolation steps can be performed in the laboratory Any nucleic acid isolation procedure requires efficient breakage of the donor organism. A number of standard techniques may be used, including freezing in liquid nitrogen, grinding in the presence of glass or other disruptive agents, as well as simple mechanical shearing or enzymatic digestion.

For mixed materials such as soil, or for samples that contain high amounts of tough materials, such as cellulose or chitin (as in filamentous fungi and plants, for instance), freeze-drying may be employed to render the samples fragile, thus making them more amenable to disruption. Such lyophilized materials preserve both enzymatic as well as high molecular weight materials (such as nucleic acids) for long periods (Gurney 1984, in Methods in Molecular Biology, Vol. 2, p 35–42, John M. Walker ed.). Samples may be flash frozen in liquid nitrogen. Samples that are loose, such as soil, can be frozen in fine gauze or nylon mesh. Lyophilization can be carried out on frozen samples under vacuum for a period of 24–72 hours. Freeze-dried samples can be stored desiccated under vacuum at −70° C. Additional steps may be required for preparation of environmental samples, such as concentration of microbial populations (Jacobson et al. 1982, Appl Env Microbiol, 58:2458–2462; Zhou et al. 1996, Appl Env Microbiol, 62:316–322; Somerville et al. 1989, Appl Env Microbiol, 55:548–554).

One principal method of the present invention, though certainly not the only one to be used, is modified from Chirgwin et al. (1979, Biochem 24:5294), Sadler et al. (1992, Curr Genet, 21:409–416) and Foster (1991, Ph.D. thesis, University of California, Santa Barbara). The method uses the strong chaotropic agent, guanidinium isothiocyanate, with 2-mercaptoethanol to denature proteins and inactivate nucleases, followed by purification of the nucleic acid material by cesium chloride gradient centrifugation. The method provided herein differs from Chirgwin's method in that both DNA and RNA are extracted. Also included in the method of the invention is a high speed centrifugation step, and the optional addition of bisbenzimide dye. Depending on the donor organism used, additional steps may include, but are not limited to, treatment with hexadecylpyridinium chloride or cetyltrimethyl ammonium bromide (CTAB) to selectively remove polysaccharides, treatment with polyvinylpyrrolidone for removal of phenolics, and cellulose chromatography for removal of starch and other carbohydrates (Murray & Thompson, 1980, Nuc Acid Res 8: 4321–25).

RNA isolated from donor organisms can be converted into complementary DNA (cDNA) using reverse transcriptase.

Damaged nucleic acid may be difficult to clone resulting in loss of donor organism DNA and low numbers of clones in a library. The problem can be worsened if the host organism is permissive for recombination and lacks effective endogenous DNA repair mechanisms. The present invention also provides that damaged DNA can be repaired in vitro prior to cloning, using enzymatic reactions commonly employed during second strand synthesis of complementary DNA (Sambrook et al. 1989, in "Molecular Cloning" 2nd Edition, section 8). For example, DNA gaps and nicks may be repaired by the Klenow fragment of DNA polymerase, and *E. coli* DNA ligase. Such enzymatic reactions are well known to those skilled in the arts.

When preparing a combinatorial expression library from DNA extracted from environmental samples, the quantity of available DNA is often limited, and is a consideration in the selection of ligation strategy. If the quantity is low after extraction or concatenation (<100 µg), the DNA may be ligated into a high-efficiency cloning system e.g., SuperCos, as described in Section 5.1.3. The inserts in the clones are amplified and are released from the vector by restriction enzyme digestion. Due to the nature of environmental DNA samples, which may contain both prokaryotic and eukaryotic donor organisms, it may be desirable to use multiple host organisms. If sufficient amount of original environmental DNA sample is available, or if the DNA has been amplified, the DNA may be ligated to each of a panel of vectors appropriate for the desired panel of expression host cells. Preferably, the vectors have the capacity to shuttle between two or more expression hosts.

5.1.3. HOST ORGANISMS AND VECTORS

The term "host organism" as used herein broadly encompasses unicellular organisms, such as bacteria, and multicellular organisms, such as plants and animals. Any cell type may be used, including those that have been cultured in vitro or genetically engineered. Any host-vector systems known in the art may be used in the present invention. The use of shuttle vectors that can be replicated and maintained in more than one host organism is advantageous.

Host organisms or host cells may be obtained from private laboratory deposits, public culture collections such as the American Type Culture Collection, or from commercial suppliers. Such host organisms or cells may be further modified by techniques known in the art for specific uses.

According to the invention, it is preferable that the host organism or host cell has been used for expression of heterologous genes, and are reasonably well characterized biochemically, physiologically, and/or genetically. Such host organisms may have been used with traditional genetic strain improvement methods, breeding methods, fermentation processes, and/or recombinant DNA techniques. It is desirable to use host organisms which have been developed for large-scale production processes, and that conditions for growth and for production of secondary metabolites are known.

The host organisms may be cultured under standard conditions of temperature, incubation time, optical density, and media composition corresponding to the nutritional and physiological requirements of the expression host. However, conditions for maintenance and production of a library may be different from those for expression and screening of the library. Modified culture conditions and media may also be used to emulate some nutritional and physiological features of the donor organisms, and to facilitate production of interesting metabolites. For example, chemical precursors of interesting compounds may be provided in the nutritional media to facilitate modifications of those precursors. Any techniques known in the art may be applied to establish the optimal conditions.

The host organism should preferably be deficient in the abilities to undergo homologous recombination and to restrict foreign DNA. The host organism should preferably have a codon usage similar to that of the donor organism. If eukaryotic donor organisms are used, it is preferable that the host organism has the ability to process the donor messenger RNA properly, e.g., splice out introns. Preferred prokaryotic host organisms may include but are not limited to *Escherichia coli, Bacillus subtilis, Streptomyces lividans, Streptomyces coelicolor Pseudomonas aeruginosa, Myxococcus xanthus*. Yeast species such as *Saccharomyces cerevisiae* (baker's yeast), *Schizosaccharomyces pombe* (fission yeast), *Pichia pastoris*, and *Hansenula polymorpha* (methylotropic yeasts) may also be used. *Filamentous ascomycetes*, such as *Neurospora crassa* and *Aspergillus nidulans* may also be used. Plant cells such as those derived from Nicotiana and Arabidopsis are preferred. Preferred mammalian host cells include but are not limited to those derived from humans, monkeys and rodents, such as chinese hamster ovary (CHO) cells, NIH/3T3, COS, 293, VERO, etc (see Kriegler M. in "Gene Transfer and Expression: A Laboratory Manual", New York, Freeman & Co. 1990).

A host organism may be chosen which modifies and processes the expressed gene products in a specific fashion as desirable. Such modifications (e.g., glycosylation) and processing (e.g., cleavage) of protein products may be important for the function of the protein in a biochemical pathway. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper and accurate processing of the primary transcript, glycosylation, and phosphorylation of the gene product may be preferred if the donor organism(s) are eukaryotic.

For example, it has been shown that eukaryotic fungi share much of the same core molecular biology, and that gene exchange is possible between many of the most common fungal species (Gurr et al. 1987, in Gene Structure in Eukaryotic Microbes, Kinghorn ed., p.93; Bennet & Lasure 1992, Gene Manipulations in Fungi, Academic Press, N.Y.).

A preferred example of a eukaryotic host organism is the fission yeast, *Schizosaccharomyces pombe*. First, the molecular biology of *S. pombe* is highly developed and many major culture and purification processes and manipulations are routinely performed. Second, it is unicellular, and thus can easily be cultured, stored, and manipulated in a laboratory setting. Third, and of particular importance for use in expressing mixed eukaryotic DNAs, it is capable of properly splicing and expressing genes of other species of fungi, plants, and mammals. Studies of the splicing and processing of heteronuclear RNA (RNA which contains introns) have indicated that *S. pombe* shares with other fungi and higher metazoans a remarkable similarity of pattern and structure of small nuclear RNA (snRNA) components needed for splicing. Finally, many non-*S. pombe* promoters, some of which derive from mammalian and plant viruses, are capable of driving moderate to high levels of gene expression (Forsburg, 1993, Nuc Acids Res, 21:2955) This feature can allow the shuttling of a fungal DNA/cDNA library to mammalian cell expression hosts such as NIH3T3 (fibroblasts), GT1-7 (neuronal), or other cell types.

A cloning vector or expression vector may be used to introduce donor DNA into a host organism for expression. An expression construct is an expression vector containing donor DNA sequences operably associated with one or more regulatory regions. The regulatory regions may be supplied by the donor DNA or the vector. A variety of vectors may be used which include, but are not limited to, plasmids; cosmids; phagemids; artificial chromosomes, such as yeast artificial chromosomes (YACs), and bacterial artificial chromosomes (BACs, Shizuya et al. 1992, Pro Natl Acad Sci 89: 8794-8797) or modified viruses, but the vector must be compatible with the host organism. Non-limiting examples of useful vectors are λgt11, pWE15, SuperCos1 (Stratagene), pDblet (Brun et al. 25 1995, Gene, 164:173–177), pBluescript (Stratagene), CDM8, pJB8, pYAC3, pYAC4 (see Appendix 5 of Current Protocols in Molecular Biology, 1988, Ed. Ausubel et al., Greene Publish. Assoc. & Wiley Interscience, which is incorporated herein by reference). An exemplary cosmid vector, pPCos+ ura, for cloning and expression in *Schizosaccharomyces pombe* is provided in FIG. 13, and is deposited on Oct. 24, 1996 at the Agricultural Research Service Culture Collection (NRRL) at Agricultural Research Center, U.S. Department of Agriculture, 1815 North University Street, Peoria, Ill. 61604, United States, and is given accession number B21637N.

When the regulatory regions and transcription factors of the host and donor organisms are compatible, donor transcriptional regions will be able to bind host factors, such as RNA polymerase, to effect transcription in the host organism. If the donor and host organisms are not compatible, regulatory regions compatible to the host organism may be attached to the donor DNA fragment in order to ensure expression of the cloned genes.

In cases where the entire operon, including its own translation initiation codon, ribosome binding regions, and adjacent sequences, is inserted into the appropriate cloning or expression vector, no additional control signals may be needed. However, in cases where only a portion of the coding sequence of a gene is inserted, exogenous control signals, including the translation initiation codon (frequently ATG) and adjacent sequences, must be provided. These exogenous regulatory regions and initiation codons can be of a variety of origins, both natural and synthetic. Both constitutive and inducible regulatory regions may be used for expression of the donor DNA. It is desirable to use inducible promoters when the products of the expression library may be toxic. The efficiency of the expression may be enhanced by the inclusion of appropriate transcription enhancer elements, (see Bittner et al. 1987, Methods in Enzymol. 153:516–544).

"Operably-associated" refers to an association in which the regulatory regions and the DNA sequence to be expressed are joined and positioned in such a way as to permit transcription, and ultimately, translation. The precise nature of the regulatory regions needed for gene expression may vary from organism to organism. Generally, a promoter is required which is capable of binding RNA polymerase and promoting the transcription of an operably-associated nucleic acid sequence. Such regulatory regions may include those 5'-non-coding sequences involved with initiation of transcription and translation, such as the TATA box, capping sequence, CAAT sequence, and the like. The non-coding region 3' to the coding sequence may also be retained or replicated for its transcriptional termination regulatory sequences, such as terminators and polyadenylation sites. Two sequences of a nucleic acid molecule are said to be "operably-associated" when they are associated with each other in a manner which either permits both sequences to be transcribed onto the same RNA transcript, or permits an RNA transcript, begun in one sequence to be extended into the second sequence. A polycistronic transcript may thus be produced. Two or more sequences, such as a promoter and any other nucleic acid sequences are operably-associated if transcription commencing in the promoter will produce an RNA transcript of the operably-associated sequences. In order to be "operably-associated", it is not necessary that two sequences be immediately adjacent to one another.

In addition, the expression vector may contain selectable or screenable marker genes for initially isolating, identifying or tracking host organisms that contain donor DNA. Any antibiotic resistance genes, such as but not limited to ampicillin, kanamycin, chloramphenicol, apramycin or gentamycin (Brau et al., 1984, Mol Gen Genet 193:179–187) and hygromycin (Hopwood et al., 1985, Genetic Manipulation of Streptomyces, A Laboratory Manual, The John Innes Foundation, UK) can be used. Universal forward selection based on plasmid stability in a bacterial host, such as the parD/E system (Johnson et al., 1996, J Bacteriol, 178:1420–1429), can also be used, in the absence of antibiotic selection.

The expression vector may also provide unique or conveniently located restriction sites to allow severing and/or rearranging portions of the DNA inserts in an expression construct.

The expression vector may contain sequences that permit maintenance and/or replication of the vector in one or more host organism, or integration of the vector into the host chromosome. Such sequences may include but are not limited to replication origins, autonomously replicating sequences (ARS), centromere DNA, and telomere DNA. It may also be advantageous to include in the expression vector, host organism sequences or homologous sequences, especially those that are actively transcribed in the host. Such sequences may facilitate integration of the expression construct into the host chromosome, especially when they are found in positions flanking the cloning site in the cloning vector The expression construct may be integrated in the host genome or remain episomal in the host organism. As a result, one or more copies of an expression construct may be generated and maintained in a host organism.

Generally, it may be advantageous to use shuttle vectors which can be replicated and maintained in at least two host organisms, such as, for example, bacteria and mammalian cells, bacteria and yeasts, bacteria and plant cells, or gram positive and gram negative bacteria. A shuttle vector of the invention is capable of replicating in different species or strains of host organisms, and may contain one or more origins of replication that determine the range of host organism in which the vector can stably maintain itself, and undergo replication in concert with cell growth. In prokaryotes, for example, if a broad host range plasmid replication origin is present, the shuttle vector will be capable of stable inheritance in a very wide range of bacteria, e.g. the origins of replication of RK2 (Pansegrau et al., 1994, J Mol Biol 239:623–663) or PBBR (Kovach et al., 1994, BioTechniques 16:800–801) are functional in many gram-negative bacteria, such as Pseudomonas, Agrobacterium, Escherichia, and Rhizobium. Many of the bacteria that harbor DNA comprising a broad host range origin of replication are known to produce metabolites of interest. Origin of replication that is functional in a relatively limited range of related hosts can also be used, e.g., the replication origin of pAkijl which functions in four actinomycete genera (J Gen Microbiol 131:2431–2441). Alternatively, a shuttle vector of the invention can comprise two or more replication origins each having a narrowly defined range that permits the vector to be replicated and maintained in the respective hosts, e.g. *E. coli* and Bacillus. Any origin of replication derived from IncP, IncQ or IncW plasmids can be used in a vector of the invention. A bacteriophage origin of replication, e.g., f1 origin of M13 phage, can also be present in the vector. The coliphage origin of replication can facilitate production of single stranded form of the expression constructs useful for various purposes, such as but not limited to transformation, hybridization.

A shuttle vector of the invention may also comprise cisacting sequences derived from naturally-occurring self-transmissible plasmid, which enable the plasmid to transfer themselves from one species or strain of bacteria to another by means of an interspecies conjugative process (Hayman et al. 1993, Plasmid 30: 251–257). Such sequences, known as origins of transfer, are relatively small (e.g., 200–800 bp) and can be inserted into a shuttle vector of the invention to facilitate the transfer of the shuttle vector between different species or strains of host organisms. Conjugation is a natural process whereby large plasmids are transferred between different species or strains of organism via a conjugation tube at fairly high frequency. The mobilization of transfer origin-containging shuttle vector is mediated by a specific set of transfer proteins which can be provided by expression of function integrated in the host chromosome itself or in trans by a Tra helper plasmid (Ditta et al., 1980, Proc. Natl. Acad. Sci. 77:7347–7351; Knauf et al., 1982, Plasmid 8:45–54). Strains of *E. coli* harboring integrated Tra functions, e.g., S17-1, are available from the American Type Culture Collection.

By using a shuttle vector with the appropriate replication origins, transfer origin(s) and selection mechanisms to construct a library, the DNA sequences of the donor organisms in a library may readily be mobilized from one initial species of host organism to a variety of alternative species of host organisms where the donor DNA sequences can be stably maintained, replicated and expressed. Thus, mobilizable gene expression libraries that are constructed with a shuttle vector, and that can be mobilized into multiple host organisms by conjugation are within the scope of the invention.

For instance, a preferred and exemplary expression vector-host organism combination is the cosmid, SuperCos 1 and the *Esherichia coli* strain, XL1-Blue MR, both of which are commercially available from Stratagene (La Jolla, Calif.). The vector accepts through a BamHI cloning site DNA inserts ranging from 30–42 kbp in size, and carries a neomycin resistance marker (neoR) and an SV40 promoter that is used for expression in mammalian cell. The vector also contains an ampicillin resistance gene for selection in prokaryotic cells. The *E. coli* host organism is deficient in certain restriction systems (hsdR, mcrA, mcrCB and mrr), is endonuclease-deficient (endAl), and recombination deficient (recA). The host organism cannot cleave inserted DNA carrying cytosine and/or adenine methylation, which is often present in eukaryotic DNA and cDNA synthesized using methyl-dNTP analogs.

Advantages of this system include the utilization of highly efficient lambda in vitro packaging systems for initially generating a library in restriction minus, recA minus, *E. coli* hosts. Since the quality of source genomic DNA may be lower than that is required for naked DNA transformations, packaged genomic DNA inserts may be protected against degradation. Once inside an *E. coli* host cell, damaged inserts may be repaired by the host's cellular DNA repair mechanisms. The system requires only small amounts of starting genomic DNA (5–10 µg), and size selection may not be required since the packaging system only accepts inserts in a certain size range. The initial library in *E. coli* may be amplified to produce supercoiled cosmid DNA which may be used in high efficiency transformation methods for introduction into other expression host organisms.

Figure 6A:
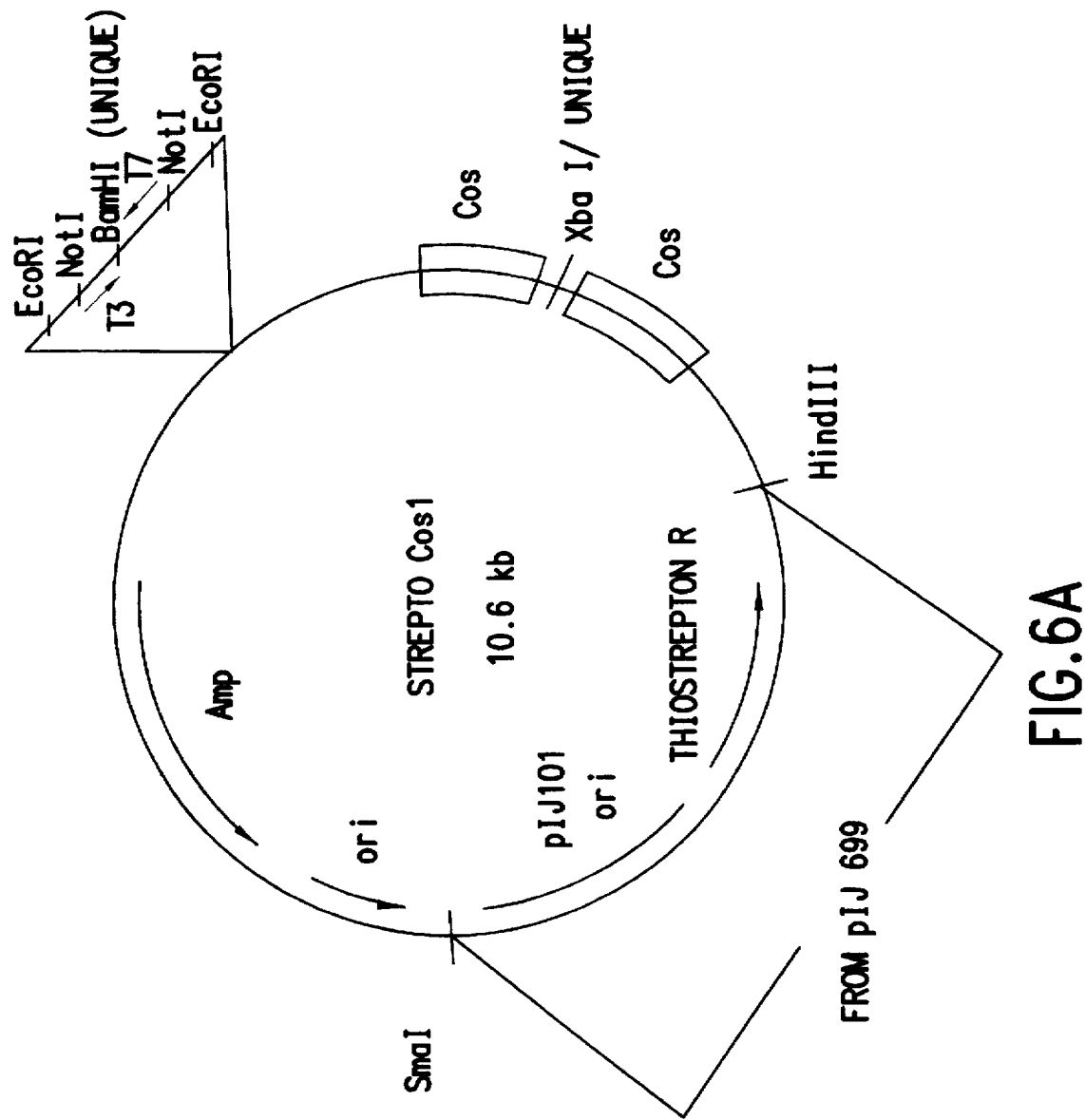
FIG. 6C (SEQ ID NOS: 48-49) shows the oligomer containing an altered BstXI sequence and a NcoI site, which was ligated in excess to SacI/NotI cut pDblet to form modified pDblet.

The SuperCos 1 vector may be further modified for cloning in a Streptomyces host by replacing the SV40 origin of replication and the neoR gene with the Streptomyces origin of replication (e.g., from the plasmid pIJ101 or pIJ922), and the thiostrepton resistance gene. This shuttle vector, termed Streptocos (see FIG. 6A), is constructed by isolation of the 4.0 kb fragment from pIJ699 (Hopwood et al. 1985, Genetic Manipulation of Streptomyces, A Laboratory Manual, The John Innes Foundation) containing the pIJ101 origin and the thiostrepton resistance gene by digestion with KpnI and HindIII. This fragment is blunted at the KpnI site and cloned into SuperCos at the SmaI-HindIII restriction sites (See Bierman 1992, Denis 1992 for related examples). In addition, sequence elements may be introduced for shuttle cosmid mobilization via conjugative transfer (Bierman et al. 1992, Gene 416:43–49). Different Streptocos versions containing Streptomyces-specific promoters may be introduced into the vector adjacent to the BamHI cloning site. By using PCR, Streptomyces promoter fragments may be generated that can be directionally cloned into the NotI/EcoRI sites of SuperCos 1. A variety of known Streptomyces promoters may be used including ermE, Pptr (1995, Mol Microbiol, 17:989) and hrdB (Buttner, M. J. 1989, Mol Microbiol, Vol. 3, pp. 1653–1659). Moreover, one or more replication origin can be engineered into Streptocos to facilitate replication and maintenance of the vector among various Streptomyces/Actinomycete species. For example, the replication origin derived from pSG5 from *Streptomyces ghanaensis* may be used; pSG5-based vectors have been shown to be compatible, and can therefore coexist with origin of replication from other Streptomyces plasmids, such as SCP2*, SLP1.2, pIJ101 and pSVH1 (Muth et al., 1989, Mol Gen Genet 219:341–348). This approach can generally be useful for a wide range of host-vector systems. Accordingly, SuperCos 1 may be modified by introduction of host replication origins, selectable marker genes, and homologous promoters if desired.

Another exemplary vector that can be used in constructing libraries of the invention is pBeloBAC11 which is a modified bacterial artificial chromosome (BAC) based on the plasmid F factor (Shizuya et al., 1992, Proc Natl Acad Sci 89: 8794–8797). The low copy number plasmid vector is capable of handling >300 kb donor DNA and can be maintained stably in *E. coli*. According to the invention, the plasmid PBAC is modified by the introduction of a transfer origin derived from the broad host range plasmid RK2, the replication origin SCP2* from *Streptomyces coelicolor* (Lydiate et al., 1985, Gene 35:223–235), and the apramycin resistance gene.

For combinatorial gene expression libraries using plant cells as hosts, the expression of the donor coding sequence may be driven by any of a number of promoters. For example, preferred strains are described in Principles of Gene Manipulation 1985, R. W. OLD and S. B. Primrose 3rd ed. Blackwell Scientific Pub.; Vectors: A survey of molecular cloning vectors and their uses 1988, R. L. Rodriquez, D. T. Denhardt, Butterworths Pub.; A Practical guide to molecular Cloning 1988, B. Perbal, John Wiley and Sons. viral promoters such as the 35S RNA and 19S RNA promoters of CaMV (Brisson et al. 1984, Nature 310:511–514), or the coat protein promoter of TMV (Takamatsu et al. 1987, EMBO J. 6:307–311) may be used; alternatively, plant promoters such as the small subunit of RuBISCo (Coruzzi et al. 1984, EMBO J. 3:1671–1680; Broglie et al. 1984, Science 224:838–843); or heat shock promoters, e.g., soybean hsp17.5-E or hsp17.3-B (Gurley et al. 1986, Mol. Cell. Biol. 6:559–565) may be used.

Both plant cells and protoplasts may be used as host cells. Plant hosts may include, but are not limited to, those of maize, wheat, rice, soybean, tomato, tobacco, carrots, peanut, potato, sugar beets, sunflower, yam, Arabidopsis, rape seed, and petunia. Plant protoplasts are preferred because of the absence of a cell wall, and their potential to proliferate as cell cultures, and to regenerate into a plant.

In addition, the recombinant constructs may comprise plant-expressible selectable or screenable marker genes which include, but are not limited to, genes that confer antibiotic resistances, (e.g., resistance to kanamycin or hygromycin) or herbicide resistance (e.g., resistance to sulfonylurea, phosphinothricin, or glyphosate). Screenable markers include, but are not be limited to, genes encoding β-glucuronidase (Jefferson, 1987, Plant Molec Biol. Rep 5:387–405), luciferase (Ow et al. 1986, Science 234:856–859), and B protein that regulates anthocyanin pigment production (Goff et al. 1990, EMBO J 9:2517–2522).

To introduce donor organism DNA into plant cells, the *Agrobacterium tumefaciens* system for transforming plants may be used. The proper design and construction of such T-DNA based transformation vectors are well known to those skilled in the art. Such transformations preferably use binary Agrobacterium T-DNA vectors (Bevan, 1984, Nuc. Acid Res. 12:8711–8721), and the co-cultivation procedure (Horsch et al. 1985, Science 227:1229–1231). Generally, the Agrobacterium transformation system is used to engineer dicotyledonous plants (Bevan et al. 1982, Ann. Rev. Genet 16:357–384; Rogers et al. 1986, Methods Enzymol. 118:627–641), but it may also be used to transform as well as transfer DNA to monocotyledonous plants and plant cells. (see Hernalsteen et al. 1984, EMBO J 3:3039–3041 ; Hooykass-Van Slogteren et al. 1984, Nature 311:763–764; Grimsley et al. 1987, Nature 325:1677–1679; Boulton et al. 1989, Plant Mol. Biol. 12:31–40.; Gould et al. 1991, Plant Physiol. 95:426–434).

In other embodiments, various alternative methods for introducing recombinant nucleic acid constructs into plant cells may also be utilized. These other methods are particularly useful where the target is a monocotyledonous plant cell. Alternative gene transfer and transformation methods include, but are not limited to, protoplast transformation through calcium-, polyethylene glycol (PEG)- or electroporation-mediated uptake of naked DNA (see Paszkowski et al., 1984, EMBO J 3:2717–2722, Potrykus et al. 1985, Molec. Gen. Genet. 199:169–177; Fromm et al., 1985, Proc. Nat. Acad. Sci. USA 82:5824–5828; Shimamoto, 1989, Nature 338:274–276) and electroporation of plant tissues (D'Halluin et al., 1992, Plant Cell 4:1495–1505). Additional methods for plant cell transformation include microinjection, silicon carbide mediated DNA uptake (Kaeppler et al., 1990, Plant Cell Reporter 9:415–418), and microprojectile bombardment (see Klein et al., 1988, Proc. Nat. Acad. Sci. USA 85:4305–4309; Gordon-Kamm et al., 1990, Plant Cell 2:603–618).

For general reviews of plant molecular biology techniques see, for example, Weissbach & Weissbach, 1988, Methods for Plant Molecular Biology, Academic Press, N.Y., Section VIII, pp. 421–463; and Grierson & Corey, 1988, Plant Molecular Biology, 2d Ed., Blackie, London, Ch. 7–9.

In an insect system, Autographa californica nuclear polyhydrosis virus (AcNPV) a baculovirus, is used as a vector to express donor genes in Spodoptera frugiperda cells. The donor DNA sequence may be cloned into non-essential regions (for example the polyhedrin gene) of the virus and placed under control of an AcNPV promoter (for example the polyhedrin promoter). These recombinant viruses are then used to infect host cells in which the inserted gene is expressed. (e.g., see Smith et al. 1983, J Virol 46:584; Smith, U.S. Pat. No. 4,215,051).

In yeast, a number of vectors containing constitutive or inducible promoters may be used with Saccharomyces cerevisiae (baker's yeast), Schizosaccharomyces pombe (fission yeast), Pichia pastoris, and Hansenula polymorpha (methylotropic yeasts). For a review see, Current Protocols in Molecular Biology, Vol. 2, 1988, Ed. Ausubel et al., Greene Publish. Assoc. & Wiley Interscience, Ch. 13; Grant et al. 1987, Expression and Secretion Vectors for Yeast, in Methods in Enzymology, Eds. Wu & Grossman, 1987, Acad. Press, N.Y., Vol. 153, pp. 516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathern et al., Cold Spring Harbor Press, Vols. I and II. An exemplary vector, pDblet (Brun et al. 1995, Gene, 164:173–177), that can shuttle between E. coli and S. pombe, and modification of the vector is described in section 5.5.7.

The invention also provides a series of S. pombe/E.coli cosmid vectors, e.g., pPCos+ura (FIG. 13), pPCos1 (FIG. 14) that contain a multiple cloning site, a ColE1 origin and the ampicillin resistance gene respectively for replication and selection in E. coli, an autonomously replicating sequence (ARS) and the ura4 gene for maintenance and selection in S. pombe, an SV40 origin, and dual cos sites for in vitro packaging in λ phage. The construction of pPCos+ura and pPCos1 is described in section 5.5.7.

In mammalian host cells, a variety of mammalian expression vectors are commercially available. In addition, a number of viral-based expression systems may be utilized. In cases where an adenovirus is used as an expression vector, the donor DNA sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing heterologous products in infected hosts. (e.g., See Logan & Shenk, 1984, Proc. Natl. Acad. Sci. (USA) 81:3655–3659). The Epstein-Barr virus (EBV) origin (OriP) and EBNA-1 as a transacting replication factor has been used to create shuttle episomal cloning vectors, e.g., EBO-pCD (Spickofsky et al. 1990, DNA Prot Eng Tech 2:14–18). Viral vectors based on retroviruses may also be used (Morgenstern et al. 1989, Ann Rev Neurosci, 12:47–65). Alternatively, the vaccinia 7.5K promoter may be used. (See, e.g., Mackett et al. 1982, Proc. Natl. Acad. Sci. (USA) 79:7415–7419; Mackett et al. 1984, J. Virol. 49:857–864; Panicali et al. 1982, Proc. Natl. Acad. Sci. 79:4927–4931).

A number of selection systems may be used for mammalian cells, including but not limited to the Herpes simplex virus thymidine kinase (Wigler, et al. 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al. 1980, Cell 22:817) genes can be employed in tk⁻, hgprt⁻ or aprt⁻ cells, respectively. Also, antimetabolite resistance can be used as the basis of selection for dihydrofolate reductase (dhfr), which confers resistance to methotrexate (Wigler, et al. 1980, Natl. Acad. Sci. USA 77:3567; O'Hare, et al. 1981, Proc. Natl. Acad. Sci. USA 78:1527); gpt, which confers resistance to mycophenolic acid (Mulligan & Berg, 1981), Proc. Natl. Acad. Sci. USA 78:2072); neomycin phosphotransferase (neo) which confers resistance to the aminoglycoside G-418 (Colberre-Garapin, et al. 1981, J. Mol. Biol. 150:1); and hygromycin phosphotransferase (hyg), which confers resistance to hygromycin (Santerre, et al. 1984, Gene 30:147).

The present invention also provides specific modifications of host organisms that improve the performance of the combinatorial gene expression libraries. When the libraries are used for the purpose of generating secondary metabolites, the toxicity of the compounds can lead to under-representation of these productive host organisms in the library. In one embodiment of the invention, the host organism may be modified so that the growth and survival of the host organism is less adversely affected by the production of compounds of interest. The increased tolerance can reduce the loss of host organisms that are producing potent drugs at the screening stage as well as the production stage.

One preferred modification of the host organism is the introduction into and/or over-production of active drug efflux systems in the host organism. Membrane-associated energy driven efflux plays a major role in drug resistance in most organisms, including bacteria, yeasts, and mammalian cells (Nikaido 1994, Science 264:382–388; Balzi et al. 1994, Biochim Biophys Acta 1187:152–162; Gottesman et al. 1993, Ann Rev Biochem 62:385). A modified host organism having an enhanced complement of efflux systems can actively secrete a broader range of potentially toxic compounds, thus reducing their accumulation inside the host organism. Negative feedback mechanisms, such as end-product inhibition of the metabolic pathway producing the compounds, may be avoided. Moreover, the isolation of the compounds may be made more efficient since the compounds of interest do not accumulate inside the host organisms.

In bacteria, a large number of efflux systems have been studied which can pump out a wide variety of structurally unrelated molecules ranging from, for example, polyketide antibiotics (acrAE genes of *E. coli*, Ma et al. 1993, J Bacteriol 175:6299–6313), fluroquinolines and ethidium bromide (bmr of *Bacillus subtilis* and nor A of *Staphylococcus aureus*, Neyfakh et al. 1993, Antimicrob Agents Chemother 37:128–129), doxorubicin (drr of *Streptomyces peucetius*, to quaternary amines (qacE of *Klebsiella aerogenes* and mvrC of *E. coli*). See Table III for a list of non-limiting examples of efflux systems. Any such efflux systems may be used in a prokaryotic host organism.

In yeast, many genes conferring pleiotropic drug resistance encode efflux systems, and may be useful in the present invention. For example, the bfr1+ gene confers brefeldin A resistance to *Schizosaccharomyces pombe*, and the CDR1 gene of *Candida albicans* confers resistance to cyclohexamide and chloramphenicol (Prasad et al. 1995, Curr Genet 27:320–329).

For mammalian cells, the multidrug resistance proteins which belong to the class of ATP-binding pump protein may be used (Juranka et al. 1989, FASEB J. 3:2583–2592; Paulusma et al. 1996, Science 271:1126–1128; Zaman et al. 1994, Proc. Natl Acad Sci. 91:8822–8826; Breuninger et al. 1995, Cancer Res 55:5342–5347, Koepsell EP 0699753). The human mdr1 multiple drug resistance gene has been functionally expressed in *Saccharomyces cerevisiae* (Kuchler et al. 1992, Proc Natl Acad Sci 89:2302–2306). Any other efflux systems may also be used for eukaryotic cells.

TABLE III

List of compounds that are secreted by active drug efflux systems

| chemical class | specific name | efflux systems |
|---|---|---|
| cationic dyes | rhomadamine-6G | bmr |
|  | ethidium bromide |  |
|  | acriflavine | acrAE |
| basic antibiotics | puromycin | bmr |
|  | doxorubicin | drr, mdr |
| hydrophilic antibiotics | novobiocin | acrAE |
|  | macrolide |  |
| hydrophobic antibiotics | beta-lactams |  |
| organic cation | tetraphenyl |  |
|  | phosphonium | bmr |
| uncharged | taxol | mdr |
|  | chloramphenicol | bmr |
| weak acid | nalidixic acid | emr |
|  | mithramycin | mdr |
| zwitterions | fluoroquinolines | bmr |
| detergent | SDS | acrAE |

One or more efflux systems may be introduced, induced or overproduced into a host organism. The genes encoding components of an efflux system may be introduced into in a host organism and expressed using the expression vectors and techniques described above. In some instances, it may be advantageous to use an inducible promoter for expression of the efflux system genes.

5.1.4. COMBINATORIAL NATURAL PATHWAY EXPRESSION LIBRARIES

The present invention relates to the construction and uses of combinatorial gene expression libraries, wherein the host organisms contain genetic material encoding natural biochemical pathways or portions thereof that is derived from a plurality of species of donor organisms, and are capable of producing functional gene products of the donor organisms. Biochemical pathways or portions thereof of the donor organisms are thus functionally reconstituted in individual host organisms of a library. Novel activities and compounds of such biochemical pathways may be more accessible to screening by traditional drug discovery techniques or by methods provided herein.

Either DNA or RNA may be used as starting genetic material for preparing such libraries which may include cDNA libraries, genomic DNA libraries, as well as mixed cDNA/genomic DNA libraries. DNA fragments derived from a plurality of donor organisms, e.g., organisms described in Section 5.1.1, are introduced into a pool of host organisms, such that each host organism in the pool contains a DNA fragment derived from one of the donor organisms.

It may be advantageous if the host organism and the donor organisms share certain genetic features, such as similar GC content of DNA and common RNA splicing mechanisms, or physiological features, such as optimal growth temperature. It may thus be desirable to use a host organism that is phylogenetically closely related to the donor organisms. For instance, a prokaryotic host organism may be more desirable for cloning and expression of operons of other prokaryotes.

Donor organisms that are not amenable to traditional drug discovery or drug development technologies may be preferred. For example, most marine bacteria are poorly characterized and not amenable to conventional terrestrial microbiology protocols. The present invention can simplify the development of production and purification processes.

The fragment of donor DNA that is transferred may comprise coding regions encoding functional proteins of a complete biochemical pathway or portions thereof, as well as natively associated regulatory regions such as promoters and terminators. Optimal results may be obtained by using large prokaryotic genomic DNA fragments which have a greater probability of encoding an entire biochemical pathway. If the native function and organization of the transferred DNA fragment is maintained in the host organism, the genes of the donor organism may be coordinately expressed. Also provided are exogenous regulatory regions that may be attached to the DNA fragments so as to ensure transcription of the transferred genes in the host organism, thereby replacing or supplementing transcription initiated from the native promoters.

Interestingly, many of the genes derived from marine bacteria have been found to utilize the native promoters to express functional proteins in *E. coli*. Thus, genes of marine microorganisms may be expressed even without the need to use exogenous regulatory regions. An exemplary list of marine bacterial genes that uses its native promoter in *E. coli* is provided in Table IV.

TABLE IV

List of marine bacterial genes that use its native promoter in *E. coli*

| Gene(s) | Genus & Species | Reference |
|---|---|---|
| kappa-carrageenase (cgkA) | *Alteromonas carrageenovora*, gram(−) aerobe | Barbeyron et al., 1994, Gene 139:105–109 |
| Na+/H+ antiporter (NhaA) | *Vibrio alginolyticus* | Nakamura et al., 1994, Biochim Biophys Acta 1190:465–468 |
| phosphodiesterase (cpdP) | *Vibrio fischeri*, symbiont | Dunlap et al., 1993, J. Bact. 175(15):4615–4624 |
| chitinase | *Alteromonas* sp., Strain 0-7 | Tsujibo et al., 1993, J. Bact. 175(1):176–181 |
| tributyl tin chloride resistance | *Alteromonas* sp. M-1, gram(−) rod | Fukagawa et al., 1993, Biochem. |

TABLE IV-continued

List of marine bacterial genes that use its native promoter in E. coli

| Gene(s) | Genus & Species | Reference |
|---|---|---|
| dagA-complementing | Alteromonas haloplanktis, gram(−) | Biophys. Res. Comm. 194(2):733–740 MacLeod et al., 1992, Mol. Micro. 6(18):2673–2681 |
| vibriolysin (nprV) | Vibrio proteolyticus, gram(−) | David et al., 1992, Gene 112:107–112 |
| tetracycline resistance | Vibrio salmonicida, aerobe | Sorum et al., 1992, Chemo. 36(3):611–615 |
| melanin synthesis (melA) | Shewanella colwelliana, gram(−) periphyte | Fuqua et al., 1991, Gene 109:131–136 |
| DNA modification cluster | Hyphomonas jannaschiana, thermophile | Danaher et al., 1990, Gene 89:129–133 |

In a preferred embodiment, the method of the invention takes advantage of the way that genes of prokaryotes, such as bacteria, are organized into discrete functionally-related gene clusters in the genome, termed operons. In these clusters, genes encoding components of a biochemical pathway are linked together to common regulatory sequences. Functionally related genes in filamentous fungi (Actinomycetes) are also known to be clustered. Gene clusters for many bacterial and actinomycete, and few eukaryotic fungal, biosynthetic pathways have been isolated and characterized. For example, twelve proteins used to produce the carotenoids zeaxanthin and beta-cryptoxanthin de novo in Erwinia herbicola, can be activated and produced synchronously in the bacterium E. coli (Perry et al. 1986, J. Bacteriol. 168:607–612; Hundle et al. 1991, Photochem and Photobiol 54:1:89–93). In addition, prokaryotic amino acid biosynthetic pathways such as leucine and isoleucine biosynthesis, as well as glucose transfer systems are also contained in discrete clusters. Thus, when prokaryotes are used as donor organisms, it is likely that genes that are functionally related in a biosynthetic pathway would be isolated in one clone.

Donor organisms having compact genomes that contain relatively few non-coding regions are preferred. In many aspects, the donor organisms are bacteria which have a relatively small genome, for example, 4400 kbp in length for E. coli, and 2500–3500 kbp for archaebacteria. The number of independent clones required in a library to achieve a 99% probability of containing all of the sequences of the donor genomes is calculated from the following formula (Clarke et al. 1976, Cell 9:91–99):

$$N = \frac{\ln(1-P)}{\ln(1-f)}$$

Where

N=number of recombinant clones necessary in the library
P=the probability a sequence is represented
f=the fractional proportion of the genome in a single recombinant clone For example, E. coli has approximately 4400 kbp of DNA; a cosmid vector can package approximately 40 kbp of DNA. Following these calculations, the entire genome of E. coli can be expected to be thoroughly represented in as few as 504 clones in a cosmid library. Since a typical DNA library can contain 500,000 independent recombinant clones, one such library can effectively represent the genomes of up to 1,000 different bacterial species having a genome size similar to E. coli. Thus, considerable chemical diversity can be generated and assessed efficiently by screening a gene expression library comprising the diverse genetic material of 1,000 or more species of bacteria.

The procedures described in standard treatises, e.g., Maniatis et al. 1989, Molecular Cloning, 2nd Edition, Cold Spring Harbor Press, New York; and Ausubel et al., Current Protocols in Molecular Biology, Greene Publishing Associates and Wiley Interscience, New York, may be followed to carry out routine molecular biology reactions used in constructing the combinatorial gene expression libraries.

Figure 3:
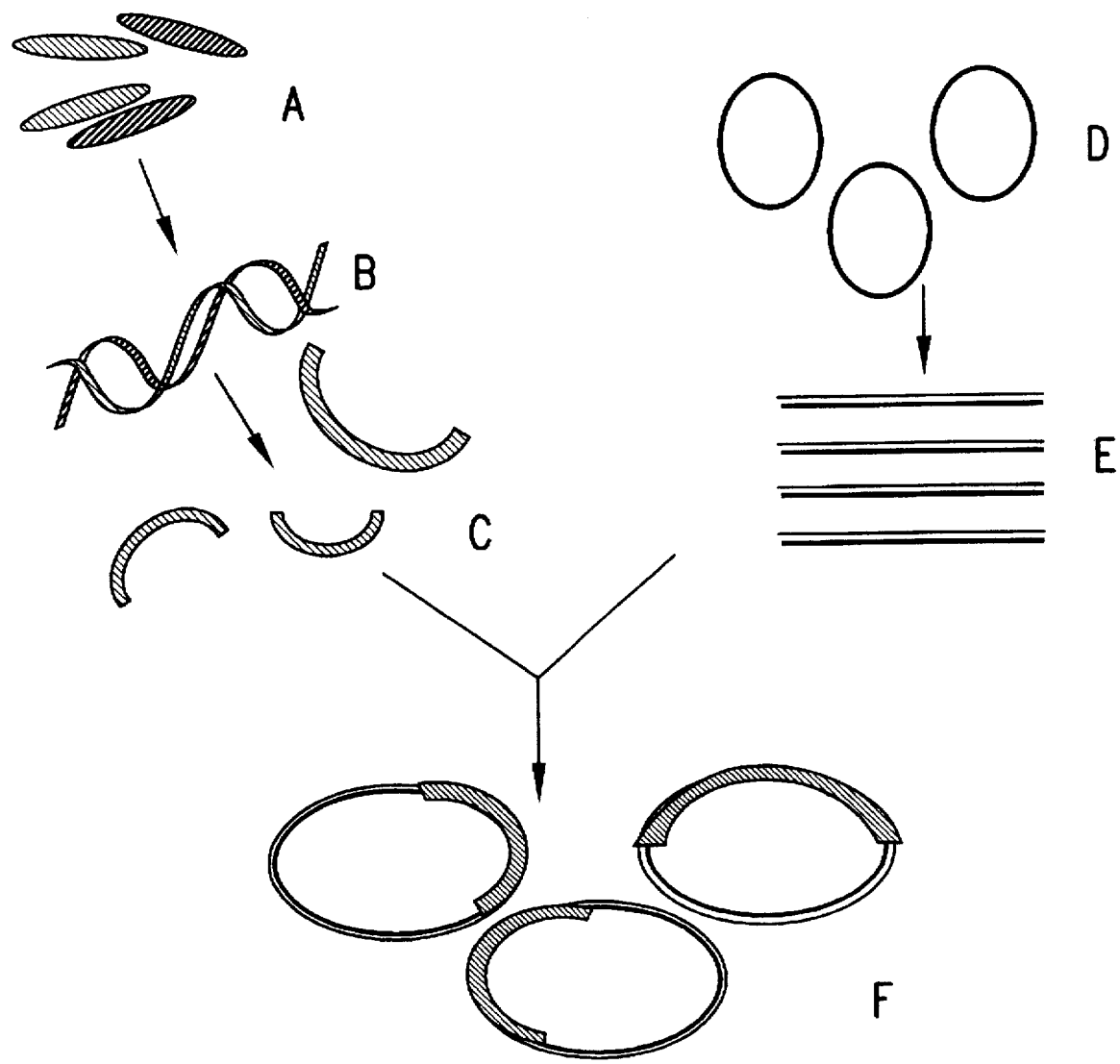

A cloning strategy for combinatorial natural pathway gene expression library is shown in FIG. 3. Any cell from a donor organism can potentially serve as the source of nucleic acid for construction of a gene expression library. Genomic DNA, which includes chromosomal DNA as well as DNA of extrachromosomal genetic elements, such as naturally occurring plasmids, may be used. Alternatively, RNA of a donor organism may be used. RNA, preferably messenger RNA (mRNA), may be extracted, purified and converted to complementary DNA (cDNA) by any technique known in the art. An oligo-(dT) primer or random sequence primers may be used for priming first strand synthesis of cDNA. DNA inserts may optionally be amplified by polymerase chain reaction (PCR).

Genomic DNA and RNA may be extracted and purified by the procedure provided in Section 5.1.2 or by those that are known in the art. For filamentous fungi and bacteria, such procedures may comprise any of several techniques including a) rapid SDS/high salt lysis of protoplasts prepared from young mycelia grown in liquid culture and immediate extraction with equilibrated phenol; b) rapid lysis of protoplasts in guanidinium isothiocyanate followed by ultracentrifugation in a CsCl gradient; or c) isolation of high molecular weight DNA from protoplasts prepared in agarose plugs and pulsed field gel electrophoresis. For bacteria, an alternative procedure of lysis by lysozyme/detergent, incubation with a non-specific protease, followed by a series of phenol/chloroform/isoamyl alcohol extractions may be useful.

For optimal results, large random prokaryotic genomic DNA fragments are preferred for the higher probability of containing a complete operon or substantial portions thereof. The genomic DNA may be cleaved at specific sites using various restriction enzymes. Random large DNA fragments (greater than kbp) may be generated by subjecting genomic DNA to partial digestion with a frequent-cutting restriction enzyme. The amount of genomic DNA required varies depending on the complexity of the genome being used. Alternatively, the DNA may be physically sheared, as for example, by passage through a fine-bore needle, or sonication.

Prior to insertion into a vacant expression vector, such DNA inserts may be separated according to size by standard techniques, including but not limited to, agarose gel electrophoresis, dynamic density gradient centrifugation, and column chromatography. A linear 10–40% sucrose gradient is preferred. The insertion can be accomplished by ligating the DNA fragment into an expression vector which has complementary cohesive termini. The amounts of vector DNA and DNA inserts used in a ligation reaction is dependent on their relative sizes, and may be determined empirically by techniques known in the art. However, if the complementary restriction sites used to fragment the DNA are not present in the expression vector, the ends of the DNA molecules may be enzymatically modified, as for example, to create blunt ends. Alternatively, any site desired may be produced by ligating nucleotide sequences i.e., linkers or adaptors, onto the DNA termini; these ligated linkers or adaptors may comprise specific chemically-synthesized oligonucleotides encoding restriction endonuclease recognition sequences. In an alternative method, the cleaved expression vector and DNA inserts may be modified by homopolymeric tailing.

After ligation of vector DNA to DNA inserts, the expression constructs are introduced into the host organisms. A variety of methods may be used, which include but are not limited to, transformation, transfection, infection, conjugation, protoplast fusion, liposome-mediated transfer, electroporation, microinjection and microprojectile bombardment. In specific embodiments, the introduction of bacteriophage or cosmid DNA into an E. coli host is carried out by in vitro packaging the DNA into bacteriophage particles then allowing these particles to infect E. coli cells. Other naturally-occurring mechanisms of DNA transfer between microorganisms may also be used, e.g., bacterial conjugation.

After the host cells containing expression constructs are pooled to form a library, they can be amplified and/or replicated by techniques known in the art. The purpose of amplification is to provide a library that can be used many times. Amplification may be achieved by plating out the library, allowing the bacteria to grow, and harvesting the phage or bacteria for storage.

Alternatively, the library may be stored in an ordered array. The bulk of the library can be plated out at low density to allow formation of single, discrete plaques or colonies, followed by transfer of individual plaques or colonies into the wells of coded multi-well master plates, e.g., 96-well plates or 384-well plates. The individual clones are allowed to grow in the wells under the appropriate conditions. The coded master plates can be used as an archival source to replicate each clone separately into one or more working plates. Thus, each clone in the library may be handled and assayed individually. The coded archival plates may be sealed and stored for future use. Replication and transfer of the clones may be done with a multi-pin replicator, or multi-channel devices for fluid handling. Preferably, all or most of the transfers and manipulations are performed by laboratory robots (Bentley et al. 1992, Genomics 12:534–541).

The libraries of the invention may be preserved by lyophilization, or cryopreservation in a freezer (at –20° C. to –100° C.) or under liquid nitrogen (–176° C. to –196° C.).

Host organisms containing donor DNA in a library may be identified and selected by a variety of methods depending on the host-vector system used. In one approach, such host organisms are identified and selected upon the presence or absence of marker gene functions, e.g., thymidine kinase activity, resistance to antibiotics, such as kanamycin, ampicillin, bleomycin, or thiostrepton, production of pigment, such as melanin, and resistance to methotrexate. Alternatively, a change in phenotype or metabolism of the host organism, indicated by metabolic testing, foci formation in tissue culture, or occlusion body formation in baculovirus may be used. Once selected for the presence of donor DNA, a series of enzymatic assays or metabolic tests may be carried out on the clones for further characterization.

To characterize the donor DNA inserts in a library of clones containing donor DNA or a portion thereof, mini preparations of DNA and restriction analysis may be performed with a representative set of clones. The results will provide a fingerprint of donor DNA size and restriction patterns that can be compared to the range and extent of insert DNA which is expected of the library.

5.1.5. COMBINATORIAL CHIMERIC PATHWAY EXPRESSION LIBRARIES

The present invention also relates to the construction and uses of combinatorial chimeric pathway expression libraries, wherein the host organisms contain randomly concatenated genetic materials that are derived from one or more species of donor organisms, and are capable of producing functional gene products of the donor organisms. A substantial number of host organisms in the library may contain a random and unique combination of genes derived from one or more species of donor organism(s). Coexpression of the cloned genes may be effected by their respective native regulatory regions or by exogenously supplied regulatory regions. The plurality of gene products derived from the different donor organisms interact in the host organism to generate novel chimeric metabolic pathways and novel compounds. Novel activities and compounds of such chimeric pathways may become more accessible to screening by traditional drug discovery techniques or by methods provided herein.

While not limited to any theory of how novel pathways or compounds are generated in a combinatorial chimeric pathway gene expression library, the coexpression of functional heterologous genes derived from one or a plurality of species of donor organisms enables the gene products to interact in vivo with each other, and with elements of the host organism. Through such interactions, new sets of biochemical reactions will arise, some of which can act in concert to form a chimeric biochemical pathway. The heterologous gene products may encounter substrates, cofactors and signalling molecules that are not present in their respective donor organism. Such substrates, cofactors and signalling molecules may be supplied by the host organism, by other heterologous gene products that are coexpressing in the same host organism, or from the medium.

Moreover, some of the heterologous gene products may be modified structurally, and compartmentalized or localized differently during biosynthesis in the host organism. Some of the heterologous gene products may be exposed to a host cellular environment that is different from that of their respective donors.

It is envisioned that some heterologoiis gene products may also act on the host organism and modify the host cellular environment. Elements of the host cellular environment that may affect, or be affected by, the function of heterologous gene products may include but are not limited to concentrations of salts, trace elements, nutrients, oxygen, metabolites, energy sources, redox states, and pH. Some heterologous gene products may also interact with host gene products which can result in the modification of the host's metabolic pathways.

Depending on the combination of heterologous genes, novel chimeric biochemical pathways and novel classes of compounds that do not exist in nature may be formed in the host organisms of the library. In combinatorial chimeric pathway expression libraries, the genetic resources of the donor organisms are multiplied and expanded to provide a diversity of chemical structure that may not be found in individual organisms. The libraries so prepared may be screened using traditional methods or methods provided by the present invention. Thus, the novel pathways and compounds are made more accessible to drug screening.

Any of the donor organisms described in Section 5.1.1 may be used in preparing a combinatorial chimeric pathway expression library. Donor organisms may be selected on the basis of their known biological properties, or they may be a mixture of known and/or unidentified organisms.

The combinatorial chimeric pathway expression libraries of the invention may be assembled according to the principles described in section 5.1.3. In order to allow the random concatenation of DNA fragments from multiple species of donor organisms, the procedure for library assembly may be modified by including the following steps: generation of smaller genomic DNA fragments, ligation with regulatory sequences such as promoters and terminators to form gene cassettes, and concatenation of the gene cassettes.

Insert DNAs may be complementary DNA (cDNA) derived from mRNA, and/or fragments of genomic DNA, or DNA from an archival or mobilizable combinatorial expression library. The DNA or RNA of different species of donor organisms may be copurified, or they may be isolated separately and then combined in specific proportions. The random mixing of insert DNAs can be done at any stage prior to insertion into the cloning or expression vector. For example, large pieces of DNA from an archival library can be isolated and digested to give smaller fragments, which are then randomly religated to form insert DNAs for a second combinatorial expression library. Other methods for generating and mixing of random fragments of DNA can also be used, for example, in vitro recombination can be used when the DNA fragments share some sequence homologies.

Methylated nucleotides, e.g., 5-methyl-dCTP, may be used in cDNA synthesis to provide protection against enzymatic cleavage, and allow directional cloning of the cDNA inserts in the sense orientation relative to the promoter and terminator fragments.

Random fragments of genomic DNA in the range of 2–7 kbp may be generated by partial digestion with a restriction enzyme having a relatively high frequency of cutting sites, e.g., Sau3AI. Partial digestion is monitored and confirmed by subjecting aliquots of the samples to agarose gel electrophoresis.

Exogenous regulatory regions, such as constitutive or inducible promoters and terminators may be provided to drive expression of the cloned genes. When the host and donor expression systems are not compatible, it is essential to provide such regulatory sequences. PCR may be used to generate various promoter and terminator fragments that are specific to a particular expression host, and have defined restriction sites on their termini. Any method for attachment of a regulatory region to the DNA inserts may be used. Treatment with the Klenow fragment and a partial set of nucleotides, i.e., a partial fill-in reaction, may be used to create insert DNA fragments which will only ligate specifically to promoter and terminator fragments with compatible ends.

The present invention provides a method involving the use of gene cassettes which contains two copies of a promoter, oppositely positioned on either side of a unique restriction site. Any DNA inserted into this restriction site will be transcribed on both strands by the two promoters respectively from both sides.

The present invention also provides an alternative method involving the use of gene cassettes which contain a promoter and a terminator positioned on either side of a DNA insert. If the procedure for directional cloning of cDNA is followed, the 5' ends and 3' ends of the cDNA inserts would have unique matching restriction sites with the 3' ends of the promoter fragments and the 5' ends of the terminator fragments respectively.

Genomic DNA fragments or cDNAs bearing compatible restriction sites at both ends are ligated to the promoters and in some cases, terminator fragments, to form gene cassettes having a mean size of approximately 1–10 kbp.

Concatemers comprising multiple transcription units are assembled by an approach similar to that used in peptide synthesis. A subset of the pool of gene cassettes is bound at one end to a solid phase, e.g., a magnetic bead. The other free end is subjected to several successive cycles of "deprotection" and serial ligation of the remaining pool of transcription units. The solid phase allows separation of the concatemers from the unligated DNA fragments after each addition cycle. When concatenation is completed, the concatemers are released by incubation with a restriction enzyme, such as an intron nuclease, that cleaves a unique and very rare site adjacent to the solid phase to reduce the probability of cleaving the concatenated DNA. Concatenated DNA may then be inserted into a cloning vector to form expression constructs which are introduced into the appropriate host organisms. Alternatively, the constructs may be transformed into an $E.\ coli$ recA minus strain for amplification prior to introduction into the host organisms.

Details of the synthesis of the promoter and terminator fragments, the preparation of gene cassettes, the assembly of the DNA inserts, and the ligation of insert and vector, are provided in Sections 5.4 and 5.5.

Once the combinatorial chimeric pathway expression library is assembled, it can be stored, amplified, replicated, pre-screened and screened essentially in the same manner as described in section 5.1.3. Where the vector contains the appropriate replication origins, transfer origin(s), and/or selection mechanisms, the genetic material in the library can be transferred from one species of host organism to another species or strain for expression.

5.1.6. BIASED COMBINATORIAL EXPRESSION LIBRARIES

In another embodiment of the invention, a biased combinatorial natural or chimeric pathway expression library may be prepared from preselected fragments of DNA that are pooled together from one or more species of donor organisms. Instead of using only the total pooled genomic DNA or cDNA of the donor organism(s), this approach will reduce the number of clones that need to be screened and increase the percentage of clones that will produce compounds of interest. The preselected fragments of DNA contain genes encoding partial or complete biosynthetic pathways, and may be preselected by hybridizing to an initial or archival DNA library a plurality of probes prepared from known genes that may be related to or are involved in producing compounds of interest.

The initial DNA library, preferably a cosmid or bacterial artificial chromosome (BAC) library, and not necessarily an expression library, may contain DNA from one or more species of donor organisms. For further pre-screening, if the initial library is an expression library, DNA in the positive clones may be transferred into and expressed in a host for production, such as $E.\ coli$ or $Streptomyces\ lividans$. More than one initial library may be pre-screened, and DNA from all the positive clones can be pooled and used for making the biased combinatorial gene expression library.

The initial or archival library may be amplified so that DNA of the donor organisms can be pre-screened in a variety of host organisms. In one aspect of the invention, the cloning vector or expression vector can contain the appropriate replication origins and/or transfer origin(s) as described in section 5.1.3, such that the entire initial or archival library can be transferred or mobilized into various compatible host organisms via conjugation. The transfer can also be effected by isolating the donor genetic materials from the archival library and introducing the genetic material into another species or strain of organism by any means, such as but not limited to transformation, transfection and electroporation. For example, once a gene expression library in Streptomyces lividans is generated, it can be introduced into specialized host organisms for expression and screening, such as S. rimosis that produces oxytetracycline, or S. parlus that produces actinomycin D. As another example, an archival library can be constructed in E. coli, and preselected by hybridization with nucleic acid probes to identify genetic materials of interest. The preselected DNA fragments can be isolated from the archival library, then randomly mixed, and cloned into a mobilizable expression vector to form a biased combinatorial expression library. Such a library is enriched for a particular class of metabolic pathway and can be transferred into different host organisms for expression in different biochemical and/or genetic backgrounds.

The probes used for pre-screening may be derived from any cloned biosynthetic pathway, such as the polyketide biosynthetic loci, as these are the best characterized biosynthetic loci and there is considerable sequence conservation between the known clusters, e.g., actI (actinorhodin biosynthesis—Malpartida et al. 1987 Nature 325:818–820), whiE (spore pigment biosynthesis—Blanco et al. 1993 Gene 130:107–16) and eryAI (Donadio et al. 1991 Science 252, 675–679). Similar principles may be applied to other antibiotic or secondary metabolite biosynthetic loci. For example the cloned peptide synthetase genes in low-GC gram positive bacteria, such as Bacillus (Stachelhaus et al. 1995 Science 269: 69–72) and in high-GC gram positive bacteria, such as actinomycetes species that produce thiostrepton, virginiamycin, valinomycin and actinomycin, may have enough sequence similarities to be used as probes to identify new biosynthetic loci in both groups of bacteria. Other cloned biosynthetic pathway, such as peptide synthases and aminoglycoside synthases, can also provide probes for pre-screening the initial libraries.

Alternatively, the initial DNA library may be screened by probes derived from DNA that encode proteins involved in secondary metabolism. Such probes may be prepared by subtracting non-coding DNA and DNA encoding proteins that relate to primary metabolism biosynthetic pathways from total DNA. The remaining DNA is thus biased toward coding regions that encode proteins involved in secondary metabolism. Details of the subtraction procedure are provided in Section 5.3.5.

5.2. SCREENING COMBINATORIAL EXPRESSION LIBRARIES

The drug discovery system of the present invention further encompasses novel methods for screening combinatorial expression libraries. While standard methods of screening expression libraries, such as antibody binding and ligand binding, can also be used with expression libraries of the present invention, the libraries can be adapted to a reporter regimen tailored to identify host organisms that are expressing the desirable pathways and metabolic products.

The methods claimed herein enables the management of large sample numbers with minimal handling to permit efficient and high-throughput detection and isolation of productive clones in the library. The libraries may be pre-screened for a broad range of activities, for the production of a class of compounds or for the presence of relevant DNA sequences. The libraries may also be used directly with a target in both in vivo and in vitro assays. The identified or isolated population of cells may readily be cultured, expanded in numbers, and subjected to further analysis for the production of novel compounds. The genes encoding the metabolic pathway that lead to production of the novel activity or compound may be delineated by characterizing the genetic material that was introduced into the isolated clones. Information on the genes and the pathway, and the clones, will greatly facilitate drug optimization and production.

As used herein, the terms "library clones" or "library cells" refer to host cells or organisms in a combinatorial gene expression library that contain at least one fragment of donor DNA that may encode a donor metabolic pathway or a component thereof. The term "positive clones" or "positive cells" refers to library clones or cells that produce a signal by virtue of the reporter regimen. The term "productive cells" or "productive clones" refers to host cells or organisms in the library that produce an activity or compound of interest, in distinction from the remainder "non-productive cells" in the library.

The term "pre-screen" refers to a general biological or biochemical assay which indicates the presence of an activity, a compound or a gene of interest. The term "screen" refers to a specific therapy-oriented biological or biochemical assay which is directed to a specific disease or clinical condition, and employs a target. The term "target" refers generally to whole cells as well as macromolecules, such as enzymes, to which compounds under test are exposed in a screen. The use of both pre-screens and screens generally embodies visual detection or automated image analysis of a colorigenic indicator, fluorescence detection by fluorescence-activated cells sorting (FACS) or the use of a magnetic cell sorting system (MACS) performed on a population of library cells in the presence of a reporter regimen.

The methods of the invention provide alternative but not mutually exclusive approaches to generation of detectable signal associated with productive cells for the purpose of detecting and isolating these cells of interest. A reporter can be a molecule that enables directly or indirectly the generation of a detectable signal. For example, a reporter may be a light emitting molecule, or a cell surface molecule that may be recognized specifically by other components of the regimen. A reporter regimen comprises a reporter and compositions that enable and support signal generation by the reporter. The reporter regimen may include live indicator cells, or portions thereof. Components of a reporter regimen may be incorporated into the host organisms of the library, or they may be co-encapsulated with individual or pools of library cells in a permeable semi-solid medium to form a discrete unit for screening.

To facilitate detection of compounds of interest as described in the following text, absorptive materials such as neutral resins, e.g., Diaion HP 20 or Amberlite XAD-8 resin, may be added to cultures of library cells (Lam et al. 1995, J Industrial Microbiol 15:453–456). Since many secondary metabolites are hydrophobic molecules, the release or secretion of such metabolites may lead to precipitation on the cell exterior. Inclusion of such resins in the culture causes the sequestration to occur on the resin which may be removed from the culture for elution and screening.

In one embodiment of the invention, the host organisms are engineered to contain a chemoresponsive construct, comprising a gene encoding a reporter molecule operably-associated with a chemoresponsive promoter that responds to the desired class of compounds or metabolites to be screened in the expression library. In the presence of the desirable activity or compound, the chemoresponsive promoter in a positive clone is induced to initiate transcription of the operably-associated reporter gene. The positive cell is identified by detectable signals generated by the expression of the reporter gene.

In an alternative embodiment, a physiological probe can be used which generates a signal in response to a physiological change in individual cells as a result of the presence of a desirable activity or compound. Such a probe may be a precursor of a reporter molecule that is converted directly or indirectly to the reporter molecule by an activity or compound in the biochemical pathway sought. Upon contact with a productive cell, the physiological probe or reporter precursor generates a detectable signal which enables identification and/or isolation of the productive cell. Contact may be effected by direct addition of the probe or precursor to the library cells. Alternatively, contact may be effected by encapsulation and diffusion of the probe or precursor to the library cells during screening.

In yet another embodiment of the invention, indicator cells may be used to signal the production of a desirable activity or compound, thereby enabling identification and/or isolation of productive cells in the library. Whole live or fixed indicator cells, or cellular fractions thereof may be mixed or co-encapsulated with individual or pools of library cells. Indicator cells are selected for their biological properties which is responsive to the presence of the desirable activity or compound. Indicator cells may be the target cells of the desirable compound. Alternatively, indicator cells may be used in conjunction with a reporter to generate a detectable signal.

Pre-screens and screens for each library are chosen after comprehensive characterization of the host organism and, whenever possible, of the donor organisms. Assays in which the host organisms are positive are disqualified, while assays in which the donor organisms are positive are considered acceptable library pre-screens or screens. Substrates are preferably the targets of enzymes relevant to desirable biosynthetic capabilities, may be used to alternatively irrelevant targets (e.g., amylase, β-galactosidase) that indicate the presence of transcriptional and translational activity for the DNA in a specific clone.

In yet another embodiment of the invention, antibiotic resistance may be used as an indicator of production or potential production of interesting secondary metabolites. When library clones are exposed to a panel of antibiotics, resistance to the antibiotics may indicate the presence of a self-defense mechanism, such as efflux pumps which are frequently found adjacent to secondary metabolite biosynthetic pathways as protection against auto-toxicity. Such clones may not exhibit secondary metabolite production at the time of detection, but have increased probability of containing adjacent biosynthetic pathways that can be further manipulated or examined as desired.

The present invention also provides encapsulation as an efficient high-throughput method for growing cells in a confined space, replacing the classic method of growing bacteria in petri dishes. Growing cells in a plate format is both labor- and materials-intensive, while encapsulated cells can be grown easily in a liquid culture with the advantage that dividing cells are kept together, and thus facilitating detection of interesting secondary metabolites. Another advantage of encapsulation is the ability to co-encapsulate components of the reporter regimen and/or other indicator cells with library cells so that pre-screening or screening may be performed in a discrete unit. Encapsulation of cells can be performed easily by means of thermal or ionic gelation using materials such as agarose, alginate or carrageenan.

FACS is a well-known method for separating particles (1–130 μm in size) based on the fluorescent properties of the particles (Kamarch, 1987, Methods Enzymol. 151:150–165). FACS works on the basis of laser excitation of fluorescent moieties in the individual particles. Positive fluorescence results in addition of a small electrical charge to the particle. The change allows electromagnetic separation of positive and negative particles from a mixture. Separated particles may be directly deposited into individual wells of 96-well or 384-well plates.

MACS is a well-known method for separating particles based on their ability to bind magnetic microspheres (0.5–100 μm diameter) (Dynal, 1995). A variety of useful modifications can be performed on the magnetic microspheres, including covalent addition of antibody which specifically recognizes a cell-surface antigen or hapten. Alternatively, for magnetization of encapsulated cells, a reporter regimen can be incorporated into host cells that generate magnetogenic reporter proteins, such as ferritin. In this case, encapsulated cells that generate a positive signal act as magnetic microspheres. The selected microspheres can be physically manipulated by exposure to a magnetic field. For example, the selected microspheres may be sequestered by application of a magnet to the outside of the reaction vessel.

5.2.1. REPORTER CONSTRUCTS

According to the present invention, the host organisms in the library may be engineered to contain a chemoresponsive reporter construct comprising a chemoresponsive promoter operably-associated with a reporter gene. The host organism and/or the construct may contain other genes encoding accessory proteins that are involved in the regulation of transcription from the chemoresponsive promoter or the production of signals.

A chemoresponsive promoter is any double-stranded DNA sequence that is capable of binding an RNA polymerase and initiating or modulating transcription of an operably-associated reporter gene only in the presence of a certain kind of activity or a certain class of compounds. Preferably, the chemoresponsive promoter has no or only a negligible level of constitutive background transcriptional activity in the host organism in the absence of the inducing activity or compound. A chemoresponsive promoter that respond negatively to the presence of an activity or compound by decreasing or ceasing transcriptional activity may also be used.

Promoters useful in the present invention may include, but are not limited to, promoters for metabolic pathways, biodegradative pathways, cytochromes and stress response (Orser et al. 1995, In vitro Toxicol 8:71–85), such as heat shock proteins. For example, the Pm promoter of the Pseudomonas TOL plasmid meta-cleavage pathway and its positive regulator XylS protein which is inducible and modulated by a range of benzoates and halo- or alkylaromatic compounds may be used (Ramos et al. 1988, FEBS Letters 226:241–246; de Lorenzo et al. 1993, Gene 130:41–46; Ramos et al. 1986, Proc Natl Acad Sci 83:8467–8471; Mermod et al. 1986, J. Bateriol 167:447–454). Other non-limiting examples of chemoresponsive promoters are promoters relating to phosphonate utilization (Metcalf et al. 1993, J Bacteriol 175:3430–3442), promoters sensitive to cis-cis-muconate (Rothmel, 1990); promoters sensitive to antibiotics and salicylates (Cohen et al. 1993, J Bacteriol, 175:7856–7862; Cohen et al. 1993, J. Bacteriol, 175:1484–1492), promoters from the arsenic and cadmium operons from *Staphylococcus aureus* (Corbisier et al. 1993, FEMS Letters 110:231–238); sfiA (Quillardet et al.

1982, Proc Natl Acad Sci 79:5971-25 5975), zwf (Orser et al., 1995, supra).

A reporter gene encodes a reporter molecule which is capable of directly or indirectly generating a detectable signal. This includes colorigenic or magnetogenic reporters as well as any light-emitting reporter such as bioluminescent, chemiluminescent or fluorescent proteins may be used, which includes but are not limited to the green fluorescent protein (GFP) of *Victoria aequoria* (Chalfie et al. 1994, Science 263:802-805), a modified GFP with enhanced fluorescence (Heim et al. 1995, Nature 373:663-4), the luciferase (luxAB gene product) of *Vibrio harveyi* (Karp, 1989, Biochim Biophys Acta 1007:84-90; Stewart et al. 1992, J Gen Microbiol, 138:1289-1300), and the luciferase from firefly, *Photinus pyralis* (De Wet et al. 1987, Mol Cell Biol 7:725-737). Any fluorigenic or colorigenic enzymes may be used which includes but are not limited to beta-galactosidase (LacZ, Nolan et al. 1988, Proc Natl Acad Sci USA 85:2603-5 2607), and alkaline phosphatase. Any cell surface antigen may be used, for example, *E. coli* thioredoxin-flagellin fusion protein, i.e., *E. coli* thioredoxin (the trxA gene) expressed as a fusion protein with flagellin (the fliC gene) on the surface of *E. coli* flagellae (Lu et al. 1995, Bio/Technology 13:366-372).

Figures 6B, 6C:
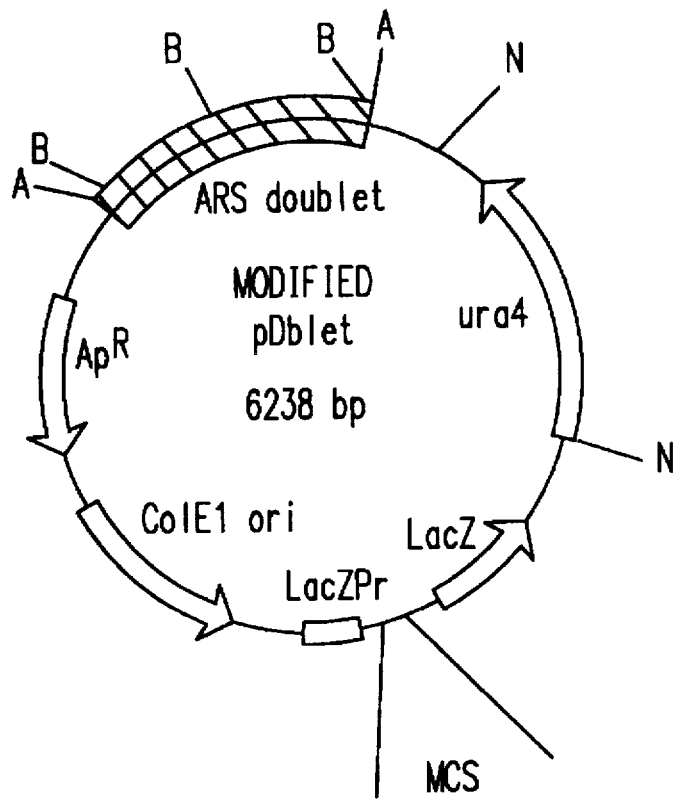
Figure 7:
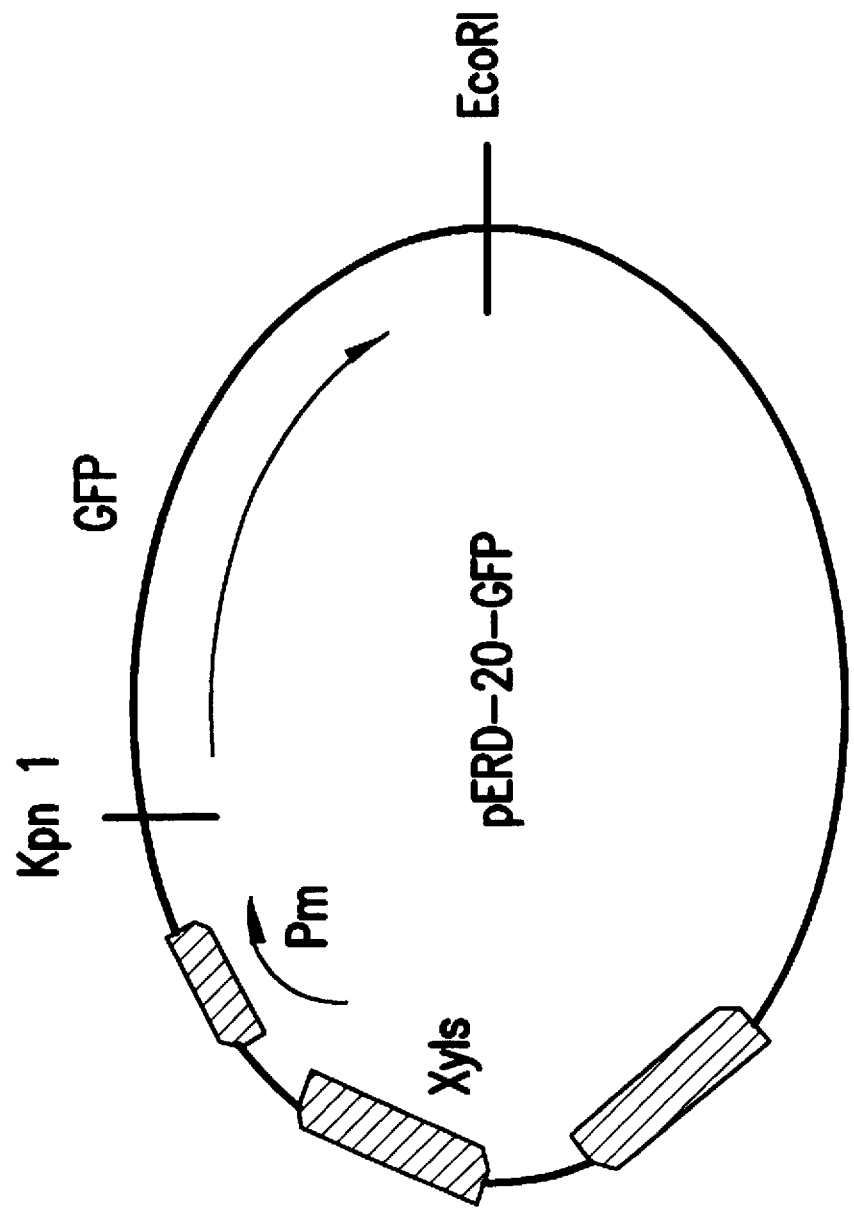
FIG. 7 shows a chemoresponsive construct pERD-20-GFP comprising a reporter gene encoding green fluorescent protein (GFP), a chemoresponsive promoter (Pm) and its associated regulator (XylS).
Figure 8:
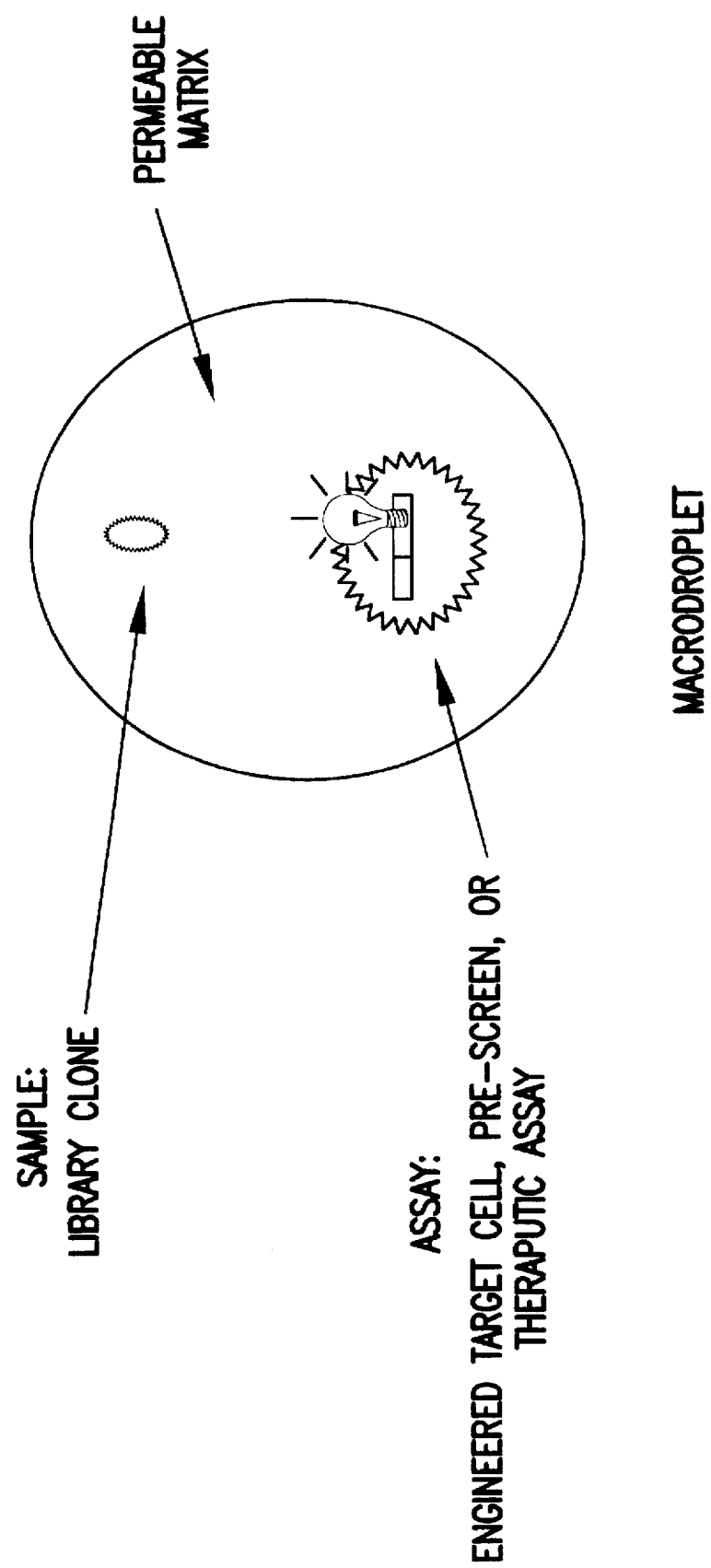
FIG. 8 shows a macrodroplet comprising a permeable matrix, in which is encapsulated a clone from a combinatorial gene expression library, and an indicator cell which contains a reporter regimen.

An exemplary chemoresponsive reporter construct provided herein is pERD-20-GFP which contains the Pm promoter and the XylS gene of Pseudomonas (Ramos et al. 1988, FEBS Letter 226:241-2476) that are responsive to certain classes of benzoates, resulting in transcription and translation (expression) of the reporter, GFP (see FIG. 6).

Different promoter sequences may be generated by PCR and attached to the coding regions of GFP or flagellin-thioredoxin reporter. Genomic and plasmid DNA containing the promoter of interest may be purified from the relevant species using standard DNA purification methods, and resuspended in TE. Primers may be synthesized corresponding to the 5' and 3' boundaries of the promoter regions with additional sequences of restriction sites to facilitate subcloning. The amplification reactions are carried out in a thermocycler under conditions determined to be acceptable for the selected template and primers. The reaction products are separated by agarose gel electrophoresis, and subcloned using the TA Cloning Kit (Invitrogen, La Jolla). The amplified promoter sequences may be recloned into a general purpose cloning vector in a context 5' to the GFP or flagellin-thioredoxin cDNA.

5.2.2. PHYSIOLOGICAL PROBES AND REPORTER PRECURSORS

A physiological probe as used herein is a fluorescent or colorigenic agent which upon contact or entry, generates a signal in response to changes in physiological and/or metabolic parameters of a library cell or indicator cell.

The probe can be an enzyme substrate linked to a fluorogenic agent. For example, a fluorogenic alkyl ether can be incubated with the cells. If the cell is producing polyaromatic hydrocarbons, the hydrocarbons can induce microsomal dealkylases, which in turn cleave the fluorogenic alkyl ether, yielding a fluorescent product.

Fluorescent probes may be selected for detection of changes in the following physiological and metabolic parameters such as, but not limited to, those described in Shechter, et al. (1982, FEBS Letters 139:121-124), and Bronstein et al. (Anal Biochem 219:169-81).

| Metabolic activity | Cause (specific example) | Stain/Substrate (class of chemical) |
|---|---|---|
| Decrease in membrane potential | Stress, injury (isopropanol) | BacLight stain (Semi-permeant nucleic acid stain) |
| Intracellular pH | Physiological changes | BCECF-AM (lipophilic acetoxymethyl ester of phenolic fluor) |
| Increase in cytochrome-mediated oxidation | Induction of microsomal dealkylases by polyaromatic hydrocarbons (naphthalene) | 7-ethoxy-heptadecyl-coumarin (fluorogenic alkyl ether) |

5.2.3. PRE-SCREENING AND SCREENING OF THE LIBRARY

The combinatorial gene expression libraries of the invention may be pre-screened or screened by a variety of methods, including but not limited to, visual inspection, automated image analysis, hybridization to molecular beacon DNA probes (Tyagi et al. 1996, Nature Biotechnol, 14:303-308) fluorescence activated cell sorting (FACS) and magnetic cell sorting (MACS). Screening may be performed on bulk cultures of unamplified or amplified libraries.

In specific embodiments of the invention, individual or pools of library cells are encapsulated in an inert, stable and porous semi-solid matrix in the form of droplets during pre-screening or screening. The semi-solid matrix is permeable to gas, liquid, as well as macromolecules, and permits the growth and division of encapsulated cells. Examples of suitable matrices may include but are not limited to agarose, alginate, and carrageenan. The encapsulated library cells may be cultured and tested in the droplets, and remain viable so that the cells may be recovered from the droplets for further manipulations. The matrix may optionally be exposed to substances, such as an antibiotic, which can select for library cells that contain a selectable marker. The droplets may also be exposed to nutrients to support the growth of library cells. The following examples are offered by way of illustration and are not intended to limit the invention in any manner.

Encapsulation may be performed in one of many ways, producing either macrodroplets (droplets from 0.5 to 2.5 mm) or microdroplets (droplets from to 250 µm) depending upon the method of detection employed during subsequent pre-screening or screening. The size and the composition of the droplets may be controlled during formation of the droplets. Preferably, each macrodroplet or microdroplet will contain one to five library cells.

For example, macrodroplets may be prepared using sodium alginate as follows: sodium alginate is dissolved in 100 mL of sterile water at a concentration of 1% using an overhead mixer at 2000 rpm. A volume of library cells of *E. coli* or yeast, such as *Schizosaccharomyces pombe* and Saccharomyces species; or spores for Streptomyces species; *Bacillus subtilis*; and filamentous fungus such as Aspergillus and Neurospora species; is added to the sodium alginate solution so that 1-5 cells are encapsulated per droplet. The mixture is allowed to sit for at least 30 minutes to degas, and is then extruded through any device that causes the formation of discrete droplets. One such device is a syringe with a 25 gauge needle. The droplets are formed by adding the sodium alginate solution drop-wise into a beaker of gently stirring 135 mM calcium chloride solution Droplets are allowed to solidify for 10 minutes, and are then transferred to a sterile flask where the calcium chloride solution is removed and replaced with a suitable growth media. Encapsulated library cells can be grown under standard conditions.

Microdroplets may be generated by any method or device that produces small droplets, such as but not limited to, two-fluid annular atomizer, an electrostatic droplet generator, a vibrating orifice system, and emulsification. Other methods for preparing semi-solid droplets are well known in the art; see for example, Weaver, U.S. Pat. No. 4,399,219.

The following example is a protocol for producing microdroplets using the emulsification technique (Monshipouri et al. 1995, J. Microencapsulation, 12:255–262). Using an overhead mixer at 2000 rpm, 0.6 g sodium polyphosphate and 2% sodium alginate are dissolved in 100 ml sterile water, and the alginate solution is allowed to degas for 60 minutes. An oil phase is prepared by mixing 300 ml oil, such as canola or olive oil, with 1.0 g purified soy bean lecithin for at least minutes. A slurry containing 1.9 g calcium sulphate in 10 ml 50% glycerol is prepared by sonication for at least 15 minutes. This slurry and a volume of library cells which will yield 1–5 cells per droplet are blended into the alginate solution immediately before introduction to the oil phase. The emulsification process is initiated by slowly transferring the alginate mixture into the oil phase and mixing for 10 minutes at 580 rpm. 500 ml sterile water is then added and the mixing allowed to continue for 5 minutes. Microdroplets can then be removed from the oil by centrifugation. The microdroplets are washed and resuspended in a suitable growth media, ready for culture under standard conditions if required. The size of the droplets can be examined by phase microscopy. For the purpose of sorting by FACS or MACS, if the droplets are outside of the desired size range necessary for sorting, the droplets can be size selected using a filter membrane of the required size limit.

According to the invention, components of the reporter regimen or the target of a drug screen may also be co-encapsulated in a drop with library cell(s). Whole indicator cells or cellular fractions containing a bioassay, enzymes, or reporter molecules may be mixed with library cells suspended in the medium prior to formation of macro- or micro-droplets as previously described. Compounds of interest produced by the library cells may accumulate and diffuse within the droplet to reach the co-encapsulated indicator cells or reporter, and generate a signal. The co-encapsulated indicator cell may be a live target of the desirable compound, e.g. pathogens for anti-infectives, or tumor cells for anticancer agents. Any change in metabolic status of the indicator cells, such as death, or growth inhibition, constitutes a signal and may be detected within the droplet by a variety of methods known in the art. Such methods may include but are not limited to the use of physiological probes, such as vital stains, or measurement of optical properties of the drop.

When the droplets are exposed to components of the reporter regimen, metabolites and compounds produced by the encapsulated library cells and the reporter components may diffuse through the semi-solid medium to produce a signal. For example, a physiological probe may be added to a batch of droplets which are then subjected to the appropriate sorting format. If the library cell(s) are allowed to divide within the drop, the progeny of the original positive cell(s) are kept together in a microcolony, thereby generating a stronger signal. It is preferable that the semi-solid medium is optically compatible with the signal generated by the reporter, e.g. transparent to light for a range of wavelengths, so that the signal can be efficiently detected.

Macrodroplets can be sorted using a colorigenic reporter either by screening by eye or by using any device that allows the droplets to pass through a screening point, and which has the capacity to segregate positives. Microdroplets can be sorted using either FACS or MACS. FACS services are performed by a qualified operator on any suitable machine (e.g. Becton-Dickinson FACStar Plus). Particle suspension densities (cells or droplets) are adjusted to $1 \times 10^6$ particles/ml. In all cases, positives can be sorted directly into multi-well plates at 1 clone per well. MACS is performed using an MPC-M magnetic tube rack following the manufacturer's instructions (Dynal, 5 Delaware Drive, Lake Success, N.Y. 11042).

Encapsulated cells which are found to be positive in a pre-screen or screen can be recovered by culturing the droplet by placing it either on appropriate agar or liquid growth media or by dissolving the droplet in sodium citrate. After a period of culturing, the positive cells may grow out of the droplet. For convenience in handling and storage of droplets, the subsequent culturing may be done in multi-well plates.

Pre-screened positives which have been reduced to a smaller population can then either be frozen and stored in the presence of glycerol or grown in multi-well plates. These can be used to transfer groups of clones using multi-pin replicators onto various types of assay plates (e.g. differential media, selective media, antimicrobial or engineered assay lawns). Specific assays can also be performed within these microtiter plates and read by a standard plate reader or any other format used in current high-throughput screening technologies.

For clarity of discussion, the following subsections describe in more detail the different embodiments of the invention involving prokaryotic and eukaryotic, donor and host organisms. The following embodiments are exemplary and are not intended to be limiting.

5.3. PROTOCOLS FOR THE PREPARATION OF HIGH QUALITY NUCLEIC ACIDS FROM DONOR ORGANISMS

The availability of high quality DNA or RNA as starting material is important in the construction of DNA libraries that are representative of the genetic information of the donor organisms. Methods for extracting, selecting and preparing high quality nucleic acids from cultures of donor organisms or from environmental samples are provided in this section. A method for preparing subtracted DNA probes to be used in pre-screening DNA libraries for the purpose of enriching DNA related to secondary metabolism is also described.

5.3.1. GUANIDINIUM ISOTHIOCYANATE NUCLEIC ACID ISOLATION

Lyophilized or non-lyophilized material can be disrupted by passage though a mechanical grinder, or alternatively by hand in a mortar and pestle in the presence of fine ground glass or pumice. Immediately after grinding, ground lyophilized material may be mixed with 10 ml of lysis buffer per 1–2 g of material. Lysis buffer is 5M guanidine isothiocyanate, 50 mM Hepes pH 7.6, 10 mM EDTA, and 5% μ-mercaptoethanol (or 250 mM DTT). After mixing and incubation at 50° C. for 5 minutes, the solution is rendered to 4% sarcosyl, mixed, and incubated for 5 minutes more at 50° C. prior to centrifugation at 8000 g. If the supernatants are visibly cloudy a 90-minute centrifugation step at 27,000 g may be used to sediment unwanted carbohydrates. Alternatively, a 15,000 g spin may be used to clear the lysate of unwanted contaminants. Following centrifugation, the supernatant is made up to 1.42M CsCl (0.15 g CsCl/ml) and layered onto a previously-made 5.7M CsCl/TE (mM Tris-HCL/1 mM EDTA) solution in ultracentrifugation tubes. Ultra-centrifugation can be carried out at 160.000 g for 18 hours, 20° C. After ultra-centrifugation, a clear, jelly-like layer at the 1.42M/5.7M CsCl interface is DNA, while total cellular RNA is present as a clear pellet at the bottom of the tube.

DNA from the ultra-centrifugation step can be dialyzed against TE buffer, rendered 0.1M NaCl, precipitated with 2.5 volumes of ethanol, dried and redissolved in an appropriate volume of TE. If the DNA layer is white in color, it can be removed and recentrifuged for 8 hours in a CsCl/bisbenzidimide gradient to remove remaining carbohydrates. The dye can be removed by 2-5 washes with 85-isopropanol, and the DNA dialyzed and treated as above.

RNA can be redissolved in resuspension buffer (5M guanidine isothiocyanate, 50 mM Hepes, pH 7.6, 10 mM EDTA), diluted to 1.33M guanidine isothiocyanate with a solution of 50 mM Hepes pH 7.6, 10 mM EDTA. If total RNA is desired, the diluted RNA sample is precipitated by the addition of 2 vol of ethanol or 1 vol of isopropanol. The precipitated RNA is rinsed with 70% ethanol, dried, and resuspended in water or formamide, and stored at −70° C. until used.

5.3.2. ISOLATION OF POLY(A)-CONTAINING RNA

Since the vast majority of eukaryotic mRNA molecules contain tracts of poly(adenylic) acid at the 3' end, up to 250 bases in length, it can be purified by affinity chromatography using oligo-dT cellulose matrix. A wide variety of commercially available oligo-dT matrices may be used, including but not limited to, simple gravity columns, para-magnetic particles, spin and push columns. Isolated mRNA may be stored either dissolved in water, in formamide, or dried at −70° C.

5.3.3. ENRICHMENT OF NON-RIBOSOMAL SEQUENCES FROM TOTAL RNA

The enrichment of non-ribosomal sequences may be an essential step in obtaining useful RNA populations from difficult or uncultivable donor organisms. The fractionation of RNA on neutral sucrose gradients can be useful in purifying the predominant ribosomal RNAs away from other RNA species (R. McGookin 1984, In Methods in Molecular Biology Vol. 2 Nucleic Acids. Humana Press, pp. 109–112). Following centrifugation, the samples containing the largest amounts of ribosomal RNA can be discarded, and the remaining fractions dialyzed and precipitated.

Other methods which utilize random primers with or without random-tailed oligo-dT primers and PCR may be used to amplify low amounts of RNA in starting material.

5.3.4. FILL-IN REACTION USING THE KLENOW FRAGMENT

The use of the Klenow fragment of *E. coli* DNA polymerase, or other DNA polymerase which lacks 3'→5' exonuclease activity, to add nucleotides to the 5' cohesive ends is a standard technique often used to create blunt ended DNA molecules after digestion. When used without a complete nucleotide set, such an activity can be exploited in creating ligation ends that are incompatible with themselves but compatible to each other.

Such a technique has been used to produce high-titer gene libraries and constructs (Hung et al. 1984, Nuc Acids Res 12:1863–1874; Zaborovsky et al. 1986, Gene 42:119; Foster, 1991, Ph.D. thesis, University of California, Santa Barbara; Loftus et al. 1992, Biotechniques 12:172–175.)

The fill-in reaction can be carried out with Klenow buffer (50 mM Tris-HCl pH 7.5, 10 mM MgCl$_2$, 50 mg/ml BSA, 1 mM dNTP), enzyme (10 U/50 µl reaction), and an incubation of 3–4 hours at 37° C. After the reaction, the DNA may be purified by a variety of methods, including but not limited to, affinity chromatography, ethanol precipitation, and spin-column centrifugation.

5.3.5. PROTOCOLS FOR PREPARATION OF SUBTRACTED DNA PROBES FOR PRE-SCREENING

RNA may be isolated from young, mid log-phase cultures of organisms with complex life cycles that have not undergone differentiation. This RNA pool is complementary to genes involved in undifferentiated growth and primary metabolism. The RNA is biotinylated in vitro and hybridized in excess to randomly sheared, gene-sized fragments of genomic DNA from the homologous or closely related heterologous species. Phenol extraction of this mixture results in the removal of genomic sequences complementary to primary metabolism RNA at the interface. This process may be repeated once. The resulting single stranded DNA fragments are composed of the (+) strand of primary metabolism genes and the (+) and (−) strands of other genes, including secondary metabolism-related genes. This mixture of DNA is denatured, and rehybridized for 5–10 half $C_0ts$ under highly stringent conditions such that only related sequences can rehybridize to form double-stranded DNA. The remaining single-stranded DNA can be removed by binding to hydroxyapatite or by digestion with mung bean nuclease. The isolated double-stranded DNA representing non-primary metabolism related genes may then be labeled using random priming, and used as probe to pre-screen a library.

5.3.6. PURIFICATION OF NUCLEIC ACIDS FROM SOIL OR OTHER MIXED ENVIRONMENTAL SAMPLES

Soil samples are flash frozen in liquid nitrogen and stored at −70° C. until processed. Alternatively, soil samples are stored frozen at −20° C. Samples are either thawed on ice immediately prior to use, or freeze-dried prior to processing.

Total nucleic acids are extracted by a number of protocols with minor modifications depending on the physical state and source of the material. Dry to semi-dry samples are frozen and processed directly; very wet samples are flash frozen and freeze-dried; oily samples are diluted with phosphate buffered saline prior to processing. Any of the following procedures may be adapted: Ogram et al. 1987, J. Microbiol. Meth. 7:57–66; Steffan et al. 1988, Appl. Environ. Microbiology, 54:137–161; Werner et al. 1992, J. of Bact. 174(15) :5072–5078; Zhou et al. 1996, Appl. Environmental Microbiol. 62(2):316–322.

Briefly, 5 g samples are lysed directly by dropwise addition to hot guanidium isothiocyanate lysis buffer (see Section 5.3.1), and subjected to a cesium chloride purification. Alternatively, the samples are mixed with 13.5 ml of DNA extraction buffer (100 mM Tris-HCl pH 8.0, 100 mM EDTA, 100 mM sodium phosphate, 1.5 mM NaCl, 1% CTAB (hexadecylmethylammonium bromide) and 100 ul of 20 mg/ml proteinase K in 50 ml centrifuge tubes and shaken by horizontal shaking at 225 rpm for 30 minutes at 37° C. After shaking, 1.5 ml of 20% SDS is added, and the samples incubated at 65° C. for 2 hours, with end-over-end shaking every 15–20 minutes. The supernatants are collected by centrifugation at 6000×g for 10 minutes at 20° C. The pellets are re-extracted 3X by adding 4.5 ml of extraction buffer and 0.5 ml of 20% SDS, vortexing for 1 minute, followed by a 10 minute incubation at 65° C. and re-centrifugation. Pooled supernatants from 3 extractions are extracted twice with chloroform-isoamyl alcohol (48:1). The nucleic acids are precipitated by the addition of 0.6 volumes of isopropanol followed by a one hour incubation and centrifugation at 16,000×g for 20 minutes at room temperature. The crude nucleic acid pellets are then resuspended in 10 mM Tris-HCl pH 8.0, 2 mM EDTA. Further purification of the DNA is by DEAE chromatography if needed. Total RNA is obtained from the crude pellet by selective precipitation of RNA by 4M lithium acetate or acid phenol extraction (Ausubel et al. 1990, Greene Publishing Associates and Wiley Interscience, New York; Hoben et al. 1988, Appl., Environ. Microbiology, 54:703-71).

5.3.7. REPAIR OF DNA

Nicked or degraded DNA samples are repaired by first blunting any fragmented ends with T4 DNA polymerase (New England Biolabs). The DNA is treated in blunting buffer (50 mM Tris-HCl pH 7.8, 10 mM MgCl2, 40 µM dNTPs, U/10 µg T4 DNA polymerase) for 1–2 hours at 37° C. The DNA is ethanol precipitated by the addition of 1/10 volume of 3M sodium acetate and 2.5 volumes of 100% ethanol.

After centrifugation and resuspension in water, the DNA sample is treated with *E. coli* DNA ligase in *E. coli* ligase buffer (50 mM Tris-HCl pH 7.8, 10 mM MgCl2, 10 mM DTT, 26 µM NAD+, and 25 µM BSA, 10 U of *E. coli* for 1–2 hours at 16° C. After treatment the DNA sample is diluted 5 fold with a solution of 20 mM Tris-HCl pH 8.0, 0.3M sodium acetate and extracted once with phenol and once with chloroform The addition of 2.5 volumes of ethanol to the aqueous phase precipitates the DNA. The samples are rinsed two times with 70Fr. ethanol and resuspended in sterile water or mM Tris-HCl, pH 8.0, 1 mM EDTA and frozen at −70° C. until used.

5.4. PROTOCOLS FOR PROKARYOTIC EXPRESSION LIBRARIES

The procedures for preparing natural pathway expression libraries and chimeric pathway expression libraries using prokaryotic host and donor organisms are provided in this section. Purified high quality DNA obtained by the techniques described in Sections 5.3.1–5.3.4 may be used in the following procedures.

5.4.1. BACTERIAL SPECIES, STRAINS, AND CULTURE CONDITIONS

Particularly good expression host organisms are restriction-minus, endonuclease deficient, and recombination deficient. For *E. coli*, a preferred strain is XL1-MR (genotype: McrA-, McrCB-, McrF-, Mrr-, hsdr-, endal-, recA-) For Streptomyces, a preferred strain is *S. lividans* TK64. For *Bacillus subtilis*, preferred strains are *B. subtilis* PB168 trpC2; *B. subtilis* PB5002 sacA, degUhy; *B. subtilis* PB168delta trpC2, pksdelta 75.8; *B. subtilis* ATCC 39320 and 3 9374.

The donor organisms are bacterial species. Some are selected for the ability to produce a unique compound that is detectable by current assays. Others are selected due to their presence in an environmental sample of potential interest. In some examples, marine bacteria were obtained from Harbor Branch Oceanographic Institute and Scripps Institute of Oceanography. They were generally collected from international waters more than 200 miles offshore. Metabolic tests as well as gram testing and colony morphologies were performed to the level necessary to ensure that the samples are taxonomically diverse.

*E. coli* are grown at 37° C. when preparing library stocks, and at 30° C. for expression. Marine, Actinomyces and Streptomyces species are grown only at 30° C.

5.4.2. PREPARATION OF DONOR GENOMIC DNA

From each species of bacteria, a 10 mL culture is grown. The bacteria are pelleted by centrifugation and resuspended in 10 mM Tris, 5 mm EDTA (TE). The DNA may be purified by the procedures described in Section 5.1.2., or the bacterial pellet may be solubilized in SDS/proteinase K, extracted by phenol:chloroform, and precipitated with isopropanol. The resulting purified DNA is resuspended overnight in TE.

Aliquots of each purified DNA are subjected to agarose gel electrophoresis to confirm integrity and to determine the DNA concentration.

To prepare random large DNA fragments for the natural pathway expression library, 20 µg of DNA for each species is partially digested with a frequent-cutting enzyme, such as Sau3A, by incubating in 1X enzyme buffer and 0.01–0.5 unit enzyme per µg DNA for 1 hour at 37° C. The amount of enzyme used may be determined empirically to generate the desired size range. The digested DNAs are pooled, phenol:chloroform extracted, and ethanol-precipitated. 100 µg of this mixture is used for each library that requires large native fragments of genomic DNA. This mixture can optionally be size-fractionated through sucrose gradients. Smaller fragments of DNA for the chimeric pathway expression library can simultaneously be selected by size fractionation.

The digestion and size fractionation are confirmed by subjecting aliquots of the samples to agarose gel electrophoresis.

5.4.3. GENERATION OF PROKARYOTIC PROMOTER FRAGMENTS

Figure 4A:
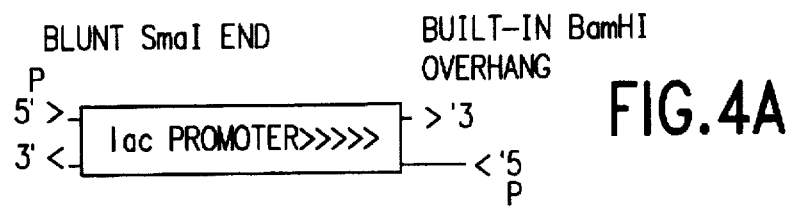

In one example, synthetic oligonucleotides are used to construct a fragment containing two copies of the beta-galactosidase promoter (lac), one on either side of a unique BamH1 site, with each copy of lac positioned to direct transcription toward the centered BamH1 site (FIG. 4A). The synthetic oligonucleotides are phosphorylated by the synthesizer. 400 ng of each oligonucleotide is annealed by boiling five minutes and slow cooling over 30 minutes to 25° C. before ligating 30 minutes at room temperature with T4 DNA ligase. The ligation mix is subjected to agarose gel electrophoresis and 2–7 kbp fragments are excised and purified by Gene Clean. The joined, paired, and properly-oriented cassettes are inserted into the SmaI site of the pBSK plasmid vector by incubation for 16 hours at 15° C. with T4 DNA ligase in 1X ligase/PEG buffer. The ligation mix is introduced into XL1-MR cells. Individual clones are analyzed by restriction enzyme analysis and may optionally be sequenced to confirm orientation and accuracy.

Figure 4B:
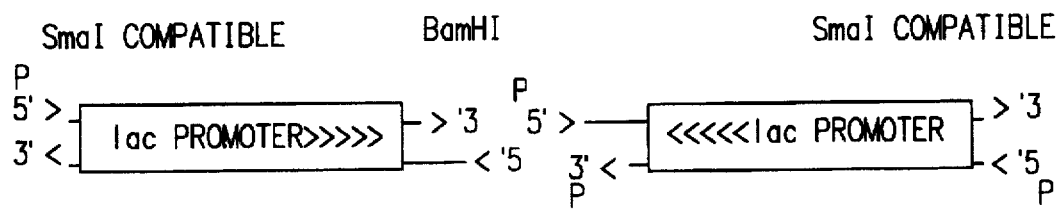
Figure 4C:
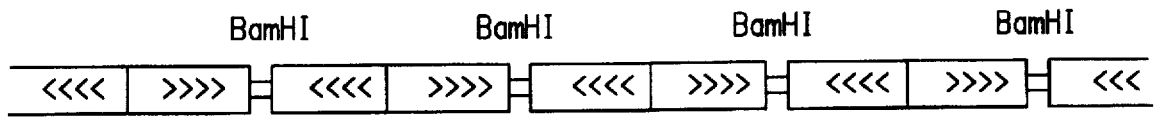
Figure 5B:
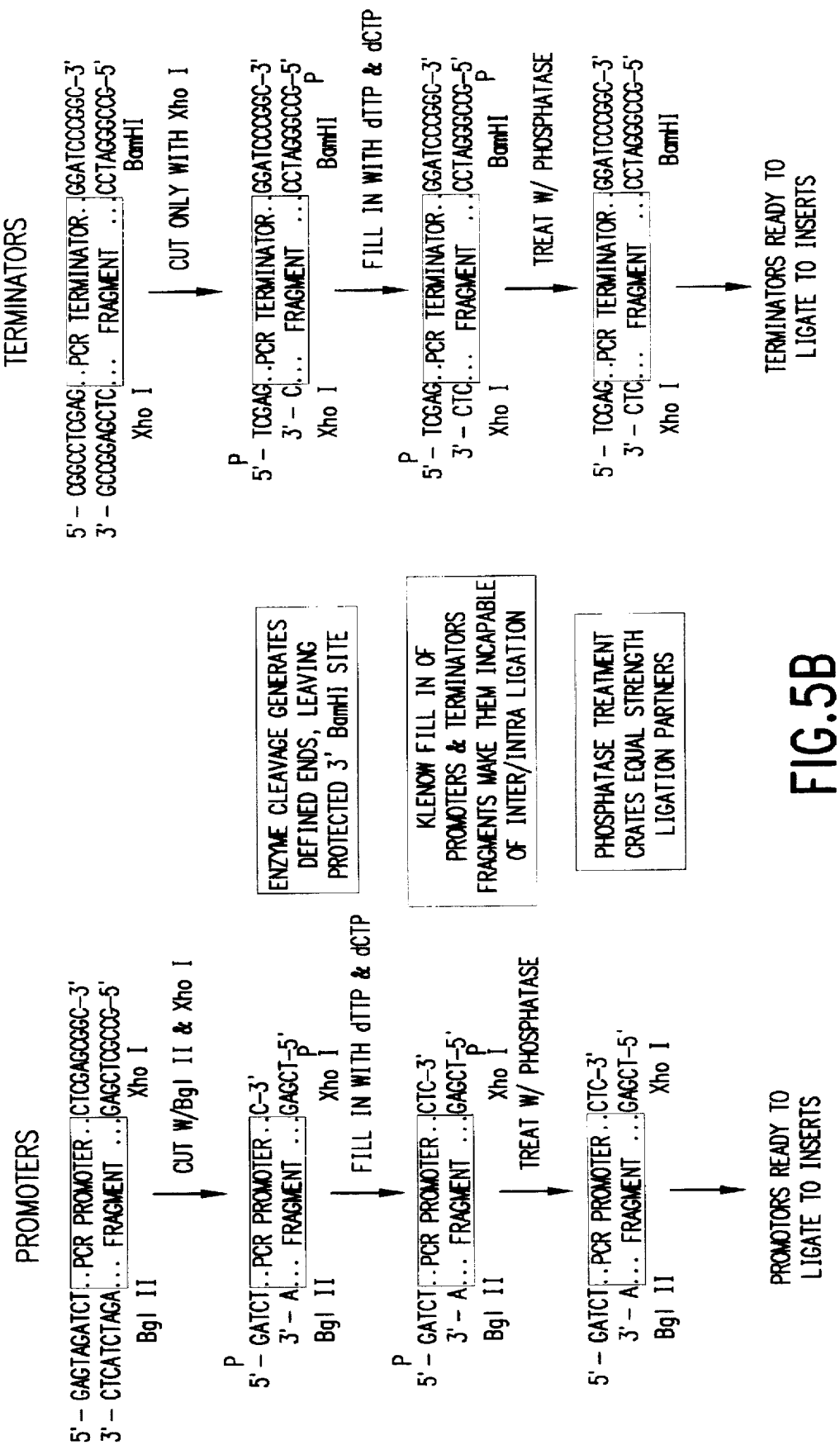
Figure 5C:
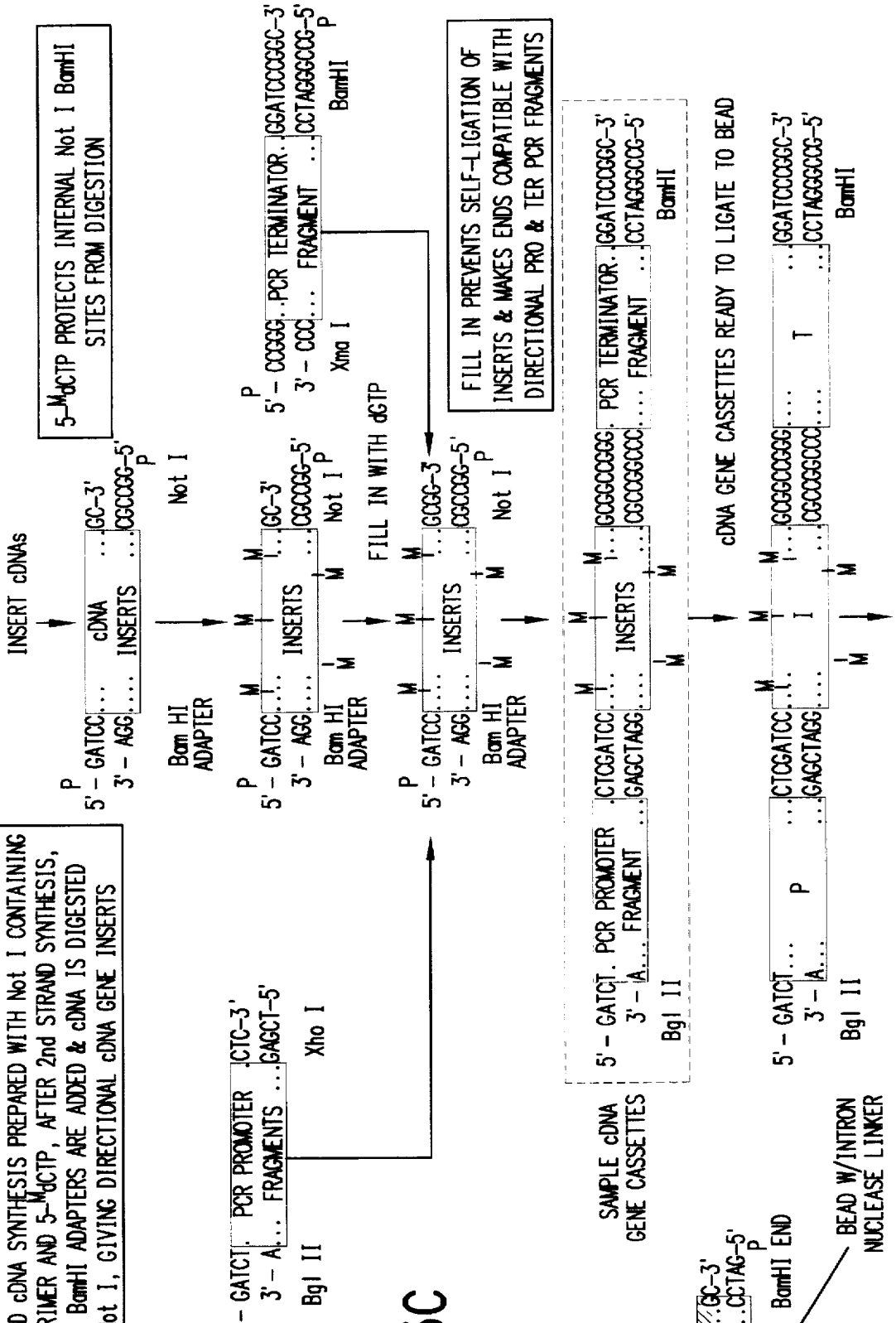
Figure 5D:
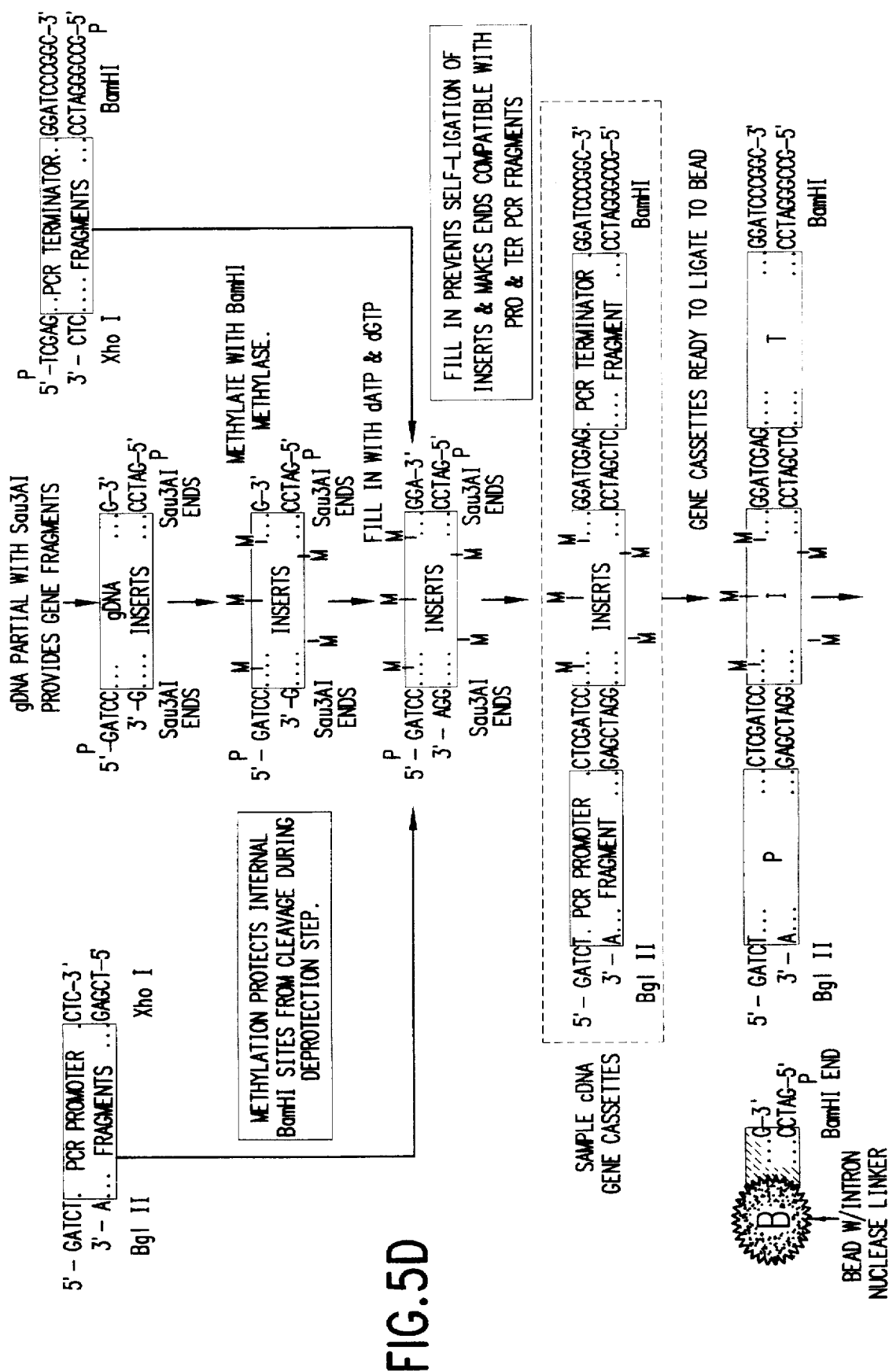
Figure 5E:
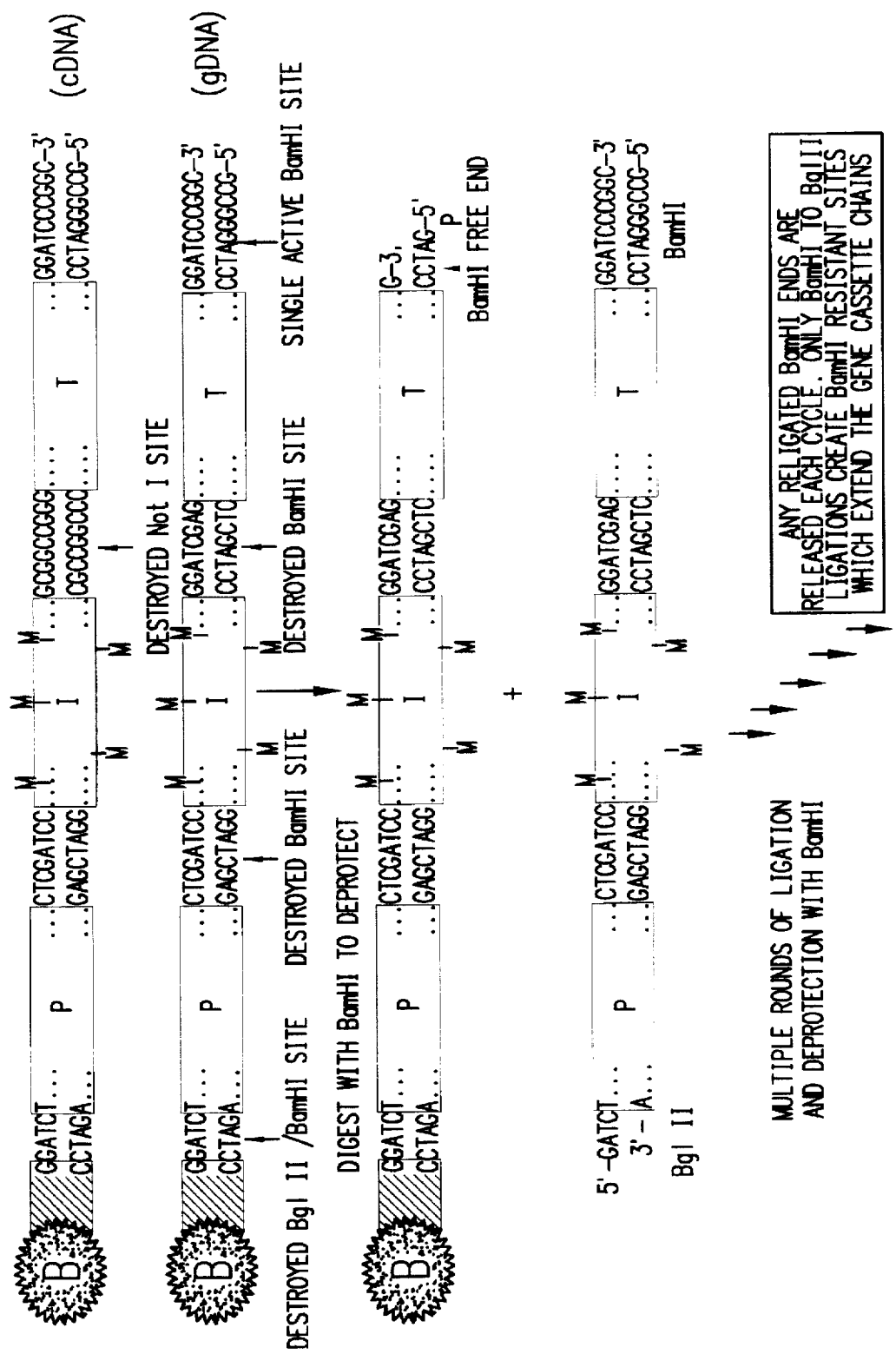
Figure 5G:
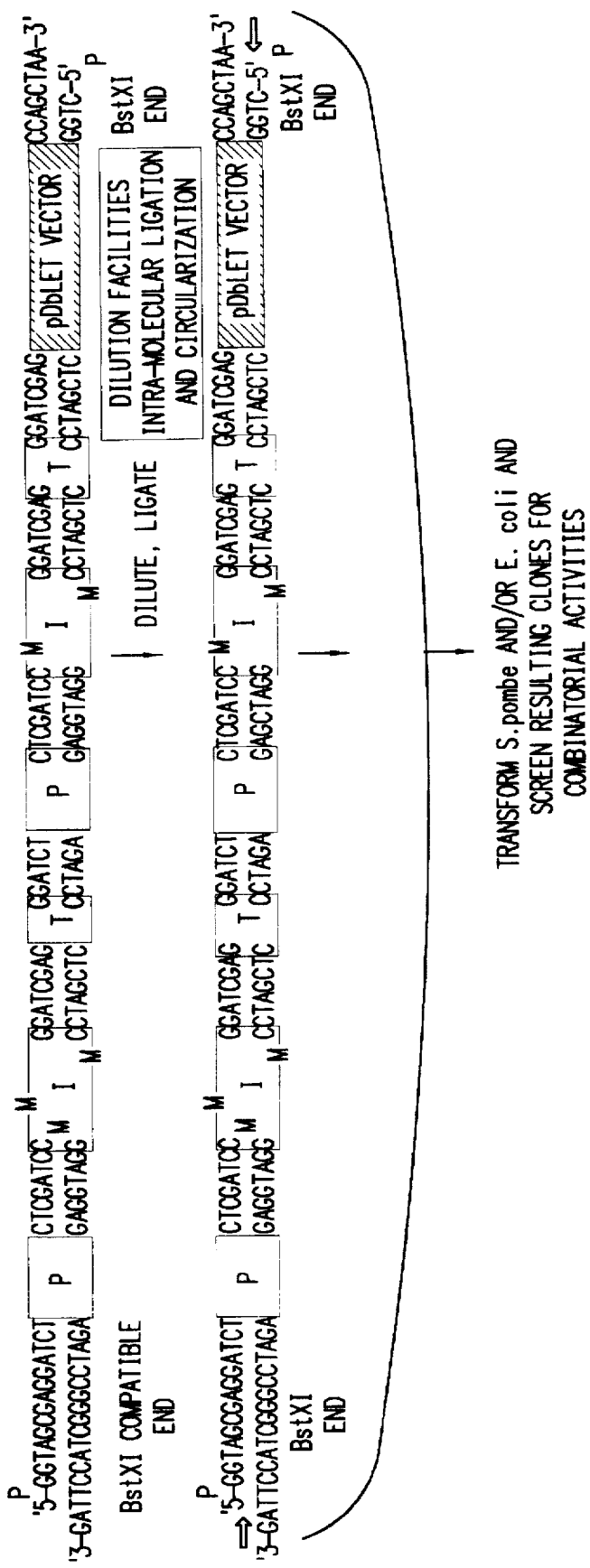

The pBSK-(lac/lac)$_n$ clones (where n is an integer from 2 to 10) are cultured in 0.3 liter quantities and the plasmids purified using a plasmid preparation kit (Qiagen). 40 µg of the selected and purified pBSK-(lac—lac)$_n$. is digested to completion with SmaI in 1X buffer. The digested DNA is subjected to agarose gel electrophoresis and the lac/lac promoter dimers are excised and purified with Gene Clean, and digested to completion with BamH1 in 1X buffer. See FIGS. 4B and 4C. The digested promoter monomers are phenol:chloroform extracted, ethanol precipitated, and dephosphorylated by treatment with CIAP in 1X CIAP buffer. The dephosphorylated, digested promoters are extracted and precipitated as before, and resuspended in TE at a concentration of 20 ng/µl before storing at −20° C. or further use.

In another example, prepared promoter fragments are mixed with similarly-prepared linkers that do not contain promoter sequences, and then used in ligations with the donor genomic DNA. This allows the generation of cassettes with only one promoter, in cases where anti-sense transcription is a consideration.

5.4.4. PREPARATION OF GENE CASSETTES FOR COMBINATORIAL CHIMERIC PATHWAY EXPRESSION LIBRARIES

In one example, BamHI-BamHI fragments of genomic DNA (mean size 3.5 kbp) are mixed with an excess of dephosphorylated promoter fragments, and then ligated. The molar ratio of promoters to genomic DNA fragments is 20:1. The resulting units (lac/genomic DNA fragment/lac) will have a mean size of approximately 4 kbp. Other prokaryotic promoters that may be used include other E. coli promoters (Harley et al., 1987, Nuc Acid Res 15:2343–2361), and Streptomyces promoters (Strohl 1992, Nuc Acid Res V20:961–974) for use in Streptomyces species expression hosts. In hosts with undetermined or significant recombination ability, it is desirable to use a series of different promoters such that any clone containing several cassettes will contain several different promoters.

5.4.5. PREPARATION OF SOLID SUPPORT

Ultralink Immobilized Streptavidin beads were purchased from Pierce (Cat. No. 53113). 3M Emphaze Biosupport Medium AB1 "blank beads" was purchased from Pierce (Cat. No. 53112). Similar solid supports from other vendors may be substituted for this procedure.

Oligonucleotides were purchased from Life Technologies (Gibco-BRL). Oligonucleotide "Bead-link-5" is 5' biotin-GCC GAC CAT TTA AAT CGG TTA AT 3'(SEQ ID NO: 1). "Bead-link-3" is 5'phosphate-TAA CCG ATT TAA ATG GTC GGC 3'(SEQ ID NO: 2). When annealed, these oligonucleotides contain a SwaI restriction endonuclease site (shown underlined below). Annealed bead-link oligonucleotides also leave an AT overhang at the 3' end. This overhang is shown by bolding on oligonucleotide bead-link-5. biotin-GCC GAC CAT TTA AAT CGG TTA AT CGG CTG GTA AAT TTA GCC AAT (SEQ ID NO: 3)

Equimolar amounts of each bead-link oligonucleotide are mixed together in an eppendorf tube. 5M NaCl is added to the tube to a final concentration of 300 mM. The reaction is incubated at 60° C. for 1.5 hr. Annealing was confirmed by agarose gel electrophoresis using non-annealed oligonucleotides as a control.

To prepare blank beads, 100 mg dry beads was resuspended in 1 ml phosphate buffered saline (PBS). Bovine Serum Albumin (BSA) was added to final concentration of 1 mg/ml. Beads were rotated for 4 hrs at room temperature. Beads were pelleted by centrifugation and washed 3× with 1M Tris-HCl pH8.0 for 2 hours at room temperature to block unreacted azalactone sites. Beads were pelleted by brief centrifugation and were washed extensively with PBS. Blank beads were stored in PBS at 4° C. until used.

To bind bead-link oligonucleotide to streptavidin beads 10 µg previously-annealed oligonucleotides were mixed with 20 µl Ultralink Immobilized Streptavidin beads in 1× binding buffer (PBS, 500 mM NaCl). Beads were incubated for three hours at room temperature with inversion to keep the beads suspended. Beads are pelleted and washed 3× with 1ml binding buffer. Beads are then washed and equilibrated with 1× ligation buffer (50 mM Tris-HCl pH7.8, 10 mM MgCl2, 10 mM dithiothreitol, 1 mM ATP, 25 g/ml BSA). Beads are stored at 4° C. until used.

5.4.6. ASSEMBLY OF A COMBINATORIAL CHIMERIC PATHWAY EXPRESSION LIBRARY

Attachment of gene cassettes to magnetic beads: The gene cassettes are phosphorylated using T4 polynucleotide kinase in 1X kinase buffer. The phosphorylated fragments are ethanol precipitated and resuspended in TE. 1/10 of this is ligated to a mixture of two short non-phosphorylated synthetic linkers. The remaining 9/10 is used for a later procedure. Each linker will have one of two rare-cutting enzymes, either Not1 or Srf1. In addition, the Not1-containing linker is biotinylated at the time of synthesis of the oligonucleotides. The Not1 and Srf1 linkers are mixed with the phosphorylated transcription units in the ratio, respectively, of 100:100:1, and ligated with T4 DNA ligase in 1X ligase/PEG buffer for 16 hours at 15° C. This mixture is allowed to bind to avidin-conjugated MPG magnetic beads, and the manufacturer's protocols are used to remove the bead bound transcription units from the ligation mixture.

In the mixture of ligated DNA, approximately ½ will have a biotinylated Not1 linker placed at one end and a Srf1 linker at the other end. The Not1 ends will be bound to the beads by avidin-biotin linkages. The fragments with Not1 linkers at both ends are not involved in further addition steps. The fragments with Srf1 linkers at both ends are not retained in the magnetic separation step.

Preparation of pool of DNA for addition to beadbound DNA: The remaining 9/10 of the phosphorylated transcription units are ligated as above, but to the Srf1 linkers only, followed by digestion to completion with Srf1, dephosphorylation, purification and ethanol precipitation.

De-protection of bead-bound DNA: Transcription units bound to the beads are digested to completion with the Srf1 enzyme in 1X Srf1 buffer. The reaction is heat-inactivated and the beads are removed by magnetic separation.

Concatenation: The beads are then added to a ligation mix containing the dephosphorylated Srf1—Srf1 digested transcription units in 1X ligation buffer. Ligations are commenced by addition of T4 DNA ligase and proceed for 60 minutes, 25° C., before heat-inactivation of the ligase and magnetic separation of the beads. Ligations will primarily occur between phosphorylated bead-bound DNA and non-phosphorylated transcription units. The transcription units on the bead are phosphorylated by T4 polynucleotide kinase, heat-inactivated, magnetically-separated, and returned to the ligation mixture with the addition of more T4 DNA ligase.

This cycle is repeated ten times before cleaving the polymer from the beads by digestion with Not1. The cleaved DNA is ethanol precipitated, resuspended in TE, and viewed on an agarose gel to gauge the quality and size range before insertion into the SuperCos 1 or other vector, according to the expression host. The concatemers are used to generate a prokaryotic library in the relevant expression host as described in Section 5.4.5.

5.4.7. ASSEMBLY OF A COMBINATORIAL NATURAL PATHWAY EXPRESSION LIBRARY

The expression vector for an E. coli library is desirably the cosmid SuperCos 1, capable of maintaining inserts of 30–42 kbp in size. Insertion of the DNA fragments into SuperCos 1 and packaging with Gigapack extracts are performed according to the manufacturer's directions (Stratagene).

Briefly, XL1-MR host cells are infected with SuperCos 1 phage containing the DNA library. This is performed as follows: XL1-MR cells are grown overnight in 5 mL LB medium with 1% maltose, 10 mm MgSO$_4$ at 300 rpm, 37° C. The overnight culture is diluted 1:10 and cultured 3 hours in LB/10 mM MgSO$_4$ at 300 rpm, 37° C. The culture is pelleted by centrifugation at 800×g and resuspended in 5 mL LB. 600 µl of this suspension is incubated with 500 cfu of library packaged in phage particles for 30 minutes at ambient temperature, followed by a 60 minute incubation with 8 vol LB at 300 rpm, 37° C.

In order to amplify the expression libraries, the infected host cells are spread on 150 mm Petri dishes with 50 mL LB, 50 µg/mL ampicillin. The plates are previously dried for 48 hours at ambient temperature. After spreading, the plates are allowed to incubate overnight at 37° C. The plates are scraped and the colonies resuspended with 3 mL 15% glycerol, 85% LB per plate. This bacterial suspension is stored at −70° C. for further use.

To prepare the libraries for screening individual clones, the infected host cells are spread on 150 mm Petri dishes with 50 mL LB, 50 mg/mL ampicillin. The plates are previously dried for 48 hours at ambient temperature. After spreading, the plates are allowed to incubate overnight at 37° C. Resulting colonies are picked with sterile toothpicks and transferred one per well to multi-well plates. Each well of a 384-well plate contains 75/µL LB, 50 µg/mL ampicillin, 7% glycerol. The outer rows (80 wells total) are not inoculated but are similarly filled with medium to provide an evaporation barrier during subsequent incubation and freezing. These inoculated master plates are placed at 37° C. for 16 hours without shaking. The overnight master 384-well plates are used as a source plate to replicate into one or more working 384-well plates or Omni-Trays. The master 384-well plates are then sealed individually and frozen at −80° C. Replication is done with a 384-pin replicator. Before and after each use, the 384-pin replicator is dipped sequentially into bleach for 20 seconds, water for 30 seconds, then ethanol for 5 seconds before flaming. Methods of library assembly are dependent on the selection of vector and expression host.

5.4.8. PRE-SCREENING OF EXPRESSION LIBRARIES

There are three categories of pre-screens: intracellular differential, and selection.

Briefly, the first category, intracellular pre-screening entails introduction of the library into a host engineered to contain a chemo-responsive reporter construct. The reporter is GFP (green fluorescent protein) or β-galactosidase, and selection is done by fluorescence-activated cell sorting (FACS) or macrodroplet sorting.

The second category, differential pre-screening, entails incubation of the library in the host with fluorescent or chromogenic physiological tracers, followed by FACS or macrodroplet sorting.

The third category, selection pre-screening, entails incubation of the library in the host with selective agents such as antibiotics, followed by FACS or macrodroplet sorting to identify surviving or multiplying cells.

For all methods, cell sorting is done on bulk cultures of amplified libraries prior to examination of individual cultures.

The libraries may be pre-screened by FACS or macrodroplet sorting. Pools of host cells containing the DNA libraries are cultured in one of two formats promoting either high or low density micro-environments.

In the first format, cells of the amplified library are examined as individual cells. An *E. coli* library aliquot is grown for 4 hours at 30° C. in vol medium at 300 rpm before pelleting, resuspension in 1 vol sterile ddH$_2$O, incubation with fluorescent probes (as needed), and placement on ice for transfer to the FACS facilities.

In the second format, aliquots of the amplified library are encapsulated and cultured in the presence of substrates or selection agents as described in Section 5.2.3 before transfer to the FACS or macrodroplet sorting facilities.

For cultures to be examined with fluorescent tracers or substrates, the cultures resuspended in ddH$_2$O, are stained before FACS following the manufacturers protocols, typically as follows: incubations are in the dark, at room temperature, for 15 minutes, followed by pelleting for 5 minutes in a 1.5 mL microfuge tube and resuspension in 1 vol cold ddH$_2$O.

After sorting, pools of selected 1–1000 clones or macrodroplets from the expression libraries are cultured in 0.5 L nutrient media. The cultured bacteria and media are processed for chemical analysis by extraction with 0.5 L ethyl acetate. Rotary evaporation yields a crude organic extract of approximately 20 mg-lg extract per liter culture. The cognate cloned DNAs are purified and re-transformed into host cells to confirm the localization of relevant sequences to the cosmid. Chemical samples generated by expression from library clones may be examined by HPLC using a series of columns (cationic, anionic, reverse phase) and subsequently by qualitative chemical analysis using NMR.

5.4.9. METABOLIC TESTING OF MARINE GRAM(−)/*E. COLI* LIBRARY BY PLATE REPLICATION

Each wild-type marine species is tested prior to preparation of the DNA libraries to prevent redundancy and to help determine the array of metabolic tests to be done on the completed libraries.

To prepare the libraries for screening individual clones, the infected host cells, such as *E. coli* XL1-MR, are spread on 150 mm Petri dishes with 50 ml LB, 50 mg/ml ampicillin. The plates are previously dried for 48 hours at ambient temperature. After spreading, the plates are allowed to incubate overnight at 37° C. Resulting colonies are picked with sterile toothpicks and transferred one per well to 384-well plates. Each well contains 75 µl LB, 50 µg/ml ampicillin, 7% glycerol. The outer rows (80 wells total) are not inoculated but are similarly filled with medium to provide an evaporation barrier during subsequent incubation and freezing. These inoculated master plates are placed at 37° C. for 16 hours without shaking. The overnight master 384-well plates are used as a source plate to replicate into one or more working multi-well plates or Omni-Trays. The master 384-well plates are then sealed individually and frozen at −80° C. Replication is done with a 384-pin replicator. Before and after each use, the 384-pin replicator is dipped sequentially into bleach for 20 seconds, water for 30 seconds, then ethanol for 5 seconds before flaming.

Working multi-well plates or Omni-Trays are used as source plates to replicate the DNA libraries onto a series of differential and/or selective media (e.g. siderophore detection media or antimicrobial lawns). The results are compiled and compared to the profiles of the wild-type marine bacteria used to construct the DNA library.

5.4.10. METABOLIC TESTING OF MARINE GRAM(−)/*E. COLI* LIBRARY BY MACRODROPLET ENCAPSULATION

Clones are encapsulated by taking sodium alginate and dissolving in 100 mL of sterile water at a concentration of 1% using an overhead mixer at 2000 rpm. A volume of library suspension is added so as to embed 1–5 clones per droplet. The mixture is allowed to sit for at least 30 minutes to degas. The mixture is then extruded through any device that allows it to form individual droplets. One such example is a syringe with a 25 gauge needle. These are dropped into a gently stirring beaker of 135 mM calcium chloride. Droplets are allowed to harden for 10 minutes and then are transferred to a sterile flask and the calcium chloride removed and replaced with LB/Amp media and a substrate (e.g. x-glucosidamine). Flasks containing the droplets are then shaken at 30° C. overnight and examined the following morning for positive clones indicated by the presence of blue colonies.

Droplets are placed in a single layer in a large clear tray and scanned by eye. Positive colonies are removed and placed in 96-well master plates containing LB/Amp and 50 mM sodium citrate pH 7.4 to dissolve the droplet, and allowed to grow at 37° C. overnight. These overnight master 96-well plates are used as a source plate to replicate into one or more working multi-well plates or Omni-Trays. The master 96-well plates are then sealed individually and frozen at −80° C. Positive clones can then be either sent for specific testing of the products or sent through another round of pre-screening or screening. Further screening may be performed by replication which is done with a multi-pin replicator. Before and after each use, the multi-pin replicator is dipped sequentially into bleach for 20 seconds, water for 30 seconds, then ethanol for 5 seconds before flaming.

5.4.11. METABOLIC TESTING OF MARINE GRAM(−)/*E. COLI* LIBRARIES BY MICRODROPLET ENCAPSULATION

Microdroplets may be generated by the following method.

Using an overhead mixer at 2000 rpm, 0.6 g sodium polyphosphate and 2% Sodium alginate are dissolved in 100 ml sterile water. This mixture is allowed to degas for 60 minutes. Then 1.9 g calcium sulphate is sonicated in ml 50% glycerol for at least 15 minutes. This slurry and a volume of the library suspension which will yield 1–5 cells per droplet are blended into the alginate solution immediately before introduction to an oil phase (olive oil) which has been premixed with the addition of 1.0 g purified soy bean lecithin for at least 30 minutes. The emulsification process is initiated by slowly transferring the alginate mixture into the oil phase and mixing for 10 minutes at 580 rpm. 500 ml sterile water is then added and the mixing allowed to continue for 5 minutes. Microdroplets can then be removed from the oil by centrifugation and washed and resuspended in LB/Amp. For the purpose of sorting by FACS, if the droplets are outside of the desired size range necessary for sorting, the droplets can be size selected using a filter membrane of the required size limit. Clones can then be grown 2 hours at 30° C. with shaking in LB/Amp media containing a fluorescent substrate.

Following incubation the sample is prepared for sorting with FACS by centrifuging, washing and resuspending in sterile water at a density of $1 \times 10^6$ droplets per ml. The size of the droplets can be examined by phase microscopy. FACS services are performed by a qualified operator on a Becton-Dickinson FACStar Plus and positives are sorted directly into multi-well plates containing LB/Amp, isolating positives to 1 clone per well. These plates are allowed to grow at 37° C. until the colonies grow out of the beads (1–2 days). These overnight plates are used as a source plate to replicate into one or more working multi-well plates or Omni-Trays. The master multi-well plates are then sealed individually and frozen at −80° C. Positive clones can then be either sent for specific testing of the products or sent through another round of pre-screening or screening. Further screening may be performed by replication which is done with a 96 or 384-pin replicator. Before and after each use, the replicator is dipped sequentially into bleach for 20 seconds, water for 30 seconds, then ethanol for 5 seconds before flaming.

5.4.12. METABOLIC TESTING OF *ACTINOMYCETES/ STREPTOMYCES LIVIDANS* LIBRARY BY PLATE REPLICATION

Each cultivable wild-type *actinomycete* species is tested prior to preparation of the DNA libraries to prevent taxonomic redundancy, and to help determine the array of metabolic tests to be done on the completed libraries. To prepare the libraries for screening individual clones, the transformed host cells, *Streptomyces lividans* TK66, are spread on 150 mm Petri dishes with F10A. The plates are previously dried for 48 hours at ambient temperature. After spreading, the plates are allowed to incubate overnight at 30° C. Selection is initiated by overlaying with thiostrepton. Resulting colonies are picked with sterile toothpicks and transferred one per well to 96-well plates. Each well contains F10A media. These inoculated master plates are placed at 30° C. for 1–4 days. The overnight master 96-well plates are used as a source plate to replicate into one or more working multi-well plates or Omni-Trays. The master 96-well plates are then sealed individually and frozen at −80° C. Replication is done with a multi-pin replicator. Before and after each use, the multi-pin replicator is dipped sequentially into bleach for 20 seconds, water for 30 seconds, then ethanol for 5 seconds before flaming.

Working multi-well plates or Omni-Trays are used as source plates to replicate the DNA libraries onto a series of differential and/or selective media (e.g. antibiotic plates or antimicrobial lawns). The results are compiled and compared to the profiles of the wild-type bacteria used to construct the DNA library.

5.4.13. METABOLIC TESTING OF *ACTINOMYCETES/ STREPTOMYCES LIVIDANS* LIBRARY BY MACRODROPLET ENCAPSULATION

Clones are encapsulated by the method as described in Section 5.4.10 for *E. coli* libraries. Droplets are allowed to harden for 10 minutes and then are transferred to a sterile flask and the calcium chloride removed and replaced with F10A media and a substrate (e.g. x-gal). Flasks containing the droplets are then shaken at 30° C. for 1–5 days and examined for positive clones indicated by the presence of blue colonies.

Droplets are placed in a single layer in a large clear tray and scanned by eye. Positive colonies are removed and placed in 96-well master plates containing F10A 50 mM sodium citrate pH 7.4 to dissolve the droplets and then grown at 30° C. for 2 days. These overnight master 96-well plates are used as a source plate to replicate into one or more working multi-well plates or Omni-Trays. The master 96-well plates are then sealed individually and frozen at −80° C. Positive clones can then be either sent for specific testing of the products or sent through another round of pre-screening or screening. Further screening may be performed by replication as described above in Section 5.4.9.

5.4.14. PRE-SCREENING OF CLONES BY CO-ENCAPSULATION WITH INDICATOR CELLS

Pools of library clones are titered by plating appropriate dilutions and performing colony counts. Adequate library cells are mixed in 1% alginate to result in approximately 1 cell per macrodroplet. In addition, adequate indicator cells are included to result in approximately 50 target cells per droplet. Macrodroplets are produced as described in Section 5.4.10, and cultured under appropriate conditions for the library and indicator cells.

In general, *S. lividans* library macrodroplets are cultured at 30° C. in R5 or F10A, and *E. coli* library macrodroplets are cultured at 30–37° C. in LB or B3. The media and temperature may be adjusted to accommodate the physiological needs of the indicator cells. To visualize effects of the library cell has on the indicator cells, the following reporter regimens are utilized: to detect cell death, inclusion of neutral red or congo red; to detect cell viability, inclusion of substrate relevant to indicator cell (e g., X-glucopyranoside for *E. faecalis*); to detect B-galactosidase reporter activity in response to promoter activation, inclusion of 80 mg/ml X-gal in culture media. After isolation of positive macrodroplets as described in Section 5.4.10, indicator cells are eliminated by addition of antibiotics that are selective for the library cells but not the indicator cells. The library cells are then stored and/or further examined as desired.

5.5. PROTOCOLS FOR EUKARYOTIC EXPRESSION LIBRARIES

This section describes procedures that may be generally applied to prepare combinatorial gene expression libraries of eukaryotic donor organisms. The steps involved in the preparation of a combinatorial chimeric pathway gene expression library in eukaryotes are shown in FIGS. 5A–5G.

Particularly good expression eukaryotic host organisms are stable, non-filamentous, and characterized sufficiently so as to be genetically manipulatable for the purposes of gene expression. For yeast and fungi, a preferred species is *S. pombe*, which is grown at 30° C. (C. Guthrie and G. R. Funk, Guide to Yeast Genetics and Molecular Biology, Methods in Enzymology, Vol. 194, Academic Press). *A. thaliana* and *N. tabacum* cells are preferred hosts (C. P. Lichtenstein & J. Draper, Genetic Engineering of Plants, DNA Cloning Vol. II, pp. 67–119).

5.5.1. REMOVAL OF SATELLITE GENOMIC DNA BY DENSITY GRADIENT CENTRIFUGATION

Eukaryotic genomes often have large amounts of repetitive DNA which consists of primarily ribosomal coding regions, or sequences of no apparent function. Thus, in preparing genomic DNA from eukaryotic donor organisms, it may be desirable to exclude such non-coding DNA sequences from a library. Standard CsCl genomic DNA purification methods in the presence of the DNA binding dye, Hoechst 33258 (Cooney & Matthews, 1984) may be used to separate out various classes of genomic DNA prior to cloning.

5.5.2. GENERATION OF EUKARYOTIC PROMOTERS AND TERMINATOR FRAGMENTS

Both promoter and terminator gene fragments may be produced by PCR using sequence-specific primers adapted from published sequences of known promoters and terminators. The choice of promoter and terminator sequences can be determined by the host organism used. For instance if *S. pombe* is used as an expression host, both native promoters, such as nmt 1 or ura 4, and non-native promoters such as those derived from viruses, e.g., CMV, SV40 (Forsburg, 1993 Nuc Acid Res. 8:4321–4325), or from humans e.g., chorionic gonadotropin or somatostatin (R. Toyama, H. Okayama 1990, FEBS Letters 268(1) pp. 217–221). Genetically engineered promoters similar to those found in the inducible tetracycline system (Faryar et al. 1992, Curr Genet 21:345–349) may also be used.

PCR reactions may be performed in a commercially available PCR machine using standard PCR reaction conditions and DNA polymerases of high fidelity and throughput, such as but not limited to, Pfu polymerase (Stratagene) or Vent polymerase (New England Biolabs). Since not all primer sets will use the same reaction conditions, precise conditions may be determined empirically by techniques known in the art. PCR oligonucleotide primers maybe obtained commercially or synthesized by methods well known in the art.

The promoter and terminator fragments generated by PCR may comprise restriction sites at the 5' ends. Bgl II, Xho I, and BamHI are used herein to illustrate the principle of the invention. Any restriction sites may be used as long as the site does not appear within the promoter or terminator gene sequences.

To generate cloning sites compatible to cDNA or genomic DNA inserts, cleavage of the promoter gene fragments with Bgl II and Xho I will generate promoter gene fragments which have at their 5' ends a Bgl II site and an Xho I site at their 3' ends. Terminators are cut only with Xho I and will have only an Xho I site at their 5' end. 5' and 3' orientations are based on the expected direction of transcription across the promoter or terminator gene fragment. See FIG. 5B (SEQ ID NOS: 5–19).

Partial fill-in reactions utilizing the large subunit of *E. coli* DNA polymerase I (Klenow fragment) and a subset of deoxynucleotides (in this case dCTP and dTTP) may be used to generate promoter and terminator fragments that are incapable of self-ligation by their Xho I ends. The Bgl II ends of the promoter fragments cannot be affected because of the lack of base-complementarity, and the BamHI end of the terminator fragments have no exposed 5' end for the Klenow fragment to utilize.

Treatment with a phosphatase, such as calf intestine alkaline phosphatase, will prevent BglIIs self-ligations, and provide similar termini for ligations in both the promoter and terminator fragments. cDNA fragments are protected from digestion with NotI by incorporation of 5'-methyl dCTP during first strand synthesis (Short, J. M. 1988, Nuc Acids Res 30 16:7583–7600).

In an alternative embodiment of the invention, when DNA inserts are derived from mRNA, directional cloning may be applied to improve the efficiency of cloning. The cDNA inserts can be unidirectionally ligated in the sense orientation with respect to the promoter and terminator fragments. This can be achieved by generating different, non-ligatible ends on both promoter and terminator fragments. Bgl II, Xho I, XmaI, and BamHI are used to illustrate the invention. Any pair of enzymes that generate compatible ends nd can be protected by methylation can be used.

An XmaI site is substituted for the Xho I site at the 5' ends of the terminator fragments, while the preparation of the promoter fragments is unchanged. Xma I is used because it is compatible with Not I by filling in with Klenow fragment and dCTP. This results in a terminator fragment that has a two-base dCTP-dCTP 5' overhang, which is compatible with suitably prepared Not I digested cDNA gene fragments. See FIG. 5A (SEQ ID NOS: 5–14).

5.5.3. PREPARATION OF DNA INSERTS

Coding gene fragments for the eukaryotic libraries will be derived from two principal DNA sources, namely that of genomic DNA (gDNA) or complementary DNA derived enzymatically from messenger RNA (cDNA). Strategies for preparation of gDNA or cDNA are very similar, but not identical.

Complementary DNA is made from messenger RNA and/or total RNA using standard protocols available in the literature, or particular to a manufacturer's instructions. Isolation of total RNA may be accomplished simultaneously with genomic DNA by the guanidium-isothiocyanate method described in Section 5.3.1, and mRNA can be isolated by subsequent affinity chromatography over oligo-dT cellulose.

First strand cDNA synthesis can use an oligo-dT DNA primer that contains a cloning site, e.g., a Not I site, at the 5' end. An oligonucleotide of random sequence, which contains an internal Not I site near its 5' end, can also be used for randomly-primed first strand synthesis. The use of this alternative primer avoids 3' bias for large mRNAs. Methylated deoxynucleotide, such as 5-methyl-dCTP may be used with a polymerase such as Pfu to provide protection from restriction digestion (Short et al., supra; G. L. Costa, 1994, Strategies 7:8). Only non-methylated sites present in the initial primers will be available for cleavage, thus ensuring a defined 3' end for the cDNAs. Methylated cDNA can also be produced by treatment with methylation, but the directionality of the cloning will be lost because all available sites will be methylated, and thus resistant to enzymatic cleavage.

Defined 5' ends of cDNA may be prepared by ligation of sequence-specific adapters, such as a modified BamHI adapter which has a 5' phosphate. When annealed to its partner oligonucleotide, the adapter contains only a two-base dGTP-dATP 5' overhang and a blunt 5' phosphate end. This modified adapter can be ligated to cDNA that has been treated with Pfu or T4 DNA polymerase as in standard protocols. After ligation of modified BamHI adapters and digestion of the cDNA with Not I, the adapted cDNA can be treated with Klenow fragment and dGTP generating a defined, directionally oriented cDNA gene insert ready for ligation to suitably prepared promoter and terminator fragments. The orientation of the fragments is such that the 5' end of the cDNA is located toward the 3' end of the promoter, and the 3' end of the cDNA is located toward the 5' end of the terminator fragment. See Figure 5C (SEQ ID NOS: 20–24).

Genomic DNA fragments are obtained by partial digestion of total genomic DNA with a frequently cutting restriction enzyme, such as Sau 3AI. This enzyme is widely used for this purpose, and partial digestion followed by sizing though sucrose gradients is a very standard technique. Fragment pools from three different digestions that vary in the concentration of initial enzyme can be used to allow for differences in enzyme sensitivity within the genomes.

Following size fractionation and purification, the fragments can be treated with BamHI methylase to protect any internal BamHI sites, followed by treatment with Klenow fragment and DATP & dGTP. This results in gene fragments that are internally methylated at BamHI sites, and possess only dATP-dGTP overhangs. See FIG. 5D (SEQ ID NOS: 25–29). These fragments are incapable of self-ligation, and are only capable of ligating to suitably prepared promoter and terminator gene fragments.

5.5.4. LIGATION OF INSERT DNA TO PROMOTERS AND TERMINATORS

Suitably prepared cDNA, promoter, and terminator fragments can be ligated at 16° C. over night. A ratio of 10 promoter (P): 1 cDNA: 10 terminator (T) may be used in the ligation reaction. The optimal ratio may be determined empirically by techniques known in the art. The directional cloning procedure provides only one ligation product, i.e., a correctly oriented promoter-sense insert-terminator gene cassette.

Ligation of prepared genomic DNA, promoter, and terminator gene fragments may be carried out at 16° C. with varying ratios. Since none of the ligation components can self-ligate, the optimal ratios may be determined empirically. It is estimated that half of the ligation products formed are directly useable. ¼ of the products formed cannot enter the rounds of ligations, and ¼ of the products can be ligated only once before terminating the growing chain. The following combinations (p=promoter, frag=5'→3' genomic DNA fragment, T=terminator garf=3'→5' genomic DNA fragment):

| 1. P-frag-T | 5. P-garf-T |
| 2. T-frag-P | 6. T-garf-P |
| 3. P-frag-P | 7. P-garf-P |
| 4. T-frag-T | 8. T-garf-T |

Combinations 1,6 & 2,5 represent the desired constructs, but because the orientations of the inserts are random, it is expected that 50% of these constructs will be in the correct orientation for any given gene (1 and 6).

Terminator/terminator gene cassettes may form, but cannot be involved in any subsequent cloning step because of the lack of an exposed 5' end because of the blunted, uncut BamHI end at their 3' termini.

Promoter/promoter constructs will clone in subsequent ligations only to other exposed BamHI ends, because the Bgl II end lacks a 5' phosphate (first round). Subsequent ligations to the exposed Bgl II end should be rare with incoming gene cassettes because of the lack of 5' phosphates. Exposed BamHI ends will only be made possible on resident forming chains and not on incoming new gene cassettes. Thus it is expected that such promoter/promoter gene cassettes will terminate a chain by circularization with a nearby BamHI site on another chain, such circularizations are non-recoverable. If such promoter/promoter fragments become a significant problem to ligation efficiencies then an intermediate kinase treatment of the fixed growing chains prior to addition of new gene cassettes should allow the promoter/promoter fragments to extend the growing chains by forming Bgl II/Bgl II ligation products. The kinase treatment will promote Bgl II/Bgl II and Bgl II/BamHI ligations on the solid phase, which will circularize the growing chains involved.

5.5.5. SERIAL LIGATIONS OF GENE CASSETTES TO FORM CONCATEMERS

Ligation of the gene cassettes, each consisting of either genomic DNA or cDNA insert flanked by promoters/terminator combination will be performed in a method analogous to that outlined previously for prokaryotic DNAs. The major difference here is that this strategy used the endonuclease BamHI to create exposed 3' restriction sites for subsequent cloning. The use of either BamHI methylase or 5-methyl-dCTP insures that BamHI sites within the insert DNA will be protected. See FIGS. 5E and 5F (SEQ ID NOS: 30–40).

After 5–10 rounds of chain ligation, the growing chains of concatemers will be deprotected with BamHI and prepared for ligation to the expression vector by treatment with the Klenow fragment and DATP and dGTP. This will render all ends of the growing chain incapable of ligating to each other, thus eliminating any circularization and loss of concatemer chains.

Vector DNA can be ligated to concatemer chains in a 5:1 molar ratio. Other ratios may also be used. The can be done at 16° C. for 8–12 hours, or at 22° C. for four hours. Following ligation the beads can be washed and resuspended in intron nuclease restriction buffer. Digestion will be carried out as described by the manufacturer's instructions. Any intron nuclease may be used. The enzyme CeuI is preferred for it produces non-palindromic 3' overhangs, which are useful in preventing self-ligations. See FIGS. 5F and 5F (SEQ ID NOS: 41–47).

5.5.6. CIRCULARIZATION AND TRANSFORMATION OF VECTOR CONTAINING CONCATEMER CONSTRUCTS

Concatemer-vector molecules released from the solid phase can be encouraged to undergo intra-molecular ligation by dilution of the CeuI digestion mix 100-fold with 1X ligase buffer. T4 ligase can be added, and the reactions may be carried out at 22° C. for 4–6 hours, or 16° C. overnight. See FIG. 5G. The resulting constructs may be concentrated by microfiltration or freeze-drying, and introduced into either *S. pombe* strains, or alternatively into *E. coli* or *S. lividans* strains by standard methods. Any method may be used, including but not limited to electroporation, and modified calcium-phosphate transformation methods.

5.5.7. PREPARATION AND LIGATION OF PREPARED VECTOR FOR EXPRESSION IN YEAST

This section describes procedures that may be generally applied to prepare combinatorial gene expression libraries using yeast as the host organism.

For preparing a library in *S. pombe*, one possible vector, but certainly not the only vector, is the *E. coli/S. pombe* shuttle vector pDblet (Brun et al. 1995, Gene, 164:173–30 177). This vector has the advantage of having multiple cloning sites and fl phage origins, being expressed at moderately high copy number and being very stable in both *E. coli* and *S. pombe*.

For the present invention, the multiple cloning site (MCS) of pDblet may be modified to accommodate a BstXI site of known sequence. See FIG. 6B. This is because the intron nuclease enzyme that is used to release the concatemer chain from the solid phase generates 3' nucleotide overhangs of a defined sequence (3'GATT . . . ). An engineered BstXI site having the sequence CCACCTAACTGG (SEQ ID NO: 4) generates the appropriate CTAA-3' overhang after cleavage.

To modify pDblet, it can be first cut with SacI & NotI to remove the existing BstXI site which does not have the correct sequence. The pDblet plasmid, once purified by spin-chromatography or other means, can be mixed with a presynthesized oligonucleotide which contains in addition to a correct sequence for the BstXI site, a new NcoI site and SacI- and NotI-compatible overhangs. See FIG. 6C (SEQ ID NOS: 48–49). After ligation and transformation, mini-preps of clones are checked for correctness by digestion with NcoI. Correct clones will be identified by the presence of both a BstXI and NcoI site. Treatment of this modified pDblet, with BstXI followed by XhoI sites generates a vector that contains a 5' XhoI site and a 3° C.TAA BstXI overhang. See FIG. 5F (SEQ ID NOS: 30–40). This cleaved vector can be treated with Klenow fragment and dCTP and dTTP to render it incapable of ligating to itself. Such a vector may be used to accept the concatemer chains.

In one embodiment, the invention encompasses cosmid vectors that contain an autonomously replicating sequence of *S. pombe*, and thus can be used to prepare combinatorial gene expression library in *S. Pombe*. A series of cosmid vectors can be constructed which comprises as least one cloning site for insertion of donor DNA, cos sites for in vitro packaging in λ phage, replication origin(s) and selection markers for cloning in *E. coli*, an autonomously replicating sequence (ARS) of *S. pombe*, and one or more different yeast selection markers, such as but not limited to puromycin, ura4, hygromycin or zeocin.

Cosmid vector SuperCos1 (Stratagene) was linearized with restriction endonuclease BglII. The plasmid, purified by the geneclean procedure (Bio101), was treated with T4 DNA polymerase to "fill-in" the DNA termini. The DNA was again purified by the geneclean procedure. The DNA was treated with T4 DNA ligase and transformed into *E. coli* strain DH5α. Clones were tested for their ability to be cut with restriction enzyme BglII. One clone that was resistant to BglII was isolated for further work was called SCos-BglII.

SCos-BglII was digested/linearized with restriction endonuclease BamHI. The linearized vector was treated with calf-intestine alkaline phosphatase to prevent self-ligation and DNA was purified by the geneclean procedure. An artificial DNA linker containing two DraI, one XhoI, and one BglII restriction endonuclease sites was ligated into the BamHI site with T4 DNA ligase. The ligation was transformed into *E. coli* strain DH5α. The resulting plasmid (pSuperCosB) no longer contains the BamHI restriction endonuclease cleavage site.

pSuperCosB was linearized with restriction endonuclease AatII. The linearized vector was treated with calf-intestine alkaline phosphatase to prevent self-ligation, and was purified by the geneclean procedure. Concurrently, plasmid pDblet was cut with restriction endonuclease AatII. The digested pDblet plasmid was separated by agarose gel electrophoresis. A 1198 bp fragment, containing the yeast autonomously replicating sequence (ARS) was cut from the gel and purified by the geneclean procedure. The ARS-containing DNA fragment was then ligated in the linearized SuperCos1 vector. The ligation was transformed into *E. coli* strain SC110. The resulting clone was called pPCos.

pPCos was digested with restriction endonucleases BglII and XhoI. pDblet was digested with restriction endonucleases BamHI and XhoI. Both digests were separated by agarose gel electrophoresis. The ura4 gene containing BamHI/XhoI fragment and the pPCos vector fragment were cut from the gel and purified by the geneclean procedure. The two DNA fragments were ligated together using T4 DNA ligase. The ligation reaction was then transformed into *E. coli* strain DH5α. The resulting plasmid clone was called pPCos+ura.

The vector pPCos+ura is deposited at the Agricultural Research Service Culture Collection (NRRL), Agricultural Research Service, U.S. Department of Agriculture, 1815 North University Street, Peoria, Ill. 61604, U.S.A. on Oct. 24, 1996, and is given accession number B21637N Alternatively, pPCos can be digested with restriction endonucleases SmaI and BclII. This releases a DNA fragment containing a truncated neomycin resistance gene. The vector is purified from this fragment by agarose gel electrophoresis and the geneclean procedure. An artificial DNA linker containing SpeI, KpnI, and NdeI restriction endonuclease sites is ligated into the vector using T4 DNA ligase. The ligation is transformed into *E. coli* strain DH5α. The resulting vector is called pPCos-Neo.

Moreover, pPCos-Neo- can be linearized with restriction endonuclease NdeI. The linearized vector is treated with calf-intestine alkaline phosphatase to prevent self-ligation and DNA was purified by the geneclean procedure. Concurrently, plasmid pDblet is digested with restriction endonuclease NdeI which releases an approximately 1800 bp fragment containing the ura4 gene. This fragment is separated from the rest of the vector by agarose gel electrophoresis and purified by the geneclean procedure. The ura4 gene fragment is ligated into the pPCos-Neo- vector backbone using T4 DNA ligase. The ligation is transformed in *E. coli* strain DH5α. The resulting plasmid is pPCos1 (see FIG. 14).

5.5.8. PLANT EXPRESSION LIBRARIES

This section describes procedures that may be generally applied to prepare combinatorial gene expression libraries using plant cells as donor and/or host organisms.

For preparation of donor DNA from plants, the following general procedure is applied: (1) a pretreatment of the plant tissue in cold ether to enhance cell disruption; (2) mechanical homogenization of the tissue by grinding with sand, glass beads or aluminum oxide; (3) filtration through a mesh to remove cell debris; and (4) extraction of the DNA by the procedures described in 5.1.2. The resulting purified DNA is modified as described in Sections 5.5.3. The CaMV 35S or nopaline synthase promoter, and nopaline synthase terminator fragments are prepared by PCR as described in Section 5.5.3. The promoter and terminator fragments are attached to the DNA fragments, and ligated to a plant DNA vector as described in 5.5.5 and 5.5.6.

A preferred plant DNA vector is Bin19 or its variants which uses T-DNA borders and trans acting functions of the vir region of a co-resident Ti plasmid in Agrobacterium tumefaciens to transfer the donor genetic material into the nuclear genome of plant host cells (Bevan 1984, supra). Modified Bin19 vectors containing a multiple cloning site, such as pBI121 or pBI221 which are commercially available (Clontech, Palo Alto), can be used. Kanamycin resistance and/or β-glucuronidase activity are used as markers for monitoring transformation, and for pre-screening.

Plant protoplasts are prepared from leaves of *Nicotiana tabacum* plants as described in Potrykus et al. 1988 in "Methods for Plant Molecular Biology" Weissbach and Weissbach ed. Academic Press, page 376–378. The expression constructs are introduced into protoplast cells by transformation using polyethylene glycol as described in Power et al. 1988 in "Methods for Plant Molecular Biology" Weissbach and Weissbach ed. Academic Press, page 388–391. The transformed protoplasts are selected by antibiotic resistance, e.g., kanamycin, and can be encapsulated for pre-screening as described in Section 5.4.10.

6. EXAMPLE: CONSTRUCTION AND SCREENING OF COMBINATORIAL GENE EXPRESSION LIBRARY

The following subsections describe the preparation and pre-screening of combinatorial gene expression libraries using mixtures of terrestrial microorganisms or marine microorganisms as donor organisms. The libraries utilize *Streptomyces lividans*, *E. coli* and *S. pombe* as host organisms. The results show that some of the library cells display metabolic activity of the donor organisms indicating that potentially interesting donor metabolic pathways are functional in the host organisms. In addition, it is shown that one library clone contains DNA encoding a marine bacterial protein that shares sequence homology to a known enzyme in a metabolic pathway.

6.1. MATERIALS AND METHODS

Reagents useful in the present method are generally commercially available. For example:

Gene Clean, Genome kit (Bio101, Vista, Calif.); Restriction enzymes, PCR reagents, and buffers (Promega, Madison, Wis.; New England Biolabs; Stratagene, La Jolla, Calif.); TA cloning kit (Invitrogen, La Jolla, Calif.); Bacterial media (Difco, Inc.); Mira Tip (Hawaiian Marine Imports, Inc.); PBSK plasmid, XL1-MR cells, SuperCos 1 cosmid, Gigapack packaging extracts (Stratagene, La Jolla, Calif.); Qiagen QIAprep plasmid purification kit (Qiagen, Inc., Chatworth, Calif.); avidin-conjugated magnetic porous glass (MPG) beads (CPG, Inc., N.J.); petri dishes, 96- and 384-well plates, Omni-Trays (Nunc), 96- and 384-pin replicator and forms (V & P Scientific, San Diego, Calif.); ampicillin (IBI, Inc., Calif.); green fluorescent protein and GFP cDNA (Clontech, Inc.); oligonucleotides (Genset, La Jolla, Calif.); bacterial species and DNA sequences not elsewhere designated (American Type Culture Collection, Rockville, Md.); 7-ethoxy-heptadecyl-coumarin, BCECF-AM (Molecular Probes, Oregon); 3-methyl benzoate, 3-chlorotoluene, m-toluate, tetracycline, chloramphenicol, acetaminophen, arsenic, antimony, cis-cis-muconate, and other chemicals unless noted (Sigma); and Dynabeads, MPC-M (Dynal, Inc., Lake Success, N.Y.).

6.1.1. MEDIA PREPARATION

Purified water (ddH$_2$O) for general use in media and solutions is purified by softening, reverse osmosis, and deionization. Pacific seawater (sea H$_2$O) is obtained from Scripps Institute of Oceanography (La Jolla, Calif.) and filtered before use. Synthetic seawater (SSW) is prepared from ddH$_2$O by the addition of salts (45.2 mm NaF, 48.8 mm SrCl$_2$, 0.324 mM H$_3$BO$_3$, 0.563 mM KBr, 6.25 mM KCl, 4.99 mM CaCl$_2$, 0.7 mM Na$_2$SO$_4$, 16.4 mM MgCl$_2$, 268 mM NaCl, 45.8 mM Na$_2$SiO$_3$, 1.10 mM EDTA, 1.58 mM NaHCO$_3$) and marine trace elements (0.01% Mira Tip).

LB medium is prepared from ddH$_2$O with 1% tryptone, 0.5% yeast extract, 1% NaCl. W2-B1 is prepared from 75% sea H$_2$O or SSW with 0.25% peptone, 0.15% yeast extract, 0.6% (vol/vol) glycerol.

F10A is prepared from ddH$_2$O containing 2.5% soluble potato starch, 0.2% glucose, 0.5% yeast extract, 0.5% peptone, 0.5% Distiller's solubles (Nutrition Products Co., Louisville, K.Y.), 0.3% calcium carbonate with pH adjusted to 7.

6.2. PRE-SCREENING OF *ACTINOMYCETES/STREPTOMYCES LIVIDANS* COMBINATORIAL NATURAL PATHWAY EXPRESSION LIBRARY BY PLATE REPLICATION AND MACRODROPLET ENCAPSULATION

Thirty four *actinomycetes* species, identified as species # 501–534 were used as donor organisms. The organisms were cultured in F10A medium separately, and genomic DNA was extracted and purified as described in Section 5.3.1.

Approximately 100 μg genomic DNA per species was obtained and mixed together for partial restriction digestion by Sau3A as described in Section 5.4.2. Fragments of genomic DNA were subjected to size fractionation by sucrose gradient centrifugation, and fractions containing 20–40 kb fragments were pooled and partially filled-in with the Klenow fragment so as to be compatible with similarly-prepared vectors below (Korch 1987, Nuc Acids Res 15:3199–3220; Loftus et al. 1992 Biotechniques 12:172–175). 0.5–3.0 μg of the pooled fragments were ligated in multiple batches to 0.5–3.0 μg of pIJ922 and pIJ903 (Hopwood 1985, supra) vector prepared with BamHI or XhoI. The ligated expression constructs were transformed into the host organism, *Streptomyces lividans*, strain TK64 which had been made competent by removal of cell walls with lysozyme (Hopwood 1985, supra). Approximately 11,000 unique clones were generated, amplified and stored as mycelia in 20% glycerol and as spore suspensions in 50% glycerol at −70° C.

To prepare the libraries for screening individual clones, the transformed TK64 host cells were spread on 150 mm Petri dishes filled with F10A agar. After spreading, the plates were allowed to incubate for 21 hours at 30° C. A selection was performed by overlaying plates with thiostrepton at 5 μg/ml, 1 ml/plate. After 48–72 hours, colonies were picked with sterile toothpicks and transferred one per well to 96-well plates Each well contained F10A media. These-inoculated master plates were placed at 30° C. for 1–4 days. The overnight master 96-well plates were used as source plates to replicate into one or more working 96-well plates or Omni-Trays. The master 96-well plates were then sealed individually and frozen at −80° C. Replication was done with a 96-pin replicator which was sterilized by flaming before each use.

Working 96-well plates were used as source plates to replicate the library onto a series of differential and/or selective media and indicator plates. Selective antibiotics included erythromycin, novobiocin and neomycin. Differential media included F10A and R5 medium containing substrates X-glucopyranoside and X-gluconic acid. Indicator plates included library clones grown on F10A then overlaid with a indicator lawn of *Enterococus faecalis* (*E. faecalis*), Bacillus subtilis (*B. subtilis*) or SOS Chromotest (with X-gal).

The results are compiled and compared to the profiles of Streptomyces host TK64.

The clones of the library are also pre-screened by macrodroplet encapsulation. For each pre-screen, 50,000 amplified clones of the library are encapsulated by the method as described in Section 5.4.13.

6.3. PRE-SCREENING OF ACTINOMYCETES/E. COLI COMBINATORIAL CHIMERIC PATHWAY EXPRESSION LIBRARY BY MACRODROPLET ENCAPSULATION

Genomic DNA obtained from the thirty four actinomycetes species (identified as species # 501–534) as described in Section 6.2, were used in the preparation of a combinatorial chimeric pathway gene expression library in a S. lividans host. Fractions containing fragments of Sau3A-digested genomic DNA of 2–7 kb were pooled.

Aliquots of the genomic DNA fragments are ligated to the different promoters separately to form gene cassettes as described in Section 5.5.3. The concatemers are formed by 8 cycles of ligation and deprotection using a different pool of gene cassettes for each cycle, such that the resultant concatemers each have 8 gene cassettes comprising 8 different promoters attached to fragments of genomic DNA.

Ten micrograms of the concatemers were circularized and ligated to 0.5 µg of SuperCos 1 vectors at the BamH1 site to form expression constructs, which were packaged in vitro for infection of the E. coli host cells XL1-MR according to the manufacturer's directions (Stratagene). Approximately 1,000,000 of unique clones are obtained, amplified and pooled to form an amplified library. The library was stored at −70° C. Amplified cells are encapsulated as in Section 5.4.10, and pre-screened as in 5.4.14.

6.4. PRE-SCREENING OF FUNGAL/ SCHIZOSACCHAROMYCES POMBE COMBINATORIAL CHIMERIC PATHWAY EXPRESSION LIBRARIES BY MACRODROPLET ENCAPSULATION

Two combinatorial chimeric pathway expression libraries were prepared using the following fungal donor organisms obtained from ATCC: Trichoderma reesei, Fusarium oxysporum, Penicillium roquefortii, Rhizopus oligosporus, Neurospora crassa, Phycomyces blankesleeanus, Aspergillus fumigatus, spergillus flavus, Emericella heterothallica, Chaetomium gracile, Penicillium notatum, Penicillium chrysogenum.

Each species was cultured separately in 500 ml potato dextrose agar (PDA; Difco) or malt extract agar (MEA; Difco) at medium rpm for 48–72 hours. Spore inoculations of 1×10⁴–1×10⁶ spores per ml were placed into 500 ml of potato extract or malt extract broths in 1 liter culture flasks and grown at 22 C, 225 rpm, 48–72 hours.

Cultures were harvested by filtration through Miracloth (Calbiochem) under vacuum. The collected mycelial masses were washed with 2 liters of ddH$_2$O, and air-dried for 10 minutes before freeze drying. Fungal genomic DNA and mRNA were extracted and purified from the mycelia as described in Sections 5.3.1 and 5.3.2. A portion of the harvested mycelia were freeze-dried and stored at −70° C.

Fungal genomic DNA fragments were prepared as described in Sections 5.4.2. Fungal mRNA was converted into cDNA according to standard methods. (Sambrook et al. 1989, Watson C. J. & Jackson J. F. (1985) DNA cloning: A practical approach 79–88, IRL Press). Weight equivalents of DNA fragments from each species were pooled to yield a genomic DNA pool and a cDNA pool.

Each of these pools containing approximately 5–10 µg of DNA is used independently to assemble a combinatorial chimeric pathway expression library. The following S. pombe-compatible promoters and terminators were generated as described in Section 5.5.2: CMV immediate/early, SV40 early, RSV, HSV thymidine kinase, CaMV, nmti, adh1 and uva4 promoters. The promoter and terminator fragments are combined with the cDNA and genomic DNA pools as described in Sections 5.5.4. Each gene cassette averaging 5 kb in length is concatenated as described in Section 5.5.5. The final concatemers containing 8 gene cassettes each are circularized and inserted into the vector modified pDblet (Brun et al. 1995, Gene, Vol. 164 pp. 173–177) as described in Section 5.5.7. The expression constructs were transformed into S. pombe cells via lithium acetate method of Gietz and Woody (F. D. Gietz & R. A. Woody, Molecular genetics of yeast: A practical approach, chapter 8, pp 121–134). Upon selection for presence of the ura4 marker, 110,000 S. pombe clones are obtained and amplified. The clones are pooled to form an amplified library ready for pre-screening. The following pre-screens are performed: enzyme substrate test, anti-microbial activity, antibiotic resistance.

6.5. PRE-SCREENING OF MARINE GRAM(−)/E. COLI LIBRARY BY PLATE REPLICATION

Marine bacteria obtained from seawater collected near the Bahamas Islands were provided by the Harbor Branch Oceanographic Institute. Each of the wild-type gram-negative pigmented marine bacterial species was tested prior to preparation of the DNA libraries to determine redundancy, and to help determine the array of pre-screens to be done on the completed libraries.

The following assays were performed on the parental species of marine gram-negative/E. coli library, with the indicated results:

| Assay | Positive species out of 37 species |
|---|---|
| Chromazurol S (CAS) | 27 |
| Streptococcus pyogenes | 0 |
| Enterococcus faecalis | 3 |
| Proteus mirabilis | 1 |
| Sarcina aurantiaca | 10 |
| Staphylococcus aureus | 6 |
| Starch digestion | 17 |

Of these assays, the following were selected to be performed on the cells of the combinatorial gene expression library in E. coli: CAS; S. aureus; S. aurantiaca; starch digestion.

Briefly, each of the 40 parental species was inoculated into 5 ml of B3 medium and cultured overnight at 30° C., 300 rpm in Falcon 2059 tubes, the overnight cultures were pelleted and the total genomic DNA extracted by standard procedures. Genomic DNA was quantified by visualization on an agarose gel and 5 µg DNA from each of the 40 species was contributed to a pool totaling 200 µg. The combinatorial natural pathway expression libraries were assembled in E. coli as described in Section 5.1.4. This DNA was partially digested, ligated to SuperCos1 and packaged in λ phage for introduction into E. coli according to the SuperCos1 manufacturer's directions (Stratagene). This resulted in 5×10⁶ unique clones, which was amplified to 7×10⁸/ml cfu by standard protocols. The amplified stock was stored in 15% glycerol at −70° C. for subsequent use.

To prepare the libraries for screening individual clones, the amplified library cells were spread on 150 mm Petri dishes with 50 ml LB, 100 mg/ml ampicillin and 50 mg/ml kanamycin. The plates were previously dried for 24 hours at ambient temperature in the dark. The 7×10⁸/ml cfu stock was diluted in LB to 500 cfu/ml. One ml was spread on each 150 mm plate. After spreading, the plates were allowed to incubate overnight at 37° C. Resulting colonies were picked with sterile toothpicks and transferred one per well to 384-well plates. 6400 colonies were picked and archived. Each well contained 75 µLB, 50 µg/ml ampicillin, 7% glycerol. The outer rows (80 wells total) were not inoculated but were similarly filled with medium to provide an evaporation barrier during subsequent incubation and freezing.

These inoculated master plates were placed at 37° C. for 16 hours without shaking. The overnight master 384-well plates are used as a source plate to replicate into one or more working multi-well plates or Omni-Trays. The master 384-well plates were then sealed individually and frozen at −80° C. Replication was done with a multi-pin replicator. Before and after each use, the 384-pin replicator was dipped sequentially into bleach for 20 seconds, water for 30 seconds, then ethanol for 5 seconds before flaming.

Working multi-well plates or Omni-Trays were used as source plates to replicate the DNA libraries onto a series of differential and/or selective media (e.g. siderophore detection media (CAS) or antimicrobial lawns). The results were compiled and compared to the profiles of the wild-type marine bacteria used to construct the DNA library.

Six clones were isolated that were positive for starch digestion ability. These clones were tested for the ability to inhibit growth of S. aureus or S. aurantiaca, and one clone was found to inhibit the growth of S. aurantiaca. This clone was subjected to further analysis, including DNA sequence analysis, and was found to contain DNA sequences encoding proteins homologous to those in a polyketide synthesis pathway. FIG. 10 shows the alignment of the predicted amino acid sequence of a DNA sequence derived from clone CXC-AMN20 with the actinorhodin dehydrase gene of Streptomyces coelicolor.

The active component from this clone is further analyzed by extraction with organic solvents and purification guided by anti-microbial assays.

The DNA sequence contained in this clone was further examined by multiplex PCR to determine the cognate parental species. PCR primers were selected and synthesized based on sequence of the clone. Highly conserved ribosomal RNA primer sequences were used in the PCR as positive control. The positive control generates a fragment of approximately 2 kb. The amplicon generated from the clone or its cognate parental species was less than 600 bp. Initially, mulitplex PCR reactions were performed by standard method using a set of four pools of genomic DNA of the parental species. Genomic DNA from Pool 1–3 produced the amplicon upon amplification. See FIG. 11. The multiplex PCR reactions were repeated with genomic DNA of individual parental species. FIG. 12 shows that genomic DNA derived from species #6 from Pool 1, species #18 from Pool 2 and species #31 from Pool 3 were positive in the PCR reaction. This suggested that the identified DNA sequence was likely derived from any of these 3 species of marine bacteria.

Thus, the results show that the combinatorial gene expression library contains clones carrying genetic material derived from marine bacteria that encodes metabolic pathway of interest. Furthermore, it is shown that such clones in the library can be identified, and isolated by pre-screening.

6.6. PRE-SCREENING OF MARINE GRAM(−)/E. COLI LIBRARY BY MACRODROPLET ENCAPSULATION 30,000 clones were encapsulated by taking sodium alginate (Protanol LF 20/60, Pronova Biopolymer, Drammer, Norway) and dissolving it in 100 mL of sterile water at a concentration of 1% using an overhead mixer at 2000 rpm. One ml of library suspension containing 30,000 cells was added so as to embed 1–5 clones per droplet. The mixture was allowed to sit for 30 minutes to degas. The mixture was then extruded through a 25 gauge needle. These fluids were dropped into an 0.5 L gently stirring beaker of 135 mM calcium chloride. Droplets were allowed to harden for 10 minutes and then were transferred to a sterile flask and the calcium chloride removed and replaced with LB/Amp media and a substrate, X-glucosaminide, at 80 µg/ml. Other substrates were X-acetate, X-glucopyranoside, X-gal and specific custom substrates relevant to polyketide pathways. Flasks containing the droplets were then shaken at 30° C. overnight and examined the following morning for positive clones indicated by the presence of blue colonies. Clones are also co-encapsulated with indicator cells as described in 5.4.14. Indicator cells include S. aureus, S. aurantiaca.

Droplets were placed in a single layer in a large clear tray and scanned by eye. One X-glucosaminide positive was recovered, resuspended in 15% glycerol and stored at −70° C. Other positive colonies are removed and placed in 96-well master plates containing LB/Amp and 50 mM sodium citrate pH 7.4 to dissolve the matrix, and allowed to grow at 37° C. overnight. These overnight master 96-well plates are used as a source plate to replicate into one or more working multi-well plates or Omni-Trays. The master 96-well plates are then sealed individually and frozen at −80° C. Positive clones are either sent for specific testing of the products or sent through another round of pre-screening or screening. Further screening is performed by replication which is done with a multi-pin replicator.

7. EXAMPLE: CONSTRUCTION AND SCREENING OF ACTINOMYCETES/ STREPTOMYCES LIVIDANS COMBINATORIAL GENE EXPRESSION LIBRARY

The following subsections describe the preparation of a combinatorial natural pathway expression library and a biased combinatorial gene expression library using a mixture of terrestrial microorganisms as donor organisms. Both libraries utilized E. coli as an archival host, and Streptomyces lividans as the expression host.

Briefly, to make the combinatorial natural pathway expression library, an archival cosmid library was made with the DNA of donor organisms. The inserts of the library was then isolated and recloned into Streptomyces vectors for introduction into the host, Streptomyces lividans. To make the biased combinatorial gene expression library, the archival library was pre-selected by hybridization with genes encoding type II polyketide biosynthetic pathways. Genetic material potentially encoding type II polyketide pathways from the actinomycete donor organisms were isolated, randomly mixed, and re-cloned into S. lividans to form the combinatorial expression library.

The clones from both libraries were analysed for antibiotic activity that are potentially the products of novel or hybrid metabolic pathway that are functional in the host organisms.

7.1. MATERIALS AND METHODS

According to the invention, an archival library was constructed in the cosmid pWE15 and E. coli using the chromosomal DNA isolated from thirty-four donor actinomycete strains.

To make the combinatorial natural pathway gene expression library, cosmid DNA was prepared from clones of the archival cosmid library, and were pooled. Due to the fact that actinomycete donor DNA has a high GC content, an enzyme DraI (that does not have G or C in its recognition site) was used to isolate the actinomycete donor DNA from the pooled cosmid DNA. DNA fragments greater than 25 kb in size were enriched by sucrose gradient centrifugation, and ligated to linkers compatible to the cloning sites of the expression vectors. The following Streptomycete expression vectors were used to form the library: pIJ941, pIJ702, pIJ699, pIJ922 and pIJ903 (Hopwood et al., 1985 Genetic Manipulation of Streptomyces, A Laboratory Manual, The John Innes Foundation). The combinatorial natural pathway expression library was then introduced into the expression host S. lividans TK64. Eight thousand and two hundred (8.200) clones were picked, cultured separately, and analysed for the ability to inhibit growth of *Micrococcus lutens, Staphylococcus aureus, Bacillus subtilis, Escherichia coli, Saccharomyces cerevisiae, Candida albicans,* and *Penicillium chrysogenum.* The clones were also tested for DNA reactivity by the SOS test.

To make the biased combinatorial gene expression library, the archival cosmid library was plated out on 150 mm petri dishes to a density of approximately 2,000 colonies per plate. A total of 60,000 colonies were screened. The plates were incubated for 18 hours at 30° C., in order to produce colonies that were approximately 0.5 mm in diameter. These colonies were then replicated to 137 mm, 0.45 μm Nytran discs. The discs were then placed on sheets of 3 MM paper pre-soaked in 10% SDS with the colony side up, and left to soak for 3 minutes. These discs were transferred to sheets of 3 MM paper, presoaked in 0.5M NaOH, 1M NaCl for 5 minutes; then to 3 MM paper presoaked in 0.5M Tris-HCl, 1.5M NaCl for another 5 minutes; and finally to 3 MM paper presoaked in 2× SSC for 5 minutes. The discs were then left to dry in air for at least 6 hours. The DNA was then fixed to the filter by UV crosslinking. DNA probes specific to actI (Malpartida et al., 1984. Nature 309:462–464) and whiE (Davis et al., 1989. Molecular Microbiology 4:1679–1691) polyketide pathway were labelled using the non-radioactive DIG labelling kit and hybridized to the filter discs at 60° C. in a solution of 5× SSC/0.1% SDS overnight. After the incubation, the discs were washed at 60° C. in 1×SSC/0.1% SDS for one to four times, and the colonies which had hybridized with the probes were detected.

About 60–70 positive clones were isolated from the original plates, and pooled. Cosmid DNA was isolated from the pooled clones, and digested with DraI to separate the cosmid vector DNA from the actinomycete DNA. In order to randomly mix the genes in the metabolic pathways, the actinomycete DNA was partially digested with Sau3AI to generate fragemnts in the range of approximately 4–10 kb, and the fragments were ligated to form concatamers of greater than 50 kb. The ligated DNAs were redigested partially with Sau3AI to generate fragments with an approximate size range of 15–30 kb, which were ligated into the BglII site of the vector pIJ702 (Hopwood et al., 1985 Genetic Manipulation of Streptomyces. A Laboratory Manual, The John Innes Foundation). The biased combinatorial expression library was then introduced into the expression host *S. lividans* TK64. Two thousand and two hundred (2,200) clones were picked, cultured separately, and analysed for the ability to inhibit growth of *Micrococcus lutens* (MLUT), *Staphylococcus aureus* (SA1), *Bacillus subtilis* (BS8), *Escherichia coli* (*E. coli*), *Saccharomyces cerevisiae* (SC7), *Candida albicans* (CA917), and *Penicillium chrysogenum* (PC). The clones were also tested for DNA reactivity by the SOS test (SOS).

7.2. RESULTS

For the combinatorial natural pathway expression library, 8,200 clones were screened for antimicrobial activities, and 205 clones (2.5%) of interests were identified. Table VI shows the antimicrobial assay results of 20 clones from the combinatorial natural pathway expression library.

For the biased combinatorial gene expression library, 2,200 clones were screened for antimicrobial activities, and 71 clones (3.2%) of interests were identified. Table VII shows the antimicrobial assay results of nine clones from the combinatorial natural pathway expression library, which will be subjected to chemical structural analysis.

TABLE VI

Results of Antimicrobial Assays of a Sample of Clones in the Actinomycetes/Streptomycete Lividans Combinatorial Natural Expression Library

| Clone | MLUT | SA1 | BS8 | E. coli | SOS | SC7 | CA917 | PC |
|---|---|---|---|---|---|---|---|---|
| W12103/H02 | 5 | 5 | 5 | 0 | 0 | 0 | 0 | 0 |
| W12105/F06 | 4 | 1 | 0 | 0 | 0 | 2 | 0 | 3 |
| W12131/G05 | 5 | 3 | 5 | 3 | 0 | 3 | 0 | 0 |
| W12101/F08 | 3 | 1 | 0 | 1 | 0 | 0 | 0 | 0 |
| W12103/A02 | 3 | 2 | 1 | 2 | 0 | 0 | 0 | 0 |
| W12106/H09 | 5 | 5 | 4 | 1 | 0 | 0 | 0 | 0 |
| W12133/D02 | 5 | 4 | 4 | 1 | 0 | 0 | 0 | 0 |
| W12176/F01 | 5 | 4 | 4 | 0 | 0 | 0 | 0 | 0 |
| W12138/E02 | 5 | 5 | 2 | 2 | 0 | 0 | 0 | 0 |
| W12150/F06 | 5 | 5 | 2 | 3 | 0 | 0 | 0 | 0 |
| W12151/A07 | 2 | 0 | 2 | 4 | 0 | 1 | 1 | 2 |
| W12151/C07 | 3 | 1 | 2 | 4 | 0 | 2 | 2 | 3 |
| W12151/D07 | 3 | 0 | 0 | 4 | 0 | 0 | 0 | 1 |
| W12151/F07 | 3 | 0 | 2 | 4 | 0 | 2 | 2 | 3 |
| W12149/G07 | 4 | 4 | 1 | 3 | 0 | 0 | 0 | 0 |
| W12176/F01 | 5 | 3 | 5 | 3 | 0 | 0 | 0 | 0 |
| W12178/H01 | 3 | 3 | 2 | 4 | 2 | 0 | 0 | 0 |
| W12179/D05 | 3 | 2 | 1 | 4 | 1 | 0 | 0 | 0 |
| W12180/C07 | 5 | 4 | 4 | 4 | 0 | 0 | 0 | 0 |
| W12182/G07 | 4 | 0 | 2 | 3 | 0 | 0 | 0 | 0 |

TABLE VII

Results of Antimicrobial Assays of a Sample of Clones in the
Actinomycetes/Streptomycete Lividans Biased Combinatorial Expression Library

| Clone | MLUT | SA1 | BS8 | E. coli | SOS | SC7 | CA917 | PC |
|---|---|---|---|---|---|---|---|---|
| WD24345/C01 | 3 | 5 | 1 | 4 | 0 | 0 | 0 | 0 |
| WD24355/E02 | 3 | 4 | 0 | 4 | 0 | 0 | 0 | 0 |
| WD25419/E05 | 4 | 2 | 2 | 0 | 0 | 0 | 0 | 0 |
| WD25440/B08 | 4 | 3 | 2 | 3 | 0 | 0 | 0 | 0 |
| WD25466/D01 | 4 | 3 | 0 | 0 | 0 | 0 | 0 | 0 |
| WD25509/G06 | 4 | 0 | 0 | 0 | 0 | 0 | 0 | 0 |
| WD25568/B04 | 4 | 3 | 3 | 0 | 0 | 0 | 0 | 0 |
| WD25609/C09 | 3 | 2 | 0 | 2 | 0 | 0 | 0 | 0 |
| WD25751/A07 | 3 | 3 | 0 | 3 | 0 | 0 | 0 | 0 |

The data show that both the combinatorial natural pathway expression library and the biased combinatorial gene expression library contain clones carrying genetic material that encodes metabolic pathways, possibly novel or hybrid polyketide pathways, that results in the production of compounds with antimicrobial activities.

Having thus disclosed exemplary embodiments of the present invention, it should be noted by those skilled in the art that the disclosures are exemplary only and that various other alternatives, adaptations, and modifications may be made within the scope of the present invention. Accordingly, the present invention is not limited to the specific embodiments as illustrated herein, but is only limited by the following claims.

---

SEQUENCE LISTING ( 1 ) GENERAL INFORMATION:

( i i i ) NUMBER OF SEQUENCES: 51

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: Oligonucleotide "Bead-link-5"
        ( B ) LOCATION: 1...23
        ( D ) OTHER INFORMATION:
        ( A ) NAME/KEY: Other
        ( B ) LOCATION: 1
        ( D ) OTHER INFORMATION: Biotin at nucleotide 1

( x i ) SEQUENCE DESCRIPTION: SEQ ID NO:1:

GCCGACCATT TAAATCGGTT AAT         23

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: Oligonucleotide "Bead-link-3"
        ( B ) LOCATION: 1...21
        ( D ) OTHER INFORMATION:
        ( A ) NAME/KEY: Other
        ( B ) LOCATION: 1
        ( D ) OTHER INFORMATION: Phosphate at nucleotide 1

( x i ) SEQUENCE DESCRIPTION: SEQ ID NO:2:

TAACCGATTT AAATGGTCGG C     21

( 2 ) INFORMATION FOR SEQ ID NO:3:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: Annealed beadlink oligonucleotide
        ( B ) LOCATION: 1...44
        ( D ) OTHER INFORMATION:
        ( A ) NAME/KEY: Other
        ( B ) LOCATION: 8...15, 31...38
        ( D ) OTHER INFORMATION: SwaI restriction
                endonuclease sites ( x i ) SEQUENCE DESCRIPTION: SEQ ID NO:3:

GCCGACCATT TAAATCGGTT AATCGGCTGG TAAATTTAGC CAAT     44

( 2 ) INFORMATION FOR SEQ ID NO:4:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: BstXI site
        ( B ) LOCATION: 1...12
        ( D ) OTHER INFORMATION:

( x i ) SEQUENCE DESCRIPTION: SEQ ID NO:4:

CCACCTAACT GG     12

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: Promoter for cDNA and gDNA inserts
        ( B ) LOCATION: 1...20
        ( D ) OTHER INFORMATION:
        ( A ) NAME/KEY: Other
        ( B ) LOCATION: 10...11
        ( D ) OTHER INFORMATION: Promoter site ( x i ) SEQUENCE DESCRIPTION: SEQ ID NO:5:

GAGTAGATCT CTCGAGCGGC     20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (i i) MOLECULE TYPE: DNA (i x) FEATURE:
    (A) NAME/KEY: Promoter for cDNA and gDNA inserts
    (B) LOCATION: 1...20
    (D) OTHER INFORMATION:
    (A) NAME/KEY: Other
    (B) LOCATION: 10...11
    (D) OTHER INFORMATION: Promoter site (x i) SEQUENCE DESCRIPTION: SEQ ID NO:6:

GCCGCTCGAG AGATCTACTC                    20

(2) INFORMATION FOR SEQ ID NO:7:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (i i) MOLECULE TYPE: DNA (i x) FEATURE:
        (A) NAME/KEY: Promoter for cDNA and gDNA inserts
        (B) LOCATION: 1...6
        (D) OTHER INFORMATION:
        (A) NAME/KEY: Other
        (B) LOCATION: 5...6
        (D) OTHER INFORMATION: Promoter site
        (A) NAME/KEY: Other
        (B) LOCATION: 1
        (D) OTHER INFORMATION: Phosphate at nucleotide 1

(x i) SEQUENCE DESCRIPTION: SEQ ID NO:7:

GATCTC                                    6

(2) INFORMATION FOR SEQ ID NO:8:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (i i) MOLECULE TYPE: DNA (i x) FEATURE:
        (A) NAME/KEY: Promoter for cDNA and gDNA inserts
        (B) LOCATION: 1...6
        (D) OTHER INFORMATION:
        (A) NAME/KEY: Other
        (B) LOCATION: 5...6
        (D) OTHER INFORMATION: Promoter site
        (A) NAME/KEY: Other
        (B) LOCATION: 1
        (D) OTHER INFORMATION: Phosphate at nucleotide 1

(x i) SEQUENCE DESCRIPTION: SEQ ID NO:8:

TCGAGA                                    6

(2) INFORMATION FOR SEQ ID NO:9:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (i i) MOLECULE TYPE: DNA (i x) FEATURE:
        (A) NAME/KEY: Promoter for cDNA and gDNA inserts
        (B) LOCATION: 1...8

( D ) OTHER INFORMATION:
            ( A ) NAME/KEY: Other
            ( B ) LOCATION: 5...6
            ( D ) OTHER INFORMATION: Promoter site
            ( A ) NAME/KEY: Other
            ( B ) LOCATION: 1
            ( D ) OTHER INFORMATION: Phosphate at nucleotide 1

( x i ) SEQUENCE DESCRIPTION: SEQ ID NO:9:

GATCTCTC                                                                                                   8

( 2 ) INFORMATION FOR SEQ ID NO:10:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA ( i x ) FEATURE:
            ( A ) NAME/KEY: Terminator for cDNA inserts
            ( B ) LOCATION: 1...20
            ( D ) OTHER INFORMATION:
            ( A ) NAME/KEY: Other
            ( B ) LOCATION: 10...11
            ( D ) OTHER INFORMATION: Terminator site ( x i ) SEQUENCE DESCRIPTION: SEQ ID NO:10:

GATCCCGGG GGATCCCGGC                                                                                      20

( 2 ) INFORMATION FOR SEQ ID NO:11:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA ( i x ) FEATURE:
            ( A ) NAME/KEY: Terminator for cDNA inserts
            ( B ) LOCATION: 1...20
            ( D ) OTHER INFORMATION:
            ( A ) NAME/KEY: Other
            ( B ) LOCATION: 10...11
            ( D ) OTHER INFORMATION: Terminator site ( x i ) SEQUENCE DESCRIPTION: SEQ ID NO:11:

GCCGGGATCC CCCGGGGATC                                                                                     20

( 2 ) INFORMATION FOR SEQ ID NO:12:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( i i ) MOLECULE TYPE: DNA ( i x ) FEATURE:
            ( A ) NAME/KEY: Terminator for cDNA inserts
            ( B ) LOCATION: 1...15
            ( D ) OTHER INFORMATION:
            ( A ) NAME/KEY: Other
            ( B ) LOCATION: 5...6
            ( D ) OTHER INFORMATION: Terminator site
            ( A ) NAME/KEY: Other
            ( B ) LOCATION: 1
            ( D ) OTHER INFORMATION: Phosphate at nucleotide 1

( x i ) SEQUENCE DESCRIPTION: SEQ ID NO:12:

CCGGGGGATC CCGGC                                                                                    15

( 2 ) INFORMATION FOR SEQ ID NO:13:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: Terminator for cDNA inserts
        ( B ) LOCATION: 1...11
        ( D ) OTHER INFORMATION:
        ( A ) NAME/KEY: Other
        ( B ) LOCATION: 10...11
        ( D ) OTHER INFORMATION: Terminator site
        ( A ) NAME/KEY: Other
        ( B ) LOCATION: 1
        ( D ) OTHER INFORMATION: Phosphate at nucleotide 1

( x i ) SEQUENCE DESCRIPTION: SEQ ID NO:13:

GCCGGGATCC C                                                                                         11

( 2 ) INFORMATION FOR SEQ ID NO:14:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: Terminator for cDNA inserts
        ( B ) LOCATION: 1...13
        ( D ) OTHER INFORMATION:
        ( A ) NAME/KEY: Other
        ( B ) LOCATION: 10...11
        ( D ) OTHER INFORMATION: Terminator site
        ( A ) NAME/KEY: Other
        ( B ) LOCATION: 1
        ( D ) OTHER INFORMATION: Phosphate at nucleotide 1

( x i ) SEQUENCE DESCRIPTION: SEQ ID NO:14:

GCCGGGATCC CCC                                                                                       13

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: Terminator
        ( B ) LOCATION: 1...20
        ( D ) OTHER INFORMATION:
        ( A ) NAME/KEY: Other
        ( B ) LOCATION: 10...11
        ( D ) OTHER INFORMATION: Terminator site ( x i ) SEQUENCE DESCRIPTION: SEQ ID NO:15:

CGGCCTCGAG GGATCCCGGC                                                                                20

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: Terminator
        ( B ) LOCATION: 1...20
        ( D ) OTHER INFORMATION:
        ( A ) NAME/KEY: Other
        ( B ) LOCATION: 10...11
        ( D ) OTHER INFORMATION: Terminator site ( x i ) SEQUENCE DESCRIPTION: SEQ ID NO:16:

GCCGGGATCC CTCGAGGCCG         20

( 2 ) INFORMATION FOR SEQ ID NO:17:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: Terminator
        ( B ) LOCATION: 1...15
        ( D ) OTHER INFORMATION:
        ( A ) NAME/KEY: Other
        ( B ) LOCATION: 5...6
        ( D ) OTHER INFORMATION: Terminator site
        ( A ) NAME/KEY: Other
        ( B ) LOCATION: 1
        ( D ) OTHER INFORMATION: Phosphate at nucleotide 1

( x i ) SEQUENCE DESCRIPTION: SEQ ID NO:17:

TCGAGGGATC CCGGC         15

( 2 ) INFORMATION FOR SEQ ID NO:18:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: Terminator
        ( B ) LOCATION: 1...11
        ( D ) OTHER INFORMATION:
        ( A ) NAME/KEY: Other
        ( B ) LOCATION: 10...11
        ( D ) OTHER INFORMATION: Terminator site
        ( A ) NAME/KEY: Other
        ( B ) LOCATION: 1
        ( D ) OTHER INFORMATION: Phosphate at nucleotide 1

( x i ) SEQUENCE DESCRIPTION: SEQ ID NO:18:

GCCGGGATCC C         11

( 2 ) INFORMATION FOR SEQ ID NO:19:

( i ) SEQUENCE CHARACTERISTICS:
        ( A ) LENGTH: 13 base pairs
        ( B ) TYPE: nucleic acid ( C ) STRANDEDNESS: single
( D ) TOPOLOGY: linear ( i i ) MOLECULE TYPE: DNA ( i x ) FEATURE:
  ( A ) NAME/KEY: Terminator
  ( B ) LOCATION: 1...13
  ( D ) OTHER INFORMATION:
  ( A ) NAME/KEY: Other
  ( B ) LOCATION: 10...11
  ( D ) OTHER INFORMATION: Terminator site
  ( A ) NAME/KEY: Other
  ( B ) LOCATION: 1
  ( D ) OTHER INFORMATION: Phosphate at nucleotide 1

( x i ) SEQUENCE DESCRIPTION: SEQ ID NO:19:

GCCGGGATCC CTC      13

( 2 ) INFORMATION FOR SEQ ID NO:20:

( i ) SEQUENCE CHARACTERISTICS:
  ( A ) LENGTH: 7 base pairs
  ( B ) TYPE: nucleic acid
  ( C ) STRANDEDNESS: single
  ( D ) TOPOLOGY: linear ( i i ) MOLECULE TYPE: DNA ( i x ) FEATURE:
  ( A ) NAME/KEY: Other
  ( B ) LOCATION: 5...6
  ( D ) OTHER INFORMATION: cDNA inserts
  ( A ) NAME/KEY: Other
  ( B ) LOCATION: 1
  ( D ) OTHER INFORMATION: Phosphate at nucleotide 1

( x i ) SEQUENCE DESCRIPTION: SEQ ID NO:20:

GATCCGC      7

( 2 ) INFORMATION FOR SEQ ID NO:21:

( i ) SEQUENCE CHARACTERISTICS:
  ( A ) LENGTH: 9 base pairs
  ( B ) TYPE: nucleic acid
  ( C ) STRANDEDNESS: single
  ( D ) TOPOLOGY: linear ( i i ) MOLECULE TYPE: DNA ( i x ) FEATURE:
  ( A ) NAME/KEY: Other
  ( B ) LOCATION: 6...7
  ( D ) OTHER INFORMATION: cDNA inserts ( x i ) SEQUENCE DESCRIPTION: SEQ ID NO:21:

GGCCGCGGA      9

( 2 ) INFORMATION FOR SEQ ID NO:22:

( i ) SEQUENCE CHARACTERISTICS:
  ( A ) LENGTH: 9 base pairs
  ( B ) TYPE: nucleic acid
  ( C ) STRANDEDNESS: single
  ( D ) TOPOLOGY: linear ( i i ) MOLECULE TYPE: DNA ( i x ) FEATURE:
  ( A ) NAME/KEY: Other
  ( B ) LOCATION: 5...6
  ( D ) OTHER INFORMATION: Methylated inserts
  ( A ) NAME/KEY: Other
  ( B ) LOCATION: 1

( D ) OTHER INFORMATION: Phosphate at nucleotide 1

( x i ) SEQUENCE DESCRIPTION: SEQ ID NO:22:

GATCCGCGG 9

( 2 ) INFORMATION FOR SEQ ID NO:23:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: cDNA gene cassettes
        ( B ) LOCATION: 1...32
        ( D ) OTHER INFORMATION:
        ( A ) NAME/KEY: Other
        ( B ) LOCATION: 5...6
        ( D ) OTHER INFORMATION: Promoter site
        ( A ) NAME/KEY: Other
        ( B ) LOCATION: 13...14
        ( D ) OTHER INFORMATION: Methylated inserts
        ( A ) NAME/KEY: Other
        ( B ) LOCATION: 22...23
        ( D ) OTHER INFORMATION: Terminator site ( x i ) SEQUENCE DESCRIPTION: SEQ ID NO:23:

GATCTCTCGA TCCGCGGCCG GGGGATCCCG GC 32

( 2 ) INFORMATION FOR SEQ ID NO:24:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: cDNA gene cassettes
        ( B ) LOCATION: 1...28
        ( D ) OTHER INFORMATION:
        ( A ) NAME/KEY: Other
        ( B ) LOCATION: 10...11
        ( D ) OTHER INFORMATION: Terminator site
        ( A ) NAME/KEY: Other
        ( B ) LOCATION: 19...20
        ( D ) OTHER INFORMATION: Methylated inserts
        ( A ) NAME/KEY: Other
        ( B ) LOCATION: 27...28
        ( D ) OTHER INFORMATION: Promoter site ( x i ) SEQUENCE DESCRIPTION: SEQ ID NO:24:

GCCGGGATCC CCCGGCCGCG GATCGAGA 28

( 2 ) INFORMATION FOR SEQ ID NO:25:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: Gene fragments
        ( B ) LOCATION: 1...6
        ( D ) OTHER INFORMATION:
        ( A ) NAME/KEY: Other ( B ) LOCATION: 5...6
                    ( D ) OTHER INFORMATION: gDNA inserts
                    ( A ) NAME/KEY: Other
                    ( B ) LOCATION: 1
                    ( D ) OTHER INFORMATION: Phosphate at nucleotide 1

( x i ) SEQUENCE DESCRIPTION: SEQ ID NO:25:

GATCCG                                                                                        6

( 2 ) INFORMATION FOR SEQ ID NO:26:

( i ) SEQUENCE CHARACTERISTICS:
                    ( A ) LENGTH: 6 base pairs
                    ( B ) TYPE: nucleic acid
                    ( C ) STRANDEDNESS: single
                    ( D ) TOPOLOGY: linear ( i i ) MOLECULE TYPE: DNA ( i x ) FEATURE:
                    ( A ) NAME/KEY: Gene fragments
                    ( B ) LOCATION: 1...6
                    ( D ) OTHER INFORMATION:
                    ( A ) NAME/KEY: Other
                    ( B ) LOCATION: 5...6
                    ( D ) OTHER INFORMATION: gDNA inserts
                    ( A ) NAME/KEY: Other
                    ( B ) LOCATION: 1
                    ( D ) OTHER INFORMATION: Phosphate at nucleotide 1

( x i ) SEQUENCE DESCRIPTION: SEQ ID NO:26:

GATCCG                                                                                        6

( 2 ) INFORMATION FOR SEQ ID NO:27:

( i ) SEQUENCE CHARACTERISTICS:
                    ( A ) LENGTH: 8 base pairs
                    ( B ) TYPE: nucleic acid
                    ( C ) STRANDEDNESS: single
                    ( D ) TOPOLOGY: linear ( i i ) MOLECULE TYPE: DNA ( i x ) FEATURE:
                    ( A ) NAME/KEY: Gene fragments
                    ( B ) LOCATION: 1...8
                    ( D ) OTHER INFORMATION:
                    ( A ) NAME/KEY: Other
                    ( B ) LOCATION: 5...6
                    ( D ) OTHER INFORMATION: Methylated inserts
                    ( A ) NAME/KEY: Other
                    ( B ) LOCATION: 1
                    ( D ) OTHER INFORMATION: Phosphate at nucleotide 1

( x i ) SEQUENCE DESCRIPTION: SEQ ID NO:27:

GATCCGGA                                                                                      8

( 2 ) INFORMATION FOR SEQ ID NO:28:

( i ) SEQUENCE CHARACTERISTICS:
                    ( A ) LENGTH: 31 base pairs
                    ( B ) TYPE: nucleic acid
                    ( C ) STRANDEDNESS: single
                    ( D ) TOPOLOGY: linear ( i i ) MOLECULE TYPE: DNA ( i x ) FEATURE:
                    ( A ) NAME/KEY: cDNA gene cassettes
                    ( B ) LOCATION: 1...31
                    ( D ) OTHER INFORMATION:
                    ( A ) NAME/KEY: Other
                    ( B ) LOCATION: 5...6
                    ( D ) OTHER INFORMATION: Promotor site (A) NAME/KEY: Other
(B) LOCATION: 13...14
(D) OTHER INFORMATION: Methylated inserts
(A) NAME/KEY: Other
(B) LOCATION: 21...22
(D) OTHER INFORMATION: Terminator site (x i) SEQUENCE DESCRIPTION: SEQ ID NO:28:

GATCTCTCGA TCCGGATCGA GGGATCCCGG C     31

(2) INFORMATION FOR SEQ ID NO:29:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: cDNA gene cassettes
(B) LOCATION: 1...27
(D) OTHER INFORMATION:
(A) NAME/KEY: Other
(B) LOCATION: 10...11
(D) OTHER INFORMATION: Terminator site
(A) NAME/KEY: Other
(B) LOCATION: 18...19
(D) OTHER INFORMATION: Methylated inserts
(A) NAME/KEY: Other
(B) LOCATION: 26...27
(D) OTHER INFORMATION: Promoter site (x i) SEQUENCE DESCRIPTION: SEQ ID NO:29:

GCCGGGATCC CTCGATCCGG ATCGAGA     27

(2) INFORMATION FOR SEQ ID NO:30:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: Other
(B) LOCATION: 6...7
(D) OTHER INFORMATION: Promoter site
(A) NAME/KEY: Other
(B) LOCATION: 14...15
(D) OTHER INFORMATION: Methylated inserts
(A) NAME/KEY: Other
(B) LOCATION: 23...24
(D) OTHER INFORMATION: Terminator site (x i) SEQUENCE DESCRIPTION: SEQ ID NO:30:

GGATCTCTCG ATCCGCGGCC GGGGGATCCC GGC     33

(2) INFORMATION FOR SEQ ID NO:31:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: Other
(B) LOCATION: 10...11

( D ) OTHER INFORMATION: Terminator site
( A ) NAME/KEY: Other
( B ) LOCATION: 19...20
( D ) OTHER INFORMATION: Methylated inserts
( A ) NAME/KEY: Other
( B ) LOCATION: 27...28
( D ) OTHER INFORMATION: Promoter site ( x i ) SEQUENCE DESCRIPTION: SEQ ID NO:31:

GCCGGGATCC CCCGGCCGCG GATCGAGAGA TCC    33

( 2 ) INFORMATION FOR SEQ ID NO:32:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: DNA ( i x ) FEATURE:
( A ) NAME/KEY: Other
( B ) LOCATION: 6...7
( D ) OTHER INFORMATION: Promoter site
( A ) NAME/KEY: Other
( B ) LOCATION: 14...15
( D ) OTHER INFORMATION: Methylated inserts
( A ) NAME/KEY: Other
( B ) LOCATION: 22...23
( D ) OTHER INFORMATION: Terminator site ( x i ) SEQUENCE DESCRIPTION: SEQ ID NO:32:

GGATCTCTCG ATCCGGATCG AGGGATCCCG GC    32

( 2 ) INFORMATION FOR SEQ ID NO:33:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: DNA ( i x ) FEATURE:
( A ) NAME/KEY: Other
( B ) LOCATION: 10...11
( D ) OTHER INFORMATION: Terminator site
( A ) NAME/KEY: Other
( B ) LOCATION: 18...19
( D ) OTHER INFORMATION: Methylated inserts
( A ) NAME/KEY: Other
( B ) LOCATION: 26...27
( D ) OTHER INFORMATION: Promoter site ( x i ) SEQUENCE DESCRIPTION: SEQ ID NO:33:

GCCGGGATCC CTCGATCCGG ATCGAGAGAT CC    32

( 2 ) INFORMATION FOR SEQ ID NO:34:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA ( i x ) FEATURE:
( A ) NAME/KEY: Other
( B ) LOCATION: 6...7
( D ) OTHER INFORMATION: Promoter site
( A ) NAME/KEY: Other ( B ) LOCATION: 14...15
                    ( D ) OTHER INFORMATION: Methylated inserts
                    ( A ) NAME/KEY: Other
                    ( B ) LOCATION: 22...23
                    ( D ) OTHER INFORMATION: Terminator site ( x i ) SEQUENCE DESCRIPTION: SEQ ID NO:34:

GGATCTCTCG ATCCGGATCG AGG                                                                    23

( 2 ) INFORMATION FOR SEQ ID NO:35:

( i ) SEQUENCE CHARACTERISTICS:
                    ( A ) LENGTH: 27 base pairs
                    ( B ) TYPE: nucleic acid
                    ( C ) STRANDEDNESS: single
                    ( D ) TOPOLOGY: linear ( i i ) MOLECULE TYPE: DNA ( i x ) FEATURE:
                    ( A ) NAME/KEY: Other
                    ( B ) LOCATION: 5...6
                    ( D ) OTHER INFORMATION: Terminator site
                    ( A ) NAME/KEY: Other
                    ( B ) LOCATION: 13...14
                    ( D ) OTHER INFORMATION: Methylated inserts
                    ( A ) NAME/KEY: Other
                    ( B ) LOCATION: 21...22
                    ( D ) OTHER INFORMATION: Promoter site ( x i ) SEQUENCE DESCRIPTION: SEQ ID NO:35:

GATCCCTCGA TCCGGATCGA GAGATCC                                                                27

( 2 ) INFORMATION FOR SEQ ID NO:36:

( i ) SEQUENCE CHARACTERISTICS:
                    ( A ) LENGTH: 67 base pairs
                    ( B ) TYPE: nucleic acid
                    ( C ) STRANDEDNESS: single
                    ( D ) TOPOLOGY: linear ( i i ) MOLECULE TYPE: DNA ( i x ) FEATURE:
                    ( A ) NAME/KEY: Other
                    ( B ) LOCATION: 6...7, 28...29, 50...51
                    ( D ) OTHER INFORMATION: Promoter site
                    ( A ) NAME/KEY: Other
                    ( B ) LOCATION: 14...15, 36...37, 58...59
                    ( D ) OTHER INFORMATION: Methylated site
                    ( A ) NAME/KEY: Other
                    ( B ) LOCATION: 22...23, 44...45, 66...67
                    ( D ) OTHER INFORMATION: Terminator site ( x i ) SEQUENCE DESCRIPTION: SEQ ID NO:36:

GGATCTCTCG ATCCGGATCG AGGGATCTCT CGATCCGGAT CGAGGGATCT CTCGATCCGG                            60

ATCGAGG                                                                                      67

( 2 ) INFORMATION FOR SEQ ID NO:37:

( i ) SEQUENCE CHARACTERISTICS:
                    ( A ) LENGTH: 71 base pairs
                    ( B ) TYPE: nucleic acid
                    ( C ) STRANDEDNESS: single
                    ( D ) TOPOLOGY: linear ( i i ) MOLECULE TYPE: DNA ( i x ) FEATURE:
                    ( A ) NAME/KEY: Other
                    ( B ) LOCATION: 1
                    ( D ) OTHER INFORMATION: Phosphate at nucleotide 1
                    ( A ) NAME/KEY: Other ( B ) LOCATION: 5...6, 27...28, 49...50
                    ( D ) OTHER INFORMATION: Terminator site
                    ( A ) NAME/KEY: Other
                    ( B ) LOCATION: 13...14, 35...36, 57...58
                    ( D ) OTHER INFORMATION: Methylated inserts
                    ( A ) NAME/KEY: Other
                    ( B ) LOCATION: 21...22, 43...44, 65...66
                    ( D ) OTHER INFORMATION: Promoter site ( x i ) SEQUENCE DESCRIPTION: SEQ ID NO:37:

GATCCCTCGA TCCGGATCGA GAGATCCCTC GATCCGGATC GAGAGATCCC TCGATCCGGA          60

TCGAGAGATC C                                                              71

( 2 ) INFORMATION FOR SEQ ID NO:38:

( i ) SEQUENCE CHARACTERISTICS:
                    ( A ) LENGTH: 69 base pairs
                    ( B ) TYPE: nucleic acid
                    ( C ) STRANDEDNESS: single
                    ( D ) TOPOLOGY: linear ( i i ) MOLECULE TYPE: DNA ( i x ) FEATURE:
                    ( A ) NAME/KEY: Other
                    ( B ) LOCATION: 6...7, 28...29, 50...51
                    ( D ) OTHER INFORMATION: Promoter site
                    ( A ) NAME/KEY: Other
                    ( B ) LOCATION: 14...15, 36...37, 58...59
                    ( D ) OTHER INFORMATION: Methylated site
                    ( A ) NAME/KEY: Other
                    ( B ) LOCATION: 22...23, 44...45, 66...67
                    ( D ) OTHER INFORMATION: Terminator site ( x i ) SEQUENCE DESCRIPTION: SEQ ID NO:38:

GGATCTCTCG ATCCGGATCG AGGGATCTCT CGATCCGGAT CGAGGGATCT CTCGATCCGG          60

ATCGAGGGA                                                                 69

( 2 ) INFORMATION FOR SEQ ID NO:39:

( i ) SEQUENCE CHARACTERISTICS:
                    ( A ) LENGTH: 13 base pairs
                    ( B ) TYPE: nucleic acid
                    ( C ) STRANDEDNESS: single
                    ( D ) TOPOLOGY: linear ( i i ) MOLECULE TYPE: DNA ( i x ) FEATURE:
                    ( A ) NAME/KEY: Other
                    ( B ) LOCATION: 5...6
                    ( D ) OTHER INFORMATION: pDbLET Vector ( x i ) SEQUENCE DESCRIPTION: SEQ ID NO:39:

TCGAGCCAGC TAA                                                            13

( 2 ) INFORMATION FOR SEQ ID NO:40:

( i ) SEQUENCE CHARACTERISTICS:
                    ( A ) LENGTH: 7 base pairs
                    ( B ) TYPE: nucleic acid
                    ( C ) STRANDEDNESS: single
                    ( D ) TOPOLOGY: linear ( i i ) MOLECULE TYPE: DNA ( i x ) FEATURE:
                    ( A ) NAME/KEY: Other
                    ( B ) LOCATION: 4...5
                    ( D ) OTHER INFORMATION: pDbLET Vector
                    ( A ) NAME/KEY: Other
                    ( B ) LOCATION: 1

(D) OTHER INFORMATION: Phosphate at nucleotide 1

(x i) SEQUENCE DESCRIPTION: SEQ ID NO:40:

CTGGCTC 7

(2) INFORMATION FOR SEQ ID NO:41:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (i i) MOLECULE TYPE: DNA (i x) FEATURE:
        (A) NAME/KEY: Other
        (B) LOCATION: 6...7, 28...29
        (D) OTHER INFORMATION: Promoter site
        (A) NAME/KEY: Other
        (B) LOCATION: 14...15, 36...37
        (D) OTHER INFORMATION: Methylated inserts
        (A) NAME/KEY: Other
        (B) LOCATION: 22...23, 44...45
        (D) OTHER INFORMATION: Terminator site
        (A) NAME/KEY: Other
        (B) LOCATION: 52...53
        (D) OTHER INFORMATION: pDbLET Vector (x i) SEQUENCE DESCRIPTION: SEQ ID NO:41:

GGATCTCTCG ATCCGGATCG AGGGATCTCT CGATCCGGAT CGAGGGATCG AGCCAGCTAA 60

(2) INFORMATION FOR SEQ ID NO:42:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (i i) MOLECULE TYPE: DNA (i x) FEATURE:
        (A) NAME/KEY: Other
        (B) LOCATION: 1
        (D) OTHER INFORMATION: Phosphate at nucleotide 1
        (A) NAME/KEY: Other
        (B) LOCATION: 4...5
        (D) OTHER INFORMATION: pDbLET Vector
        (A) NAME/KEY: Other
        (B) LOCATION: 12...13, 34...35
        (D) OTHER INFORMATION: Terminator site
        (A) NAME/KEY: Other
        (B) LOCATION: 20...21, 42...43
        (D) OTHER INFORMATION: Methylated inserts
        (A) NAME/KEY: Other
        (B) LOCATION: 28...29, 50...51
        (D) OTHER INFORMATION: Promoter site (x i) SEQUENCE DESCRIPTION: SEQ ID NO:42:

CTGGCTCGAT CCCTCGATCC GGATCGAGAG ATCCCTCGAT CCGGATCGAG AGATCC 56

(2) INFORMATION FOR SEQ ID NO:43:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (i i) MOLECULE TYPE: DNA (i x) FEATURE:
        (A) NAME/KEY: Other (B) LOCATION: 6...7, 29...30
(D) OTHER INFORMATION: Promoter site
(A) NAME/KEY: Other
(B) LOCATION: 14...15, 37...38
(D) OTHER INFORMATION: Methylated inserts
(A) NAME/KEY: Other
(B) LOCATION: 23...24, 46...47
(D) OTHER INFORMATION: Terminator site
(A) NAME/KEY: Other
(B) LOCATION: 54...55
(D) OTHER INFORMATION: pDbLET Vector (xi) SEQUENCE DESCRIPTION: SEQ ID NO:43:

GGATCTCTCG ATCCGCGGCC GGGGGATCTC TCGATCCGCG GCCGGGGGAT CGAGCCAGCT    60

AA    62

(2) INFORMATION FOR SEQ ID NO:44:

(i) SEQUENCE CHARACTERISTICS:
    (A) LENGTH: 58 base pairs
    (B) TYPE: nucleic acid
    (C) STRANDEDNESS: single
    (D) TOPOLOGY: linear (ii) MOLECULE TYPE: DNA (ix) FEATURE:
    (A) NAME/KEY: Other
    (B) LOCATION: 1
    (D) OTHER INFORMATION: Phosphate at nucleotide 1
    (A) NAME/KEY: Other
    (B) LOCATION: 4...5
    (D) OTHER INFORMATION: pDbLET Vector
    (A) NAME/KEY: Other
    (B) LOCATION: 12...13, 35...36
    (D) OTHER INFORMATION: Terminator site
    (A) NAME/KEY: Other
    (B) LOCATION: 21...22, 44...45
    (D) OTHER INFORMATION: Methylated inserts
    (A) NAME/KEY: Other
    (B) LOCATION: 29...30, 52...53
    (D) OTHER INFORMATION: Promoter site (xi) SEQUENCE DESCRIPTION: SEQ ID NO:44:

CTGGCTCGAT CCCCCGGCCG CGGATCGAGA GATCCCCGG CCGCGGATCG AGAGATCC    58

(2) INFORMATION FOR SEQ ID NO:45:

(i) SEQUENCE CHARACTERISTICS:
    (A) LENGTH: 68 base pairs
    (B) TYPE: nucleic acid
    (C) STRANDEDNESS: single
    (D) TOPOLOGY: linear (ii) MOLECULE TYPE: DNA (ix) FEATURE:
    (A) NAME/KEY: Other
    (B) LOCATION: 1
    (D) OTHER INFORMATION: Phosphate at nucleotide 1
    (A) NAME/KEY: Other
    (B) LOCATION: 14...15, 36...37
    (D) OTHER INFORMATION: Promoter site
    (A) NAME/KEY: Other
    (B) LOCATION: 22...23, 44...45
    (D) OTHER INFORMATION: Methylated inserts
    (A) NAME/KEY: Other
    (B) LOCATION: 30...31, 52...53
    (D) OTHER INFORMATION: Terminator site
    (A) NAME/KEY: Other
    (B) LOCATION: 60...61
    (D) OTHER INFORMATION: pDbLET Vector (xi) SEQUENCE DESCRIPTION: SEQ ID NO:45:

```
GGTAGCGAGG ATCTCTCGAT CCGGATCGAG GGATCTCTCG ATCCGGATCG AGGGATCGAG    60

CCAGCTAA                                                              68
```

( 2 ) INFORMATION FOR SEQ ID NO:46:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: Other
        ( B ) LOCATION: 1
        ( D ) OTHER INFORMATION: Phosphate at nucleotide 1
        ( A ) NAME/KEY: Other
        ( B ) LOCATION: 4...5
        ( D ) OTHER INFORMATION: pDbLET Vector
        ( A ) NAME/KEY: Other
        ( B ) LOCATION: 12...13, 34...35
        ( D ) OTHER INFORMATION: Terminator site
        ( A ) NAME/KEY: Other
        ( B ) LOCATION: 20...21, 42...43
        ( D ) OTHER INFORMATION: Methylated inserts
        ( A ) NAME/KEY: Other
        ( B ) LOCATION: 28...29, 50...51
        ( D ) OTHER INFORMATION: Promoter site ( x i ) SEQUENCE DESCRIPTION: SEQ ID NO:46:

```
CTGGCTCGAT CCCTCGATCC GGATGGAGAG ATCCCTCGAT CCGGATGGAG AGATCCGGGC    60

TACCTTAG                                                              68
```

( 2 ) INFORMATION FOR SEQ ID NO:47:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: Other
        ( B ) LOCATION: 1
        ( D ) OTHER INFORMATION: Phosphate at nucleotide 1
        ( A ) NAME/KEY: Other
        ( B ) LOCATION: 4...5
        ( D ) OTHER INFORMATION: pDbLET Vector
        ( A ) NAME/KEY: Other
        ( B ) LOCATION: 12...13, 34...35
        ( D ) OTHER INFORMATION: Terminator site
        ( A ) NAME/KEY: Other
        ( B ) LOCATION: 20...21, 42...43
        ( D ) OTHER INFORMATION: Methylated inserts
        ( A ) NAME/KEY: Other
        ( B ) LOCATION: 28...29, 50...51
        ( D ) OTHER INFORMATION: Promoter site ( x i ) SEQUENCE DESCRIPTION: SEQ ID NO:47:

```
CTGGCTCGAT CCCTCGATCC GGATCGAGAG ATCCCTCGAT CCGGATGGAG AGATCCGGGC    60

TACCTTAG                                                              68
```

( 2 ) INFORMATION FOR SEQ ID NO:48:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear (  i i  ) MOLECULE TYPE: DNA (  i x  ) FEATURE:
    ( A ) NAME/KEY: Oligomer
    ( B ) LOCATION: 1...29
    ( D ) OTHER INFORMATION:

( x i ) SEQUENCE DESCRIPTION: SEQ ID NO:48:

CCTAGCCATG GCCACCTAAC TGGGATCGC      29

( 2 ) INFORMATION FOR SEQ ID NO:49:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: Oligomer
        ( B ) LOCATION: 1...37
        ( D ) OTHER INFORMATION:

( x i ) SEQUENCE DESCRIPTION: SEQ ID NO:49:

GGCCGCGATC CCAGTTAGGT GGCCATGGCT AGGAGCT      37

( 2 ) INFORMATION FOR SEQ ID NO:50:

( i ) SEQUENCE CHARACTERISTICS:
        ( A ) LENGTH: 262 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: CXC-AMN20
        ( B ) LOCATION: 1...262
        ( D ) OTHER INFORMATION:

( x i ) SEQUENCE DESCRIPTION: SEQ ID NO:50:

```
Asn  Ser  His  Phe  Ile  Ile  Thr  Thr  Gln  Gly  Val  Leu  Val  Phe  Asp  Ser
 1              5                        10                       15

Gly  Ser  Ser  Glu  His  Ile  Gly  Asn  Ala  Ile  Ile  Ala  Ala  Val  Lys  Arg
              20                        25                       30

Val  Thr  Glu  Gln  Pro  Ile  Arg  Trp  Val  Val  Asn  Ser  His  Ser  His  Ala
              35                        40                       45

Asp  His  Trp  Leu  Gly  Asn  Ala  Ala  Leu  Ala  Lys  Leu  Gly  Ala  Glu  Leu
      50                        55                       60

Ile  Ser  Thr  Ser  Leu  Ser  Ala  Glu  Thr  Met  Lys  Ser  Asp  Gly  Pro  Val
 65                       70                       75                       80

Asp  Val  Lys  Ala  Phe  Phe  Asn  Met  Thr  Lys  Gly  Ala  Thr  Gly  Glu  Ser
                    85                        90                       95

Thr  Leu  Val  Ile  Pro  Thr  Ser  Ile  Ile  Leu  His  Gln  Gln  Thr  Arg  Thr
              100                       105                      110

Phe  Gly  Asp  Thr  Glu  Val  Glu  Phe  Val  Phe  Ala  Asn  Asp  Gly  His  Ser
              115                       120                      125

Pro  Gly  Asp  Val  Met  Leu  Trp  Leu  Pro  Lys  Gln  Arg  Ile  Leu  Ile  Gly
              130                       135                      140

Gly  Asp  Val  Val  Asn  Ser  Asn  Phe  Met  Pro  Ile  Met  Thr  Pro  Arg  Gly
145                       150                       155                      160
```

```
Asn Ile Thr Gln Leu Ile Ser Val Leu Lys Glu Val Gln Leu Ser
            165             170             175

Pro Leu Leu Val Leu Thr Gly His Gly Glu Asn Thr Ser Val Lys Ser
            180             185             190

Val Ser Arg Asp Ile Gln Phe Leu Thr Tyr Ala Ser Asn Ala Val His
        195             200             205

Glu Ala Leu Val Lys Gly Thr Thr Pro Ala Lys Ile Gln Ala Ser Leu
    210             215             220

Gln Ala Thr Leu Arg Thr Lys Phe Gly Lys Ala Tyr Gln Asp Phe Asp
225             230             235             240

Thr Ser Ile Ser Tyr Leu Leu Glu Met Met Ile Asp Lys Gln Arg Leu
            245             250             255

Gln Phe Ser Pro Ile Thr
            260
```

(2) INFORMATION FOR SEQ ID NO:51:

(i) SEQUENCE CHARACTERISTICS:
        (A) LENGTH: 297 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Actinorhodin Dehydrase
        (B) LOCATION: 1...297
        (D) OTHER INFORMATION:

(xi) SEQUENCE DESCRIPTION: SEQ ID NO:51:

```
Met Thr Val Glu Val Arg Glu Val Ala Glu Gly Val Tyr Ala Tyr Glu
1               5               10              15

Gln Ala Pro Gly Gly Trp Cys Val Ser Asn Ala Gly Ile Val Val Gly
            20              25              30

Gly Asp Gly Ala Leu Val Val Asp Thr Leu Ser Thr Ile Pro Arg Ala
        35              40              45

Arg Arg Leu Ala Glu Trp Val Asp Lys Leu Ala Ala Gly Pro Gly Arg
    50              55              60

Thr Val Val Asn Thr His Phe His Gly Asp His Ala Phe Gly Asn Gln
65              70              75              80

Val Phe Ala Pro Gly Thr Arg Ile Ile Ala His Glu Asp Met Arg Ser
            85              90              95

Ala Met Val Thr Thr Gly Leu Ala Leu Thr Gly Leu Trp Pro Arg Val
            100             105             110

Asp Trp Gly Glu Ile Glu Leu Arg Pro Pro Asn Val Thr Phe Arg Asp
            115             120             125

Arg Leu Thr Leu His Val Gly Glu Arg Gln Val Glu Leu Thr Cys Val
    130             135             140

Gly Pro Ala His Thr Asp His Asp Val Val Val Trp Leu Pro Glu Glu
145             150             155             160

Arg Val Leu Phe Ala Gly Asp Val Val Met Ser Gly Val Thr Pro Phe
            165             170             175

Ala Leu Phe Gly Ser Val Ala Gly Thr Leu Ala Ala Leu Asp Arg Leu
            180             185             190

Ala Glu Leu Glu Pro Glu Val Val Val Gly Gly His Gly Pro Val Ala
        195             200             205

Gly Pro Glu Val Ile Asp Ala Asn Arg Asp Tyr Leu Arg Trp Val Gln
    210             215             220
```

| | | | | | | | | | | | | | | | |
|---|---|---|---|---|---|---|---|---|---|---|---|---|---|---|---|
| Arg<br>225 | Leu | Ala | Ala | Asp | Ala<br>230 | Val | Asp | Arg | Arg | Leu<br>235 | Thr | Pro | Leu | Gln | Ala<br>240 |
| Ala | Arg | Arg | Ala | Asp<br>245 | Leu | Gly | Ala | Phe | Ala<br>250 | Gly | Leu | Leu | Asp | Ala<br>255 | Glu |
| Arg | Leu | Val | Ala<br>260 | Asn | Leu | His | Arg | Ala<br>265 | His | Glu | Glu | Leu | Leu<br>270 | Gly | Gly |
| His | Val | Arg<br>275 | Asp | Ala | Met | Glu | Ile<br>280 | Phe | Ala | Glu | Leu | Val<br>285 | Ala | Tyr | Asn |
| Gly | Gly<br>290 | Gln | Leu | Pro | Thr | Cys<br>295 | Leu | Ala | | | | | | | |

What is claimed is:

1. A mobilizable combinatorial gene expression library, comprising a pool of expression constructs, each expression construct comprising a shuttle vector that replicates in different species or strains of host cell, said shuttle vector containing one or more cDNA or genomic DNA fragments, wherein the cDNA or genomic DNA fragments in the pool of expression constructs are derived from a plurality of species of donor organisms, and wherein the cDNA or genomic DNA fragments are each operably-associated with one or more regulatory regions that drives expression of genes encoded by the cDNA or genomic DNA fragments in an appropriate host organism.

2. The gene expression library of claim 1 wherein the cDNA or genomic DNA fragments contained in the expression constructs are randomly concatenated, and are derived from one or more species of donor organisms.

3. The gene expression library of claim 1 wherein the cDNA or genomic DNA fragments contained in the expression constructs are preselected for a specific property.

4. The gene expression library of claim 1, 2, or 3 in which the expression construct comprises a plasmid vector, a phage vector, a viral vector, a cosmid vector, or an artificial chromosome.

5. The gene expression library of claim 4 in which the vector is a shuttle vector that replicates in different host cell species or strains.

6. The gene expression library of claim 1, 2, or 3 in which the donor organisms comprise a mixture of microorganisms.

7. The gene expression library of claim 1, 2, or 3 in which each expression construct is contained in a host cell.

8. The gene expression library of claim 7 in which the host cells have been modified by the introduction, induction or overproduction of a known metabolic pathway of interest or portion thereof prior to containing the expression constructs.

9. The gene expression library of claim 7 in which the host cell is *Escherichia coli, Bacillus subtilis, Streptomyces lividans, Streptomyces coelicolor, Pseudomonas aeruginosa, Myxococcus xanthus, Saccharomyces cerevisiae, Schizosaccharomyces pombe, Spodoptera frugiperda, Aspergillus nidulans, Arabidopsis thaliana, Nicotiana tabacum*, COS cells, 293 cells, VERO cells, NIH/3T3 cells, or CHO cells.

10. The gene expression library of claim 7 in which the host cells further contain a reporter regimen tailored to identify clones in the library that are expressing desirable metabolic pathways, gene products, or compounds.

11. The gene expression library of claim 7 in which the reporter regimen comprises DNA encoding a reporter gene operably-associated with a regulatory region that is inducible or modulated by the desirable metabolic pathways, gene products, or compounds expressed by the host cell.

12. The gene expression library of claim 7 in which the host cells are in a matrix containing a reporter regimen tailored to identify clones in the library that are expressing desirable metabolic pathways, gene products, or compounds.

13. A method for making a mobilizable combinatorial gene expression library, comprising ligating a shuttle vector that replicates in different species or strains of host cell, to one or more cDNA or genomic DNA fragments to form a pool of expression constructs, wherein said cDNA or genomic DNA fragments in the pool of expression constructs are obtained from a plurality of species of donor organisms, and wherein the genes contained in the cDNA or genomic DNA fragments are each operably-associated with their native or exogenous regulatory regions which drive expression of the genes in an appropriate host cell.

14. The method of claim 13 wherein the cDNA or genomic DNA fragments contained in the expression constructs are randomly concatenated, and are derived from one or more species of donor organisms.

15. The method of claim 13 wherein the cDNA or genomic DNA fragments contained in the expression constructs are preselected for a specific property.

16. The method of claim 13, 14, or 15 in which the DNA vector is a plasmid vector, a phage vector, a viral vector, a cosmid vector, or an artificial chromosome.

17. The method of claim 13, 14, or 15 in which the shuttle vector further comprises an origin of transfer.

18. A method for making a combinatorial gene expression library comprising transferring a pool of expression constructs in a species of host organism to another species or strain of host organism, said expression construct comprising a shuttle vector that replicates in different species or strains of host cell, said shuttle vector comprising one or more cDNA or genomic DNA fragments, wherein the cDNA or genomic DNA fragments in the pool of expression constructs are obtained from a plurality of species of donor organisms, and wherein the genes contained in the cDNA or genomic DNA fragments are each operably-associated with their native or exogenous regulatory regions which drive expression of the genes in an appropriate host cell.

19. The method of claim 18 wherein the pool of expression constructs is transferred by conjugation.

20. The method of claim 18 wherein the pool of expression constructs is transferred by isolating the expression constructs from a first species of host organism, and introducing the expression constructs into a second species or strain of host organism.

21. A method for making a biased combinatorial gene expression library, comprising ligating a DNA vector to one or more cDNA or genomic DNA fragments to generate a library of expression constructs, wherein the cDNA or genomic DNA fragments in the library are obtained from a plurality of species of donor organisms and are selected for a specific property, and wherein genes contained in the cDNA or genomic DNA fragments are each operably-associated with their native or exogenous regulatory regions which drive expression of the genes in an appropriate host cell.

22. The gene expression library of claim 3 wherein the cDNA or genomic DNA fragments are preselected for homology to nucleic acid sequences encoding proteins in a metabolic pathway.

23. The method of claim 15 wherein the cDNA or genomic DNA fragments are preselected for homology to nucleic acid sequences encoding proteins in a metabolic pathway.

24. The gene expression library of claim 1, 2, or 3 in which each expression construct is contained in a host cell that contains proteins that mediate transfer of the expression construct by conjugation.

25. The method of claim 18 wherein the pool of expression constructs is contained in host cells that contain proteins that mediate transfer of the expression constructs by conjugation.

* * * * *